US012594185B2

(12) United States Patent
Mazzone et al.

(10) Patent No.: US 12,594,185 B2
(45) Date of Patent: Apr. 7, 2026

(54) TREATMENT SYSTEM HAVING GENERATOR AND FLUID TRANSFER CARTRIDGE

(71) Applicant: Otsuka Medical Devices Co., Ltd., Tokyo (JP)

(72) Inventors: James D. Mazzone, San Jose, CA (US); Eric Dailey, San Jose, CA (US); Robin Bek, Campbell, CA (US); Kristen Easterday, Mountain View, CA (US); Austin Hendricks, Union City, CA (US); Jeff Gamelsky, Palo Alto, CA (US); Venmathi Gunasekaran, Mountain View, CA (US); Ryan R. Donovan, Santa Clara, CA (US); Ryan J. Hilaman, Oakland, CA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 876 days.

(21) Appl. No.: 17/812,706

(22) Filed: Jul. 14, 2022

(65) Prior Publication Data

US 2023/0016549 A1 Jan. 19, 2023

Related U.S. Application Data

(60) Provisional application No. 63/367,013, filed on Jun. 24, 2022, provisional application No. 63/367,015, (Continued)

(51) Int. Cl.
| | |
|---|---|
| *A61M 3/02* | (2006.01) |
| *A61B 17/32* | (2006.01) |

(Continued)

(52) U.S. Cl.
CPC ...... *A61F 7/123* (2013.01); *A61B 17/320068* (2013.01); *A61F 7/0085* (2013.01);
(Continued)

(58) Field of Classification Search
CPC .............. B21B 1/463; B21B 2027/022; B21B 2203/18; B21B 2267/02; B21B 2267/18;
(Continued)

(56) References Cited

U.S. PATENT DOCUMENTS

| | | | |
|---|---|---|---|
| 4,554,925 | A | 11/1985 | Young |
| 4,643,186 | A | 2/1987 | Rosen |

(Continued)

FOREIGN PATENT DOCUMENTS

| | | |
|---|---|---|
| EP | 1299035 | 4/2003 |
| EP | 1503685 | 2/2005 |

(Continued)

OTHER PUBLICATIONS

Accornero, Neri et al., "Selective Activation of Peripheral Nerve Fibre Groups of Different Diameter By Triangular Shaped Stimulus Pulses", J. Physiol. (1977), 273, _ 539-560, 22 Q9S.

(Continued)

*Primary Examiner* — Tigist S Demie
(74) *Attorney, Agent, or Firm* — Theresa Ann Raymer

(57) ABSTRACT

A treatment system includes a generator and a fluid transfer cartridge. The fluid transfer cartridge includes a cartridge shell having a cartridge cavity. The cartridge cavity is between a front face and a rear face. A syringe barrel is disposed within the cartridge cavity, and has a syringe cavity. The fluid transfer cartridge includes a cartridge manifold in the cartridge cavity. The cartridge manifold includes a fluid transfer plate having a front fluid channel in a front plate surface, and a rear fluid channel in a rear plate surface. The cartridge manifold includes a fluid port extend- (Continued)

ing through the fluid transfer plate from the front fluid channel to the rear fluid channel. The front fluid channel, the rear fluid channel, and the fluid port are in fluid communication with the syringe cavity. Other embodiments are also described and claimed.

29 Claims, 24 Drawing Sheets

Related U.S. Application Data filed on Jun. 24, 2022, provisional application No. 63/287,358, filed on Dec. 8, 2021, provisional application No. 63/223,518, filed on Jul. 19, 2021.

(51) Int. Cl.

| | | |
|---|---|---|
| *A61F 7/00* | (2006.01) | |
| *A61F 7/12* | (2006.01) | |
| *A61B 90/00* | (2016.01) | |

(52) U.S. Cl.
CPC ...................... *A61M 3/0201* (2021.05); *A61B 2017/320069* (2017.08); *A61B 2090/0472* (2016.02); *A61B 2217/007* (2013.01); *A61F 2007/0056* (2013.01); *A61F 2007/126* (2013.01)

(58) Field of Classification Search
CPC ... B21B 2267/24; B21B 27/02; B21B 27/021; A61B 17/320068; A61B 2017/320069; A61B 2018/00023; A61B 2018/00285; A61B 2018/00404; A61B 2018/00434; A61B 2018/00511; A61B 2018/00863; A61B 2090/0472; A61B 2090/064; A61B 2217/007; A61F 2007/0056; A61F 2007/126; A61F 7/0085; A61F 7/123; A61M 3/0201; A61N 2007/003; A61N 2007/0047
See application file for complete search history.

(56) References Cited

U.S. PATENT DOCUMENTS

| | | | |
|---|---|---|---|
| 4,650,466 | A | 3/1987 | Luther |
| 4,709,698 | A | 12/1987 | Johnston et al. |
| 4,841,977 | A | 6/1989 | Griffith et al. |
| 4,983,169 | A | 1/1991 | Furukawa |
| 5,000,185 | A | 3/1991 | Yock |
| 5,114,423 | A | 5/1992 | Kasprzyk |
| 5,368,591 | A | 11/1994 | Lennox |
| 5,391,197 | A | 2/1995 | Burdette et al. |
| 5,423,811 | A | 6/1995 | Imran et al. |
| 5,558,672 | A | 9/1996 | Edwards et al. |
| 5,575,788 | A | 11/1996 | Baker et al. |
| 5,657,755 | A | 8/1997 | Desai |
| 5,685,839 | A | 11/1997 | Edwards et al. |
| 5,688,266 | A | 11/1997 | Edwards et al. |
| 5,800,482 | A | 9/1998 | Pomeranz et al. |
| 6,066,134 | A | 5/2000 | Eggers et al. |
| 6,097,985 | A | 8/2000 | Kasevich et al. |
| 6,117,101 | A | 9/2000 | Diederich et al. |
| 6,254,598 | B1 | 7/2001 | Edwards |
| 6,283,989 | B1 | 9/2001 | Laufer et al. |
| 6,292,695 | B1 | 9/2001 | Webster |
| 6,296,619 | B1 | 10/2001 | Brisken et al. |
| 6,383,151 | B1 | 5/2002 | Diederich et al. |
| 6,514,249 | B1 | 2/2003 | Maguire et al. |
| 6,529,756 | B1 | 3/2003 | Phar |
| 6,564,096 | B2 | 5/2003 | Mest |
| 6,584,360 | B2 | 6/2003 | Francischelli et al. |
| 6,635,054 | B2 | 10/2003 | Fjield et al. |
| 6,648,883 | B2 | 11/2003 | Francischelli et al. |
| 6,669,655 | B1 | 12/2003 | Acker |
| 6,692,490 | B1 | 2/2004 | Edwards |
| 6,719,755 | B2 | 4/2004 | Sliwa, Jr. et al. |
| 6,763,722 | B2 | 7/2004 | Fjield et al. |
| 6,837,886 | B2 | 1/2005 | Collins |
| 6,845,267 | B2 | 1/2005 | Harrison et al. |
| 6,954,977 | B2 | 10/2005 | Maguire |
| 7,052,695 | B2 | 5/2006 | Kalish |
| 7,156,816 | B2 | 1/2007 | Schwartz et al. |
| 7,162,303 | B2 | 1/2007 | Levin et al. |
| 7,371,231 | B2 | 5/2008 | Rioux et al. |
| 7,510,536 | B2 | 3/2009 | Foley et al. |
| 7,540,846 | B2 | 6/2009 | Harhen et al. |
| 7,617,005 | B2 | 11/2009 | Demarais et al. |
| 7,621,873 | B2 | 11/2009 | Owen et al. |
| 7,653,438 | B2 | 1/2010 | Deem et al. |
| 7,717,948 | B2 | 5/2010 | Demarais et al. |
| 7,837,676 | B2 | 11/2010 | Sinelnikov et al. |
| 7,942,871 | B2 | 5/2011 | Thapliyal et al. |
| 8,024,050 | B2 | 9/2011 | Libbus et al. |
| 8,025,688 | B2 | 9/2011 | Diederich et al. |
| 8,137,274 | B2 | 3/2012 | Weng et al. |
| 8,447,414 | B2 | 5/2013 | Johnson et al. |
| 8,483,831 | B1 | 7/2013 | Hiavka et al. |
| 8,626,300 | B2 | 1/2014 | Demarais et al. |
| 8,702,619 | B2 | 4/2014 | Wang |
| 8,774,913 | B2 | 7/2014 | Demarais et al. |
| 8,790,281 | B2 | 7/2014 | Diederich et al. |
| 8,818,514 | B2 | 8/2014 | Zarins et al. |
| D712,352 | S | 9/2014 | George et al. |
| D712,353 | S | 9/2014 | George et al. |
| D712,833 | S | 9/2014 | George et al. |
| 8,845,629 | B2 | 9/2014 | Demarais et al. |
| 8,932,289 | B2 | 1/2015 | Mayse et al. |
| 9,022,948 | B2 | 5/2015 | Wang |
| 9,028,472 | B2 | 5/2015 | Mathur et al. |
| 9,066,720 | B2 | 6/2015 | Ballakur et al. |
| 9,072,902 | B2 | 7/2015 | Mathur et al. |
| 9,155,590 | B2 | 10/2015 | Mathur |
| 9,186,198 | B2 | 11/2015 | Demarais et al. |
| 9,186,212 | B2 | 11/2015 | Nabulovsky et al. |
| 9,289,132 | B2 | 3/2016 | Ghaffari |
| 9,326,816 | B2 | 5/2016 | Srivastava |
| 9,327,123 | B2 | 5/2016 | Yamasaki |
| 9,333,035 | B2 | 5/2016 | Rudie |
| 9,339,332 | B2 | 5/2016 | Srivastava |
| 9,345,530 | B2 | 5/2016 | Ballakur et al. |
| 9,375,154 | B2 | 6/2016 | Wang |
| 9,427,579 | B2 | 8/2016 | Fain et al. |
| 9,439,598 | B2 | 9/2016 | Shimada et al. |
| 9,649,064 | B2 | 5/2017 | Toth et al. |
| 9,700,372 | B2 | 7/2017 | Schaer |
| 9,707,034 | B2 | 7/2017 | Schaer |
| 9,723,998 | B2 | 8/2017 | Wang |
| 9,730,639 | B2 | 8/2017 | Toth et al. |
| 9,743,845 | B2 | 8/2017 | Wang |
| 9,750,560 | B2 | 9/2017 | Ballakur et al. |
| 9,770,291 | B2 | 9/2017 | Wang et al. |
| 9,770,593 | B2 | 9/2017 | Gross |
| 9,801,684 | B2 | 10/2017 | Fain |
| 9,820,811 | B2 | 11/2017 | Wang |
| 9,907,983 | B2 | 3/2018 | Thapliyal et al. |
| 9,931,047 | B2 | 4/2018 | Srivastava |
| 9,943,666 | B2 | 4/2018 | Warnking |
| 9,956,034 | B2 | 5/2018 | Toth et al. |
| 9,968,790 | B2 | 5/2018 | Toth et al. |
| 9,981,108 | B2 | 5/2018 | Warnking |
| 9,999,463 | B2 | 6/2018 | Puryear et al. |
| 10,004,458 | B2 | 6/2018 | Toth et al. |
| 10,004,557 | B2 | 6/2018 | Gross et al. |
| 10,010,364 | B2 | 7/2018 | Harringtpm |
| 10,016,233 | B2 | 7/2018 | Pike |
| 10,022,085 | B2 | 7/2018 | Toth et al. |
| 10,039,901 | B2 | 8/2018 | Warnking |
| 10,123,903 | B2 | 11/2018 | Warnking et al. |
| 10,143,419 | B2 | 12/2018 | Toth et al. |
| 10,179,020 | B2 | 1/2019 | Ballakur et al. |
| 10,179,026 | B2 | 1/2019 | Ng |

(56)                    References Cited

U.S. PATENT DOCUMENTS

| | | | |
|---|---|---|---|
| 10,182,865 B2 | 1/2019 | Naga et al. |
| 10,226,633 B2 | 3/2019 | Toth et al. |
| 10,245,429 B2 | 4/2019 | Deem et al. |
| 10,279,119 B2 | 5/2019 | Leary |
| 10,292,610 B2 | 5/2019 | Srivastava |
| 10,293,190 B2 | 5/2019 | Zarins et al. |
| 10,350,440 B2 | 7/2019 | Taylor |
| 10,363,359 B2 | 7/2019 | Toth et al. |
| 10,368,775 B2 | 8/2019 | Hettrick et al. |
| 10,368,944 B2 | 8/2019 | Schaer |
| 10,376,310 B2 | 8/2019 | Fain et al. |
| 10,383,685 B2 | 8/2019 | Gross et al. |
| 10,398,332 B2 | 9/2019 | Min et al. |
| 10,420,902 B2 | 9/2019 | Cowan et al. |
| 10,456,605 B2 | 10/2019 | Taylor |
| 10,470,684 B2 | 11/2019 | Toth et al. |
| 10,478,249 B2 | 11/2019 | Gross et al. |
| 10,499,937 B2 | 12/2019 | Warnking |
| 10,543,037 B2 | 1/2020 | Shah |
| 10,596,321 B2 | 3/2020 | Mandaroux et al. |
| 10,850,091 B2 | 12/2020 | Zarins et al. |
| 11,801,085 B2 | 10/2023 | Wu et al. |
| 2001/0023365 A1 | 9/2001 | Medhkour et al. |
| 2002/0042610 A1 | 4/2002 | Sliwa, Jr. et al. |
| 2002/0072741 A1 | 6/2002 | Sliwa, Jr. et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2003/0004439 A1 | 1/2003 | Pant et al. |
| 2003/0028111 A1 | 2/2003 | Vaezy et al. |
| 2003/0074039 A1 | 4/2003 | Puskas |
| 2003/0114878 A1 | 6/2003 | Diederich et al. |
| 2003/0125726 A1 | 7/2003 | Maguire et al. |
| 2003/0181963 A1 | 9/2003 | Pellegrino et al. |
| 2003/0216721 A1 | 11/2003 | Diederich et al. |
| 2003/0216792 A1 | 11/2003 | Levin |
| 2004/0019349 A1 | 1/2004 | Fuimaono et al. |
| 2004/0082859 A1 | 4/2004 | Schaer |
| 2004/0097819 A1 | 5/2004 | Duarte |
| 2004/0106880 A1 | 6/2004 | Weng et al. |
| 2004/0122494 A1 | 6/2004 | Eggers et al. |
| 2004/0181178 A1 | 9/2004 | Aldrich et al. |
| 2004/0242999 A1 | 12/2004 | Vitek et al. |
| 2005/0038340 A1 | 2/2005 | Vaezy et al. |
| 2005/0159738 A1 | 7/2005 | Visram et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0261672 A1 | 11/2005 | Deem et al. |
| 2005/0288730 A1 | 12/2005 | Deem |
| 2006/0041277 A1 | 2/2006 | Deem et al. |
| 2006/0052695 A1 | 3/2006 | Adam et al. |
| 2006/0058711 A1 | 3/2006 | Harhen et al. |
| 2006/0064081 A1 | 3/2006 | Rosinko |
| 2006/0118127 A1 | 6/2006 | Chinn |
| 2006/0142827 A1 | 6/2006 | Willard et al. |
| 2006/0184069 A1 | 8/2006 | Vaitekunas |
| 2006/0217772 A1 | 9/2006 | Libbus et al. |
| 2006/0235286 A1 | 10/2006 | Stone et al. |
| 2007/0060921 A1 | 3/2007 | Janssen et al. |
| 2007/0072741 A1 | 3/2007 | Robideau |
| 2007/0106292 A1 | 5/2007 | Kaplan |
| 2007/0135875 A1 | 6/2007 | Demarais et al. |
| 2008/0039746 A1 | 2/2008 | Hissong et al. |
| 2008/0215031 A1 | 9/2008 | Belfort et al. |
| 2009/0234407 A1 | 9/2009 | Hastings et al. |
| 2009/0248005 A1 | 10/2009 | Rusin et al. |
| 2009/0254160 A1* | 10/2009 | Shawver .................. A61F 7/02 |
| | | 607/104 |
| 2011/0118723 A1 | 5/2011 | Turner et al. |
| 2011/0125206 A1 | 5/2011 | Bornzin |
| 2011/0208096 A1 | 8/2011 | Demarais et al. |
| 2012/0004656 A1 | 1/2012 | Jackson et al. |

| | | | |
|---|---|---|---|
| 2012/0265198 A1 | 10/2012 | Crow et al. |
| 2012/0296232 A1 | 11/2012 | Ng |
| 2013/0023897 A1 | 1/2013 | Wallace |
| 2013/0085489 A1 | 4/2013 | Fain et al. |
| 2013/0096550 A1 | 4/2013 | Hill |
| 2013/0116737 A1 | 5/2013 | Edwards et al. |
| 2013/0123770 A1 | 5/2013 | Smith |
| 2013/0131743 A1 | 5/2013 | Yamasaki et al. |
| 2013/0150749 A1 | 6/2013 | McLean et al. |
| 2013/0165925 A1 | 6/2013 | Mathur et al. |
| 2013/0172872 A1 | 7/2013 | Subramaniam |
| 2013/0274614 A1 | 10/2013 | Shimada et al. |
| 2013/0289369 A1 | 10/2013 | Margolis |
| 2013/0289682 A1 | 10/2013 | Barman et al. |
| 2014/0018788 A1 | 1/2014 | Engelman et al. |
| 2014/0058294 A1 | 2/2014 | Gross et al. |
| 2014/0257271 A1 | 9/2014 | Mayse et al. |
| 2014/0274614 A1 | 9/2014 | Min et al. |
| 2014/0275924 A1 | 9/2014 | Min et al. |
| 2014/0276792 A1 | 9/2014 | Holaira |
| 2014/0288551 A1 | 9/2014 | Bharmi et al. |
| 2014/0288616 A1 | 9/2014 | Rawat et al. |
| 2014/0303617 A1 | 10/2014 | Shimada |
| 2015/0289931 A1 | 10/2015 | Puryear et al. |
| 2016/0000345 A1 | 1/2016 | Kobayashi et al. |
| 2016/0045121 A1 | 2/2016 | Akingba et al. |
| 2017/0027460 A1 | 2/2017 | Shimada et al. |
| 2017/0035310 A1 | 2/2017 | Shimada et al. |
| 2017/0296264 A1 | 10/2017 | Wang |
| 2018/0015274 A1* | 1/2018 | Haury .................. A61M 39/24 |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0151670 A1 | 5/2019 | Toth et al. |
| 2019/0183560 A1 | 6/2019 | Ballakur et al. |
| 2019/0307361 A1 | 10/2019 | Hettrick et al. |
| 2020/0046248 A1 | 2/2020 | Toth et al. |
| 2020/0077907 A1 | 3/2020 | Shimada et al. |

FOREIGN PATENT DOCUMENTS

| | | |
|---|---|---|
| EP | 1579889 | 9/2005 |
| EP | 2359764 | 8/2011 |
| EP | 2430996 | 3/2012 |
| EP | 2842604 | 3/2015 |
| EP | 2968984 | 1/2016 |
| EP | 2995250 | 3/2016 |
| EP | 2482930 | 7/2017 |
| EP | 2968797 | 2/2020 |
| EP | 3799931 | 4/2021 |
| WO | WO1999/002096 | 1/1999 |
| WO | WO2001/095820 | 12/2001 |
| WO | WO2002/005897 | 1/2002 |
| WO | WO 2002/019934 | 3/2002 |
| WO | WO2003/022167 | 3/2003 |
| WO | WO2003/051450 | 6/2003 |
| WO | WO2006/041881 | 4/2006 |
| WO | WO2006/060053 | 6/2006 |
| WO | WO2007/014003 | 2/2007 |
| WO | WO 2012/112165 | 8/2012 |
| WO | WO 2017/039570 | 3/2017 |

(56) References Cited

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).

American Heart Association—Pulmonary Hypertension: High Blood Pressure in the Heart-to-Lung System, (last reviewed Oct. 31, 2016).

Appeal Brief of Patent Owner from Reexamination 95-002, 110.

Aytac, et al., "Correlation Between the Diameter of the Main Renal Artery and the Presence of an Accessory Renal Artery", J Ultrasound Med 22:433-439, 2003 (.

Azizi, Michel et al., Ultrasound renal denervation for hypertension resistant to a triple medication pill (RADIANCE-HTN TRIO): a randomised, multicentre, single-blind, sham-controlled trial, 397 Lancet 2476 (2021).

Bailey, M.R. et al., Physical Mechanisms of the Therapeutic Effect of Ultrasound (A Review), Acoustical Physics, vol. 49, No. 4, 2003, pp. 369-388.

Bengel, et al., Serial Assessment of Sympathetic Reinnervation After Orthotopic Heart Transplantation; A Longitudinal Study Using PET and C-11 Hydroxyephedrine, Circulation. 1999;99:1866-1871.

Berjano, E. et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.

Bhatt, D.L., et al., A Controlled Trial of Renal Denervation for Resistant Hypertension, New England J. Med., 370:1393-1401 (2014).

Bhatt, Deepak L. et al., Long-term outcomes after catheter-based renal artery denervation for resistant hypertension: final follow-up of the randomised Symplicity HTN-3 Trial, 400 Lancet 1405 (2022).

Billard, B.E. et al., Effects of Physical Parameters on High Temperature Ultrasound Hyperthermia, Ultrasound in Med. & Biol. Vol. 16, No. 4, pp. 409-420, 1990.

Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).

Blanketjin, Peter, Sympathetic Hyperactivity in Chronic Kidney Disease, Neprhrol Dial Transplant, vol. 19, No. 6, 1354-1357 (2004).

Blum et al., Treatment of Ostial Renal-Artery Stenoses with Vascular Endoprostheses after Unsuccessful Balloon Angioplasty, N. Engl. J. Med. 336 459-65 (1997).

Bonsignore, C., "A Decade of Evolution in Stent Design", Proceedings of the International Conference on Shape Memory and Superelastic Technologies, (2003).

Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).

Bush, et al., "Endovascular revascularization of renal artery stenosis: Technical and clinical results", Journal of Vascular Surgery, 2001, May, 1041-1049 (2001).

Camasao, D. B. et al., The mechanical characterization of blood vessels and their substitutes in the continuous quest for physiological-relevant performances: A critical review, Materials Today Bio, vol. 10 (2021).

Carter, J., "Microneurography and Sympathetic Nerve Activity: A Decade-By-Decade Journey across 50 Years," Journal of Neurophysiology, vol. 121, No. 4. doi: 10.1 152/jn.00570.2018.

Carter, Stefan et al., Measurement of Renal Artery Pressures by Catheterization in Patients with and without Renal Artery Stenosis, Circulation, vol. XXXIII, 443-449 (1966).

Chapelon, J.Y., "Treatment of Localised Prostate Cancer with Transrectal High Intensity Focused Ultrasound, "European Journal of Ultrasound 9, 31-38, 1999.

Charlesworth, Peter et al., Renal Artery Injury from a Fogarty Balloon Catheter, Journal of Vascular Surgery, vol. 1, No. 4, 573-576 (1984).

Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Chiesa et al., Endovascular Stenting for the Nutcracker Phenomenon, J. Endovasc. Ther., 8:652-655 (2001).

Coates, Paul et al., "Time, Temperature, Power, and Impedance Considerations for Radiofrequency Catheter Renal Denervation," Cardiovascular Revascularization Medicine 42, 171-177 (2022).

Corrected Patent Owner's Response to Office Action, dated May 10, 2013, from File History of Inter Partes Reexamination U.S. Appl. No. 95/002,110.

Correspondence from PTAB Deputy Chief Clerk to Counsel re conference call request-Exhibit 3001 in the Patent Trial and Appeal Board, United States Patent and Trademark Office, Petition No. PTAB-IPR2022-00431.

Curriculum Vitae of Dr. Chris Daft.

Curriculum Vitae of Dr. John M. Moriarty.

Curriculum Vitae of Dr. Michael Bohm.

Curriculum Vitae of Farrell Mendelsohn.

Dangas, G., et al., Intravascular Ultrasound-Guided Renal Artery Stenting, J Endovasc Ther, 2001;8:238-247 (2001).

Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).

Deardorff, Dana et al., Ultrasound Applicators with Internal Cooling for Interstitial Thermal Therapy, SPIE vol. 3594, 36-46, Jan. 1999.

Decision of the Patent Trial and Appeal Board in U.S. Appl. No. 14/731,347.

Declaration of Chris Daft dated Jan. 11, 2022, in the Patent Trial and Appeal Board, United States Patent and Trademark Office, Petition No. PTAB-IPR2022-00431.

Second Declaration of Chris Daft. Dated Jan. 10, 2023, in the Patent Trial and Appeal Board, United States Patent and Trademark Office, Petition No. PTAB-IPR2022-00431.

Declaration of Dr. Daniel van der Weide, dated Oct. 26, 2022, in the Patent Trial and Appeal Board, United States Patent and Trademark Office, Petition No. PTAB-IPR2022-00431.

Declaration of Dr. Dieter Haemmerich, dated Aug. 29, 2012, in the Patent Trial and Appeal Board, United States Patent and Trademark Office, In re U.S. Pat. No. 7,717,948.

Declaration of Dr. John M. Moriarty in German Nullity proceedings for EP2261905 dated Jul. 13, 2022.

Declaration of Dr. John Moriarty, dated Jan. 19, 2023, in the Patent Trial and Appeal Board, United States Patent and Trademark Office, Petition No. PTAB-IPR2022-00431.

Declaration of Jonathan Bradford in Support of Patent Owner's Response, dated Oct. 27, 2022.

Declaration of Jonathan Bradford dated May 10, 2022, in the Patent Trial and Appeal Board, United States Patent and Trademark Office, Petition No. PTAB-IPR2022-00431.

Declaration of Dr. Michael Bohm dated Sep. 29, 2022 on behalf of Medtronic Inc.

Declaration of Dr. Robert Tucker, dated Oct. 27, 2022, in the Patent Trial and Appeal Board, United States Patent and Trademark Office, Petition No. PTAB-IPR2022-00431.

Declaration of Farrell Mendelsohn dated Jan. 10, 2022, in the Patent Trial and Appeal Board, United States Patent and Trademark Office, Petition No. PTAB-IPR2022-00431.

Defendant's Reply to Court Order of Oct. 4, 2022 and Plaintiff's Surrejoinder of Sep. 29, 2022 in the Mannheim District Court, case No. 7 O 14/21, dated Oct. 31, 2022.

Defendant's Response dated May 11, 2022 in the Munich Federal Patent Court, Nullity Suit 6 Ni 32/22.

Dibona, Gerald F., "Neural Control of the Kidney, Past, Present and Future," 41 [Part II] Hypertension 621 24 (2003).

Dibona, Gerald, Sympathetic Nervous System and Kidney in Hypertension, Current Opinion in Nephrology and Hypertension, vol. 11, 197-200 (2002).

(56)                    References Cited

OTHER PUBLICATIONS

Dibona, Gerald F. et al., "Neural Control of Renal Function", 77 Physiological Reviews No. 1, 75 (1997).
Diederich, et al., "Catheter-based Ultrasound Applicators for Selective Thermal Ablation: progress towards MRI-guided applications in prostate," International Journal of Hyperthermia, 20:7, 739-756.
Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Diedrich, A. et al.," Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_doi:10.1109fTBME.2002. 807323.
Draney, Mary et al., Three-Dimensional Analysis of Renal Artery Bending Motion During Respiration, International Society of Endovascular Specialists, vol. 12, 380-386 (2005).
Erikson, Kenneth et al., Ultrasound in Medicine: A Review, IEEE Transactions on Sonics and Ultrasonics, vol. 21, No. 3 (1974).
EP Board of Appeals Communication dated Dec. 17, 2019—Preliminary Remarks for EP appeal No. T2680/16-3.3.4.01.
European Search Report in Application No. 12180431.4 dated Jan. 17, 2013.
European Communication in Application No. 12180431.4 dated Oct. 23, 2013.
European Office Action in Application No. 12180431.4.
European Patent No. 12167931, Claims of the Main Request dated Sep. 30, 2016.
European Search Report (Supplementary) in Application No. 14775754.6 dated Feb. 17, 2016.
European Search Report in Application No. 218186547 dated Nov. 19, 2018.
European Search Report in Application No. 20202272.9 dated Mar. 1, 2021.
Fan, Xiaobing et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Fengler, Karl et al., A Three-Arm Randomized Trial of Different Renal Denervation Devices and Techniques in Patients with Resistant Hypertension (RADIOSOUND-HTN), 139 Circulation 590 (2019).
File History to EP1802370B1 Part 1.
File History to EP1802370B1 Part 2.
File History to EP1802370B1 Part 3.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).

Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
Hansen et al., The Transplanted Human Kidney Does Not Achieve Functional Reinnervation, 87 Clinical Science 13 (1994).
Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, Sep. 1 958, 1 1 pages.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).
Huang, et al., Renal Denervation Prevents and Reverses Hyperinsulinemia-Induced Hypertension in Rats, Hypertension 32 (1998) pp. 249-254.
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kapural, Leonardo, et al., "Radiofrequency Ablation for Chronic Pain Control," Anesthetic Techniques in Pain Management, pp. 517-525, 2001.
Katholi, R.E., et al., Importance of Renal Sympathetic Tone in the Development of DOCA-Salt Hypertension in The Rat, Hypertension, 2:266-273 (1980).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, MASSDEVICE (Dec. 6, 2016).
Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Koomans, Hein et al., Sympathetic Hyperactivity in Chronic Renal Failure: A wake-up call, Frontiers in Nephrology, vol. 15, 524-537 (2004).
Kuo, et al., "Atrial Fibrillation: New Horizons", Chang Gung Med J vol. 26 No. 10 Oct. 2003.
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).

(56)                    References Cited

OTHER PUBLICATIONS

Lee, Jong Deok et al., MR imaging-histopathologic correlation of radiofrequency thermal ablation lesion in a rabbit liver model: observation during acute and chronic stages, 2 Korean J. Radiol. 151 (2001).

Levin, S., et al., ARDIAN: Succeeding Where Drugs Fail-Treating Hypertension in the Cath Lab, In Vivo, 27:23 (2009).

Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).

Marine, Joseph E., Catheter ablation therapy for supraventricular arrhythmias, 298 JAMA 2768 (2007).

Martin, Louis K. et al., Long-term Results of Angioplasty in 110 Patients with Renal Artery Stenosis, Journal of Vascular and Interventional Radiology, vol. 3, No. 4, 619-626 (1992).

Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.

Matsumoto, Edward D. et al., Short-term efficacy of temperature-based radiofrequency ablation of small renal tumors, 65 Urology 877 (2005).

Medtronic Press Release, Medtronic Announces U.S. Renal Denervation Pivotal Trial Fails to Meet Primary Efficacy Endpoint While Meeting Primary Safety Endpoint (Jan. 9, 2014).

Medtronic Inc., Renal Denervation (RDN): Novel Catheter-Based Treatment for Hypertension, Scientific Background, 2011.

Medtronic Scientific Background, Hypertension and the Symplicity Renal Denervation System.

Medtronic, Symplicity RDN Common System Q&A.

Medtronic Inc., The Symplicity RDN System, 2012.

Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).

Millard, et al., Renal Embolization for Ablation of Function In Renal Failure And Hypertension, Postgraduate Med. J. 65, 729-734 (1989).

Mitchell, et al., "The Renal Nerves" British Journal of Urology, Read by invitation at the Sixth Annual Meeting of the British Association of Urological Surgeons on Jun. 30, 1950.

Morrissey, D. M. "Sympathectomy in the treatment of hypertension." Lancet, CCLXIV:403-408 (1953).

Nair et al., "The Need for and the Challenges of Measuring Renal Sympathetic Nerve Activity," Heart Rhythm 2016; 13:1166-1171.

Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).

Netter, Frank, Atlas of Human Anatomy, Icon Learning Systems, Rochester, NY (2002).

Neumann, Jutta, Sympathetic hyperactivity in chronic kidney disease: Pathogenesis, clinical relevance, and treatment, International Society of Nephrology, vol. 65, 1568-1576 (2004).

News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.

Notice of Deposition of Tucker, filed Dec. 30, 2022 in the Patent Trial and Appeal Board, United States Patent and Trademark Office, Petition No. PTAB-IPR2022-00431.

Notice of Deposition of van der Weide, filed Dec. 30, 2022 in the Patent Trial and Appeal Board, United States Patent and Trademark Office, Petition No. PTAB-IPR2022-00431.

Notice re filing date accorded, dated Feb. 10, 2022 in the Patent Trial and Appeal Board, United States Patent and Trademark Office, Petition No. PTAB-IPR2022-00431.

Nozawa, T., et al. "Effects of long-term renal sympathetic denervation on heart failure after myocardial infarction in rats." Heart Vessels, 16:51-56 (2002).

Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").

Olsson, R et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.

Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.

Order Setting Oral Hearing 37 C.F.R. § 42.70, dated Mar. 24, 2023 in the Patent Trial and Appeal Board, United States Patent and Trademark Office, Petition No. PTAB-IPR2022-00431.

Osborn, J., "Catheter-Based Renal Nerve Ablation as a Novel Hypertension Therapy, Lost, and Then Found," in Translation.

Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).

Page, Irvine H. & George J. Heuer, The Effect of Renal Denervation on Patients Suffering from Nephritis, 14 J. Clinical Investigation 443 (1935) (received for publication in 1935).

Papademetriou, Vasilios et al., Renal Sympathetic Denervation for the Treatment of Difficult-to- Control or Resistant Hypertension, 2011 Int. J. Hypertension, Article 196518 (2011).

Papademetriou, et al., "Renal Sympathetic Denervation: Hibernation or Resurrection?", Cardiology 2016; 135, 11 pgs.

Papadopoulos, N., "Evaluation of a Small Flat Rectangular Therapeutic Ultrasonic Transducer Intended for Intravascular Use," Ultrasonics 74, 196-203, 2017.

Pappone C, et al., "Circumferential radiofrequency ablation of pulmonary vein ostia: a new anatomic approach for curing atrial fibrillation", Circulation. 2000; 102(21): 2619-2628. (2000).

Patent Owner's Amended Objections to Evidence Under 37 C.F.R. §42.64.

Patent Owner's Mandatory Notice, filed Feb. 3, 2022 in the Patent Trial and Appeal Board, United States Patent and Trademark Office, Petition No. PTAB-IPR2022-00431.

Patent Owner's Notice of Deposition of Dr. Chris Daft, filed Sep. 20, 2022 in the Patent Trial and Appeal Board, United States Patent and Trademark Office, Petition No. PTAB-IPR2022-00431.

Patent Owner's Notice of Deposition of Dr. Chris Daft filed Feb. 21, 2023 in the Patent Trial and Appeal Board, United States Patent and Trademark Office, Petition No. PTAB-IPR2022-00431.

Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.

Patent Owner's Notice of Deposition of Dr. John Moriarty, filed Feb. 21, 2023 in the Patent Trial and Appeal Board, United States Patent and Trademark Office, Petition No. PTAB-IPR2022-00431.

Patent Owner's Objections to Evidence, filed Aug. 18, 2022 in the Patent Trial and Appeal Board, United States Patent and Trademark Office, Petition No. PTAB-IPR2022-00431.

Patent Owner's Power of Attorney, filed Feb. 3, 2022 in the Patent Trial and Appeal Board, United States Patent and Trademark Office, Petition No. PTAB-IPR2022-00431.

Patent Owner Medtronic Ireland Power of Attorney, filed May 10, 2022 in the Patent Trial and Appeal Board, United States Patent and Trademark Office, Petition No. PTAB-IPR2022-00431.

Patent Owner's Preliminary Response, filed May 10, 2022 in the Patent Trial and Appeal Board, United States Patent and Trademark Office, Petition No. PTAB-IPR2022-00431.

Patent Owner's Request for Oral Hearing, filed Mar. 23, 2023 in the Patent Trial and Appeal Board, United States Patent and Trademark Office, Petition No. PTAB-IPR2022-00431.

(56) References Cited

OTHER PUBLICATIONS

Patent Owner's Response, filed Oct. 27, 2022 in the Patent Trial and Appeal Board, United States Patent and Trademark Office, Petition No. PTAB-IPR2022-00431.

Patent Owner's Sur-Reply, filed Mar. 9, 2023 in the Patent Trial and Appeal Board, United States Patent and Trademark Office, Petition No. PTAB-IPR2022-00431.

Patent Owner's Updated Mandatory Notice, filed May 10, 2022 in the Patent Trial and Appeal Board, United States Patent and Trademark Office, Petition No. PTAB-IPR2022-00431.

Peet, M.M., Hypertension and Its Surgical Treatment by Bilateral Supradiaphragmatic Splanchnicectomy, Am. J. Surgery, LXXV:48-68 (1948).

Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.

Petitioner ReCor's Biography of Dr. Neil C. Barman.

Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.

Petitioner's Power of Attorney for Recor Medical, Inc., filed Jan. 13, 2022 in the Patent Trial and Appeal Board, United States Patent and Trademark Office, Petition No. PTAB-IPR2022-00431.

Petitioner Reply, filed Jan. 23, 2023 in the Patent Trial and Appeal Board, United States Patent and Trademark Office, Petition No. PTAB-IPR2022-00431.

Petitioners' Request for Oral Argument, filed Mar. 21, 2023 in the Patent Trial and Appeal Board, United States Patent and Trademark Office, Petition No. PTAB-IPR2022-00431.

Petitioners' Updated Mandatory Notices, dated Jan. 18, 2022 in the Patent Trial and Appeal Board, United States Patent and Trademark Office, Petition No. PTAB-IPR2022-00431.

Plaintiff's Nullity Brief, dated Jan. 14, 2022, in the Munich Federal Patent Court, Nullity Suit 6 Ni 32/22.

Plaintiff's Reply to the May 11, 2022 Response, dated Jul. 18, 2022, in the Munich Federal Patent Court, Nullity Suit 6 Ni 32/22.

Plaintiff's Response to Court Order disagreeing with Stay of Proceedings dated Oct. 28, 2022 in Mannheim District Court, Infringement suit 7 O 147/21.

Plaintiff's Technical Brief dated Sep. 29, 2022 in the Mannheim District Court, Infringement suit 7 O 147/21.

Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).

Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.

Prochnau, Dirk et al., Catheter-based renal denervation for drug-resistant hypertension by using a standard electrophysiology catheter, EuroIntervention, vol. 7, 1077-1080 (2012).

Pugsley, et al., The vascular system: An overview of structure and function, Journal of Pharmacological and Toxicological Methods 44 (2000) 333-340.

Purerfellner, Helmut et al., Incidence, Management and Outcome in Significant Pulmonary Vein Stenosis Complicating Ablation for Atrial Fibrillation, 93 Am. J. Cardiol. 1428 (2004).

Purerfellner, Helmut & Martinek, Martin, Pulmonary vein stenosis following catheter ablation of atrial fibrillation, 20 Curr. Opin. Cardiol. 484 (2005).

Reaz, M.B.I., et al., "Techniques of EMG signal analysis: detection, processing, classification and applications," Biological Procedures Online, Jan. 2006, 25 pages.

Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.

Romanes, G.J., Cunningham's Textbook of Anatomy (11th ed. 1972).

Ryan, Steve, What are the Risks Associated with a Pulmonary Vein Ablation Procedure?, Atrial Fibrillation: Resources for Patients (last accessed Oct. 18, 2022).

Ryan, Thomas et al., Proceedings of Thermal Treatment of Tissue with Image Guidance, Progress in Biomedical Optics, vol. 3594 (1999).

Ryan, Thomas P., Thermal Treatment of Tissue with Image Guidance; Ultrasound Catheters For Circumferential Cardiac Ablation 1999;.

Sakakura, Kenichi et al., Anatomic Assessment of Sympathetic Peri-Arterial Renal Nerves in Man, Journal of the American College of Cardiology, vol. 64, No. 7, 635-643 (2014).

Salmanpour, A., L. J. Brown and J. K. Shoemaker, "Detection of Single Action Potential in Multi- Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.

Sanchez-Quintana, Damian et al., How close are the phrenic nerves to cardiac structures? Implications for cardiac interventionalists, 16 J. Cardiovasc. Electrophysiol 309 (2005) ("Sánchez-Quintana").

Sato, Yu, et al., "Translational Value of Preclinical Models for Renal Denervation: a histological comparison of human versus porcine renal nerve anatomy," EuroIntervention, 18, e1120-e1128, 2023.

Schlaich, M.P. et al., "Renal Denervation: A Potential New Treatment Modality for Polycystic Ovary Syndrome," Journal of Hypertension, vol. 29, No. 5, pp. 991-996 201 1 . doi:10.1097/HJH. 0b013e328344db3a.

Schmieder, Ronald E., Renal denervation in patients with chronic kidney disease: current evidence and future perspectives, Nephrol. Dial. Transplant. gfac189 (2022).

Schneider, Peter, Endovascular Skills: Guidewire and Catheter Skills for Endovascular Surgery, 2nd ed., Marcel Dekker, Inc., New York, NY (2003).

Schneider, Peter A., Endovascular Skills, Quality Medical Publishing, Inc., 1998 ("Schneider").

Schmidt, Boris, et al., "Pulmonary Vein Isolation by High Intensity Focused Ultrasound," Indian Pacing and Electrophysiology Journal, pp. 126-133 (2006).

Selected documents from the File History of Inter Partes Reexamination U.S. Appl. No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Shimizu, Kazumasa et al., Sympathetic Dysfunction in Heart Failure, Bailliere's Clinical Endocrinology and Metabolism, vol. 7, No., 2 (1993).

Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").

Slide deck from Medtronic Circulatory System Devices Panel Meeting, General Issues Panel: Clinical Evaluation of Anti-Hyperintensive Devices (Dec. 5, 2018).

Smithwick, R. H., et al., "Splanchnicectomy for essential hypertension." J. Am. Med. Assoc., 152:1501-1504 (1953).

Stella, A., et al. "Effects of reversible renal denervation on haemodynamic and excretory functions of the ipsilateral and contralateral kidney in the cat." J Hypertension, 4: 181-188 (1986)("Stella").

Stipulation Modifying Schedule, dated Dec. 30, 2022 in the Patent Trial and Appeal Board, United States Patent and Trademark Office, Petition No. PTAB-IPR2022-00431.

Stipulation Modifying Schedule, dated Feb. 16, 2023 in the Patent Trial and Appeal Board, United States Patent and Trademark Office, Petition No. PTAB-IPR2022-00431.

Stoeckel, D. et al., A Survey of Stent Designs, Min Invas Ther & Allied Technol 2002: 11(4) 137-147 (2002).

Swartz, John F. et al., Radiofrequency Endocardial Catheter Ablation of Accessory Atrioventricular Pathway Atrial Insertion Sites, 87 Circulation 487 (1993).

(56)                    References Cited

OTHER PUBLICATIONS

Tank, J. et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07.012.

Tanaka, Kazushi et al., "A New Radiofrequency Thermal Balloon Catheter for Pulmonary Vein Isolation," Journal of the American College of Cardiology vol. 38, No. 7, 2001.

Teigen et al., Segmental Renal Artery Embolization for Treatment of Pediatric Renovascular Hypertension, J. Vasco Interv. Radiol. 3, 111-7 (1992).

Thatipelli, Mallik R., et al., CT angiography of renal artery anatomy for evaluating embolic protection devices, 18 J. Vasc. Interv. Radiol. 842 (2007).

The Doctors and Experts at WebMD, Webster's New World Medical Dictionary (3rd ed. 2008) ("WebsterMD").

Transcript of the Mar. 2, 2023 deposition of Dr. John Moriarty.

Transcript of the Mar. 3, 2023 deposition of Dr. Chris Daft.

Transcript of deposition of the Jan. 1, 2023 deposition of Dr. Robert Tucker.

Transcript of the Jan. 14, 2023 deposition of Dr. Daniel van der Weide.

Transcript of the Sep. 30, 2022 deposition of Dr. Chris Daft.

Transcript of the Oct. 1, 2022 deposition of Dr. Farrell Mendelsohn.

Tsao, Hsuan-Ming et al., Evaluation of Pulmonary Vein Stenosis after Catheter Ablation of Atrial Fibrillation, 6 Card. Electrophysiol. Rev. 397 (2002).

Turner, et al., "Initial Experience Using the Palmaz Corinthian Stent for Right Ventricular Outflow Obstruction in Infants and Small Children", Catheterization and Cardiovascular Interventions 51:444-449 (2000).

Uchida, et al., "Effect of radiofrequency catheter ablation on parasympathetic denervation: A comparison of three different ablation sites." PACE, 21 :2517- 2521 (1998).

Ulmsten, Ulf et al., "The Safety and Efficacy of Meno TreatTM, a new balloon device for thermal endometrial ablation," Acta Obstet Gynecol Scand 2001; 80: 52-57.

Vaezy, Shahram et al., Image-Guided Acoustic Therapy, Annual Review Biomedical Engineering, vol. 3, 375-390 (2001).

Valente, John F. et al., Laparoscopic renal denervation for intractable ADPKD-related pain, 16 Nephrol. Dial. Transplant. 160 (2001).

Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").

Wanchoo, Nishey, Medtronic Gets European and Australian Approval for Symplicity Spyral Multi-Electrode Renal Denervation Catheter, Medgadget (2013).

Weinstock, Marta et al., "Renal Denervation Prevents Sodium Retention and Hypertension in Salt- Sensitive Rabbits with Genetic Baroreflex Impairment", 90 Clinical Science 287 (1996).

Xu, J. et al., "A Bidirectional Neuromodulation Technology for Nerve Recording and Stimulation, Micromachines," vol. 9, 1 1 538. Oct. 23, 2018. doi:10.3390/mi9110538.

Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.

Zazgornik, "Bilateral Nephrectomy: The best, but often overlooked, treatment for refractory hypertension in hemodialysis patients," Am. J. Hypertension, 11:1364-1370 (1998).

Ziegler et al., Sources of Urinary Catecholamines in Renal Denervated Transplant Recipients, 8 J. Hypertension No. 10, 927 (1990).

U.S. Appl. No. 17/453,636, filed Nov. 4, 2021, File History.

U.S. Appl. No. 10/408,665, File History.

U.S. Appl. No. 60/624,793, File History.

U.S. Appl. No. 60/370,190, File History.

U.S. Appl. No. 60/415,575, File History.

U.S. Appl. No. 60/442,970, File History.

U.S. Appl. No. 60/616,254, File History.

U.S. Appl. No. 60/747,137, File History.

U.S. Appl. No. 60/808,306, File History.

U.S. Appl. No. 60/816,999, File History.

U.S. Appl. No. 61/405,472, File History.

U.S. Appl. No. 11/532,814, Non-Final Office Action mailed Mar. 29, 2012.

U.S. Appl. No. 14/683,966, Non-Final Office Action mailed Jun. 12, 2017, 14 pgs.

U.S. Appl. No. 14/683,966, Response filed Nov. 10, 2017 to Non-Final Office Action mailed Jun. 12, 2017, 13 pgs.

U.S. Appl. No. 14/683,966, Notice of Allowance mailed Jan. 31, 2018, 8 pgs.

U.S. Appl. No. 14/683,966, PTO Response to Rule 312 Communication mailed Mar. 29, 2018, 2 pgs.

U.S. Appl. No. 14/683,966, 312 Amendment filed Mar. 13, 2018, 10 pgs.

U.S. Appl. No. 14/683,966, Corrected Notice of Allowance mailed May 22, 2018, 4 pgs.

U.S. Appl. No. 15/204,349, Preliminary Amendment filed Nov. 30, 2016, 3 pgs.

U.S. Appl. No. 15/204,349, Restriction Requirement mailed May 17, 2018, 7 pgs.

U.S. Appl. No. 15/204,349, Response filed Jun. 5, 2018 to Restriction Requirement mailed May 17, 2018, 7 pgs.

U.S. Appl. No. 15/204,349, Non-Final Office Action mailed Nov. 27, 2018, 14 pgs.

U.S. Appl. No. 15/204,349, Response filed Feb. 27, 2019 to Non-Final Office Action mailed Nov. 27, 2018, 10 pgs.

U.S. Appl. No. 15/204,349, Final Office Action mailed Apr. 22, 2019, 16 pgs.

U.S. Appl. No. 15/204,349, Response filed Jun. 24, 2019 to Final Office Action mailed Apr. 22, 2019, 12 pgs.

U.S. Appl. No. 15/204,349, Advisory Action mailed Jul. 9, 2019, 5 pgs.

U.S. Appl. No. 15/261,732, Notice of Allowance dated Sep. 25, 2018.

U.S. Appl. No. 15/299,694, Restriction Requirement mailed Aug. 6, 2018, 6 pgs.

U.S. Appl. No. 15/299,694, Response filed Oct. 8, 2018 to Restriction Requirement mailed Aug. 6, 2018, 7 pgs.

U.S. Appl. No. 15/299,694, Non-Final Office Action mailed Nov. 27, 2018, 15 pgs.

U.S. Appl. No. 15/299,694, Response filed Feb. 27, 2019 to Non-Final Office Action mailed Nov. 27, 2018, 10 pgs.

U.S. Appl. No. 15/299,694, Final Office Action mailed Apr. 22, 2019, 16 pgs.

U.S. Appl. No. 15/299,694, Response filed Jun. 24, 2019 to Final Office Action mailed Apr. 22, 2019, 11 pgs.

U.S. Appl. No. 15/299,694, Advisory Action mailed Jul. 9, 2019, 5 pgs.

U.S. Appl. No. 15/943,354, Preliminary Amendment filed Apr. 3, 2018, 9 pgs.

U.S. Appl. No. 15/943,354, Restriction Requirement mailed Nov. 20, 2019, 8 pages.

U.S. Appl. No. 15/943,354, Response filed Dec. 19, 2019 to Restriction Requirement mailed Nov. 20, 2019, 8 pages.

U.S. Appl. No. 15/943,354, Non-Final Office Action mailed Jan. 13, 2020, 6 pages.

U.S. Appl. No. 15/943,354, Non-Final Office Action mailed Apr. 20, 2020, 7 pages.

U.S. Appl. No. 15/996,978, Preliminary Amendment filed Jun. 5, 2018, 11 pgs.

U.S. Appl. No. 15/996,978, Restriction Requirement mailed Feb. 7, 2020, 7 pages.

U.S. Appl. No. 15/996,978, Response filed Apr. 6, 2020 to Restriction Requirement mailed Feb. 7, 2020, 8 pages.

U.S. Appl. No. 15/996,978, Restriction Requirement mailed Apr. 16, 2020, 8 pages.

U.S. Appl. No. 15/996,978, Response filed May 1, 2020 to Restriction Requirement mailed Apr. 16, 2020, 8 pgs.

U.S. Appl. No. 15/996,978, Non-Final Office Action mailed Jun. 11, 2020, 8 pages.

(56)  References Cited

OTHER PUBLICATIONS

U.S. Appl. No. 16/219,874, Final Office Action mailed Dec. 21, 2020, 7 pages.
U.S. Appl. No. 16/517,180, Preliminary Amendment filed Jul. 19, 2019, 12 pgs.
U.S. Appl. No. 17/453,636, filed Nov. 4, 2021.
File History of U.S. Appl. No. 12/754,337.
File History to U.S. Pat. No. 9,943,666.
File History to U.S. Pat. No. 9,981, 108.
File History to U.S. Pat. No. 10,039,901.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-Final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.
Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.
Ahmed, Muneeb et al., "Thermal Ablation Therapy for Hepatocellular Carcinoma," J. Vasc. Interv, Radiol., vol. 13, No. 9 pt. 2, 2002.
Benito, Fernando et al., "Radiofrequency catheter ablation of accessory pathways in infants," Heart, vol. 78, p. 160-162, 1997.
Chang, Isaac A. et al., "Thermal Modeling of Lesion Growth with Radiofrequency Ablation Devices," Biomedical Engineering Online vol. 3, p. 27, 2004.
Chung, Andrew et al., "Thermal dosimetry of a focused ultrasound beam in vivo by magnetic resonance imaging," Medical Physics, vol. 26, No. 9, p. 2017-2026, Sep. 1999.
Damianou, Christakis et al., "High Intensity Focused Ultrasound Ablation of Kidney Guided MRI," Ultrasound in Med. & Biol., vol. 30, No. 3, p. 397-404, 2004.
Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170-178, Jan. 2000.
Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.
Diederich, Chris J. et al., "Ultrasound Technology for Hyperthermia," Ultrasound in Med. & Biol., vol. 25, No. 6, p. 871-887, 1999.
Fry, F.J. et al., "Production of Reversible Changes in the Central Nervous System by Ultrasound," Science, vol. 127, p. 83-84, Jan. 1958.
Gavrilov, L.R. et al., The Effect of Focused Ultrasound on the Skin and Deep Nerve Structures of Man and Animal, p. 279-292.
Gavrilov, L.R., "Use of Focused Ultrasound for Stimulation of Nerve Structures," Ultrasonics, p. 132-138, May 1984.
Graham, S.J. et al., "Quantifying Tissue Damage Due to Focused Ultrasound Heating Observed by MRI" Magnetic Resonance in Medicine vol. 41, p. 321-328, 1999.
Goldberg, S. Nahum et al., "Radiofrequency Tissue Ablation: Increased Lesion Diameter with a Perfusion Electrode," Acad. Radiol. Vol. 3, No. 8, p. 636-644, Aug. 1996.
Hacker, Axel et al., "Extracorporeal Organotripsy for Renal Tumours," Current Opinion in Urology, vol. 13, p. 221-225, 2003.
Hausberg, Martin et al., "Sympathetic Nerve Activity in End-Stage Renal Disease," Circulation, vol. 106, p. 1974-1979, 2002.
Ho, Siew Yen et al., "Anatomy of the Left Atrium: Implications for Radiofrequency Ablation of Atrial Fibrillation," J Cardiovasc Electrophysiol, vol. 10, p. 1525-1533, Nov. 1999.
Israel, Gary M. et al., "MRI of the Kidney and Urinary Tract," Journal of Magnetic Resonance Imaging, vol. 24, p. 725-734, 2006.

Jiang, S.C. et al., "Effects of Thermal Properties and Geometrical Dimensions on Skin Burn Injuries," Burns, vol. 28, p. 713-717, 2002.
Kaye, David M. et al., "Functional and Neurochemical Evidence for Partial Cardiac Sympathetic Reinnervation After Cardiac Transplantation in Humans," Circulation, vol. 88, No. 3, Sep. 1993.
Keane, David, "New Catheter Ablation Techniques for the Treatment of Cardiac Arrhythmias," Cardiac Electrophysiology Review vol. 6, No. 4, p. 341-348, 2002.
Kennedy, J.E. et al., "High Intensity Focused Ultrasound: Surgery of the Future?", The British Journal of Radiology, vol. 76, p. 590-599, Sep. 2003.
Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.
Lauder, Lucas et al., "Renal Denervation in the Management of Hypertension," EuroIntervention, vol. 20, pg. e467-e478, 2024.
Lele, P.P., "Effects of Focused Ultrasonic Radiation on Peripheral Nerve, with Observations on Local Heating," Experimental Neurology, vol. 8, p. 47-83, 1963.
Liao, Qingyao et al., "Optimal Strategy for HIFU-Based Renal Sympathetic Denervation in Canines," Frontiers in Cardiovascular Medicine vol. 8, p. 1-11, Oct. 2021.
Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.
Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.
Mahfoud, Felix et al., "Device Therapy of Hypertension," Circulation Research nol. 128, p. 1080-1099, Apr. 2021.
Makin, Inder Raj. S. et al., "Miniaturized Ultrasound Arrays for Interstitial Ablation and Imaging," Ultrasound in Med. & Biol. vol. 31, No. 11, p. 1539-1550, 2005.
Malcolm, A.L. et al., "Ablation of Tissue vols. Using High Intensity Focused Ultrasound" Ultrasound in Med. & Biol. vol. 22 No. 5 p. 659-669, 1996.
Manolis, Antonis S. et al., "Radiofrequency Catheter Ablation for Cardiac Tachyarrhythmias," Annals of Internal Medicine, vol. 131, No. 6, p. 452-461, Sep. 1994.
Mitchell, G.A.G et al., "An Anatomical Evaluation of Operations for Hypertension," Proceedings of the Anatomical Society vol. LIV., No. 10, p. 545-560.
Mompeo, Blanca et al., "The Gross Anatomy of the Renal Sympathetic Nerves Revisited," Clinical Anatomy vol. 29, p. 660-664, Apr. 2016.
Moore, J.H. et al., "The Biophysical Effects of Ultrasound on Median Nerve Distal Latencies," Electromyogr. Clin. Neurophysiol., vol. 40, p. 169-190, 2000.
Nath, Sunil et al., "Basic Aspects of Radiofrequency Catheter Ablation," Journal of Cardiovascular Electrophysiology vol. 5, No. 10, p. 863-876, Oct. 1994.
Nath, Sunil et al., "Biophysics and Pathology of Catheter Energy Delivery Systems," Progress in Cardiovascular Diseases, vol. XXXVII, No. 4, p. 185-204, January/Feb. 1995.
Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.
Nikfarjam, Mehrdad et al., "Mechanisms of Focal Heat Destruction of Liver Tumors," Journal of Surgical Research, vol. 127, No. 2, p. 208-223, Aug. 2005.
Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.
Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.

(56) References Cited

OTHER PUBLICATIONS

Papademetriou, Vasilios et al., "Renal Nerve Ablation for Resistant Hypertension, How Did We Get Here, Present Status, and Future Directions," Circulation, No. 129, p. 1440-1451, 2014.

Pozzoli, Alberto et al., "Electrophysiological Efficacy of Epicor High-Intensity Focused Ultrasound," European Journal of Cardio-Thoracic surgery, vol. 42, p. 129-134, 2012.

Riis, Thomas et al., "Effective Ultrasonic Stimulation in Human Peripheral Nervous System," IEE Transactions on Biomedical Engineering, vol. XX, No. XX, p. 1-8, XXXX 2021.

Roux, N et al., "The Myocardial Sleeves of the Pulmonary Veins: Potential Implications for Atrial Fibrillation," Surg. Radiol. Anat., vol. 26, p. 285-289, Feb. 2004.

Schuarte, Patrick et al., "Catheter Ablation of Cardiac Autonomic Nerves for Prevention of Vagal Atrial Fibrillation," Circulation vol. 102, p. 2774-2780, 2000.

Tellez, Armando et al., "Renal Artery Nerve Distribution and Density in the Porcine Model: Biologic Implications for the Development of Radiofrequency Ablation Therapies," Translational Research vol. 162 no.6, p. 381-389, Dec. 2013.

Ter Haar, G., "Ultrasound Focal Beam Surgery," Ultrasound in Med. & Biol., vol. 21, No. 9, p. 1089-1100, 1995.

Ter Haar, G.R. et al., "Ultrasonic Heating of Mammalian Tissues In vivo," Br. J. Cancer vol. 45, Supp. V., p. 65-67, 1982.

Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.

Trippodo, Nick C. et al., "Similarities of Genetic (Spontaneous) Hypertension," Circulation Research vol. 48, No. 3, p. 309-319, Mar. 1981.

Urban, Bruce A. et al., "Three-dimensional vol. rendered CT Angiography of the Renal Arteries and Veins: Normal Anatomy, Variants, and Clinical Applications," RG vol. 21 no. 2, p. 373-386, Mar.-Apr. 2001.

Wang, Shyh-Hau et al., "Effects of Low Intensity Ultrasound on the Conduction Property of Neural Tissues," IEEE International Ultrasonics, Ferroelectrics, and Frequency Control Joint 50th Anniversary Conference, p. 1824-1827, 2004.

Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.

Wells, P.N.T., "Functional Modification: Clinical Applications," Biomedical Ultrasonics, p. 470-504, 1977.

Winternitz, Sherry R. et al., "Importance of the Renal Nerves in the Pathogenesis of Experimental Hypertension," Hypertension (supp. III), vol. 4, No. 5, p. III-08-III-115, Sep.-Oct. 1982.

Wulff, V.J. et al., "Effects of Ultrasonic Vibrations on Nerve Tissues," P.S.E.B.M., vol. 76, p. 361-366, 1951.

Yarmolenko, Pavel S. et al., "Thresholds for thermal damage to normal tissues: An update," Int. J. Hyperthermia, vol. 27 No. 4, p. 320-343, Jun. 2011.

Young, Robert R. et al., "Functional Effects of Focused Ultrasound on Mammalian Nerves," Science, vol. 134, p. 1521-1522, Nov. 1961.

Zimmer, J.E. et al., "The Feasibility of Using Ultrasound for Cardiac Ablation," IEEE Transactions on Biomedical Engineering, vol. 42, No. 9, p. 891-897, Sep. 1995.

Wang, Paul J., "Overview of Balloon Approaches to AF Ablation," Journal of the American College of Cardiology, vol. 68, No. 25, 2016.

Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.

Calkins, Hugh et al., "Temperature Monitoring During Radiofrequency Catheter Ablation Procedures Using Closed Loop Control," Circulation vol. 90, No. 3, p. 1279-1286, Sep. 1994.

Deardorff, Dana L. et al., "Control of interstitial thermal coagulation: Comparative evaluation of microwave and ultrasound applicators," Medical Physics vol. 28, No. 1, p. 104-117, Jan. 2001.

Dinerman, Jay L. et al., "Temperature Monitoring During Radiofrequency Ablation," Journal of Cardiovascular Electrophysiology, vol. 7 No. 2, p. 163-173, Feb. 1996.

Esler, Murray et al., "The future of renal denervation," Autonomic Neuroscience: Basic and Clinical, vol. 204, p. 131-138, May 2017.

Filonenko, E.A. et al., "Heating of Biological Tissues by Two-Dimensional Phased Arrays with Random and Regular Element Distributions," Acoustical Physics, vol. 50 No. 2, p. 222-231, 2004.

Fry, William J., "Action of Ultrasound on Nerve Tissue-A review," The Journal of the Acoustical Society of America, vol. 25 No. 1, p. 1-5, Jan. 1953.

Fry, Frank J., "Precision High Intensity Focusing Ultrasonic Machines for Surgery," High Intensity Focused U.S., 152-156, Sep. 6-7, 1957.

Haines, David, "Biophysics of Ablation: Application to Technology," Journal of Cardiovascular Electrophysiology, vol. 15, No. 10, pg. S2-S11, Oct. 2004.

Hynynen, K. et al., "Design of Ultrasonic Transducers for Local Hyperthermia," Ultrasound in Med. & Biol., vol. 7, No. 4, p. 397-402, Feb. 1981.

Hynynen, K. et al., "Temperature measurements during ultrasound hyperthermia," Medical Physics vol. 16, No. 4, p. 618-626, Jul./Aug. 1989.

Jolesz, Ferenc A. et al., "MR Imaging-Controlled Focused Ultrasound Ablation: A Noninvasive Image-Guided Surgery," Magnetic Resonance Imaging Clinics of North America, vol. 13, Issue 3, p. 545-560, 2005.

Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.

Lafon, C. et al., "Design and Preliminary Results of an Ultrasound Applicator for Interstitial Thermal Coagulation," Ultrasound in Medicine & Biology, vol. 24, No. 1, p. 113-122, 1998.

Lewis, Matthew A. et al., "Thermometry and Ablation Monitoring with Ultrasound," Int. J. Hyperthermia vol. 31, Issue 2, p. 163-181, Mar. 2015.

Liu, Xinmeng et al., "Visualization and mapping of the right phrenic nerve by intracardiac echocardiography during atrial fibrillation ablation," Europace vol. 25, p. 1352-1360, 2023.

Mendelsohn, Farrell O., "Microanatomy of the Renal Sympathetic Nervous System," Endovascular Today, p. 59- 62, Oct. 2013.

Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.

Quadri, Syed A. et al., "High-intensity focused ultrasound: past, present, and future in neurosurgery," Neurosurgical Focus, vol. 44, No. 2, p. 1-9, Feb. 2018.

Ross, Anthony B. et al., "Highly directional transurethral ultrasound applicators with rotational control for MRI-guided prostatic thermal therapy," Physics in Medicine & Biology, vol. 49, p. 189-204, Jan. 2004.

Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.

Sanghvi, Kintur et al., "Rationale and design for studies of renal denervation in the absence (SPYRAL HTN OFF-MED) and presence (SPYRAL HTN ON-MED) of antihypertensive medications," American Heart Journal, vol. 180, p. e1-e2. Oct. 2016.

Satou, Shunsuke et al., "Observation of renal sympathetic nerves by intravascular ultrasound," Hypertension Research vol. 42, p. 1092-1094, 2019.

Schmidt, Boris et al., "Balloon Catheters for Pulmonary Vein Isolation," Herz vol. 33, p. 580-584, 2008.

Smith, Nadine Barrie et al., "Transrectal Ultrasound Applicator for Prostate Heating Monitored Using MRI Thermometry," Int. J. Radiation Oncology Biol. Phys. Vol. 43, No. 1, p. 217-225, 1998.

Stauffer, P.R. et al., "13 Interstitial Heating Technologies," Thermoradiotherapy and Thermochemotherapy, p. 279-320, 1995.

Swanson, David K. et al., "Tissue temperature Feedback Control of Power, The Key to Successful Ablation," Innovations, vol. 6 No. 4, p. 276-282, Jul./Aug. 2011.

(56)  References Cited

OTHER PUBLICATIONS

Tabei, Makoto et al., "A k-space method for coupled first-order acoustic propagation equations," J. Acoust. Soc. Am., vol. 111, No. 1, pt. 1, p. 53-63, Jan. 2002.

Tzafriri, Abraham R. et al., "Innervation Patterns May Limit Response to Endovascular Renal Denervation," Journal of the American College of Cardiology, vol. 64, No. 11, p. 1079-1087, Sep. 2014.

Umemura, Shin-ichiro, "Focused ultrasound transducer for thermal treatment," International Journal of Hyperthermia, vol. 31, No. 2, p. 216-221, 2015.

Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.

Zivin, Adam, et al., "Temperature Monitoring versus Impedance Monitoring during RF Catheter Ablation," Radiofrequency Catheter Ablation of Cardiac Arrhythmias, Basic Concepts and Clinical.

Applications, Second Edition, Edited by Shoei K. Stephen Huang, MD & David J. Wilber, MD, p. 103-112, 2000.

\* cited by examiner

2402

2402

TREATMENT SYSTEM HAVING GENERATOR AND FLUID TRANSFER CARTRIDGE

This application claims the benefit of priority under 35 U.S.C. § 119(e) to U.S. Provisional Application No. 63/223,518, filed on Jul. 19, 2021 titled TREATMENT SYSTEM HAVING GENERATOR AND FLUID TRANSFER CARTRIDGE, U.S. Provisional Patent Application No. 63/287,358, filed on Dec. 8, 2021 titled TREATMENT SYSTEM HAVING GENERATOR AND FLUID TRANSFER CARTRIDGE, U.S. Provisional Patent Application No. 63/367,013, filed on Jun. 24, 2022 titled TREATMENT SYSTEM HAVING GENERATOR AND FLUID TRANSFER CARTRIDGE, and U.S. Provisional Patent Application No. 63/367,015, filed on Jun. 24, 2022 titled, TREATMENT SYSTEM HAVING GENERATOR AND FLUID TRANSFER CARTRIDGE, which are incorporated herein by reference in their entirety to provide continuity of disclosure.

BACKGROUND

Field

This application relates generally to medical systems used to deliver energy and fluid to a device, and more particularly, to a treatment system having a generator to deliver energy and a fluid transfer cartridge to deliver cooling fluid to a catheter-based intraluminal device.

Background Information

High blood pressure, also known as hypertension, commonly affects adults. Left untreated, hypertension can result in renal disease, arrhythmias, and heart failure. In recent years, the treatment of hypertension has focused on interventional approaches to inactivate the renal nerves surrounding a renal artery. Autonomic nerves tend to follow blood vessels to the organs that they innervate. Intraluminal devices, such as catheters, may reach specific structures, such as the renal nerves, that are proximate to the lumens in which the catheters travel. Accordingly, catheter-based systems can deliver energy from within the lumens to inactivate the renal nerves in the vessel walls.

One approach to renal nerve deactivation uses radio frequency (RF) energy. The RF energy is delivered to a catheter having multiple electrodes placed against the intima of the renal artery to create an electrical field in the vessel wall and surrounding tissue. The electrical field results in resistive (ohmic) heating of the tissue to ablate the tissue and the renal nerve passing through that tissue. To treat all the renal nerves surrounding the renal arteries, the RF electrodes are repositioned several times around the inside of the renal artery.

Another approach to renal nerve deactivation uses high-intensity focused ultrasound (HIFU). HIFU relies on the delivery of vibrational energy to a catheter to cause frictional heating and disruption of tissue. In turn, a temperature of the tissue elevates sufficiently to cause ablation or remodeling of the tissue containing the renal nerves. However, the use of HIFU intravascularly may result in, at most, the formation of a thin focal ring in the vessel and surrounding tissue. If applied to renal denervation, it would be difficult to align this thin ring with the renal nerves because the renal nerves lie at differing radial distances along the length of the renal arteries. Also problematic is that the thin focal ring results in a small longitudinal treatment zone relative to the axis of the vessel Many of the problems associated with RF and HIFU systems are solved by a system having an ultrasound transducer that emits one or more therapeutic doses of unfocused ultrasound energy. The ultrasound transducer can be mounted at a distal end of catheter, and the unfocused ultrasound energy can heat tissue adjacent to a body lumen within which the catheter (and the transducer) is disposed. Such unfocused ultrasound energy may, for example, ablate target nerves surrounding the body lumen, without damaging non-target tissue such as the inner lining of the body lumen or unintended organs outside of the body lumen. The unfocused ultrasound energy system may also include a balloon mounted at the distal end of the catheter around the ultrasound transducer. A cooling fluid can be circulated through the balloon to cool the body lumen during ultrasound energy delivery. Such a design enables creation of one or more ablation zones sufficient to achieve long-term nerve inactivation at different locations around the circumference of the blood vessel.

SUMMARY

The present invention is defined in the independent claims. Further embodiments of the invention are defined in the dependent claims.

A treatment system having a generator and a fluid transfer cartridge for delivering energy and/or fluid to a catheter-based intraluminal device is provided herein. In an embodiment, the fluid transfer cartridge includes a cartridge shell having a cartridge cavity. The cartridge cavity is between a front face and a rear face. A syringe barrel is disposed within the cartridge cavity, and has a syringe cavity. The fluid transfer cartridge includes a cartridge manifold in the cartridge cavity. The cartridge manifold includes a fluid transfer plate having a front fluid channel in a front plate surface, and a rear fluid channel in a rear plate surface. The cartridge manifold includes a fluid port extending through the fluid transfer plate from the front fluid channel to the rear fluid channel. The front fluid channel, the rear fluid channel, and the fluid port are in fluid communication with the syringe cavity.

A cartridge manifold is provided herein. The cartridge manifold includes a fluid transfer plate having a front fluid channel in a front plate surface, a rear fluid channel in a rear plate surface, and a fluid port extending through the fluid transfer plate from the front fluid channel to the rear fluid channel. The cartridge manifold includes a piston having an end seal. The piston is movable from an open position in which the end seal unseals the fluid port to allow cooling fluid to pass through the fluid port to a closed position in which the end seal seals the fluid port to stop the cooling fluid from passing through the fluid port.

The above summary does not include an exhaustive list of all aspects of the present invention. It is contemplated that the invention can be practiced from all suitable combinations of the various aspects summarized above, as well as those disclosed in the Detailed Description below and particularly pointed out in the claims. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Figure 1:
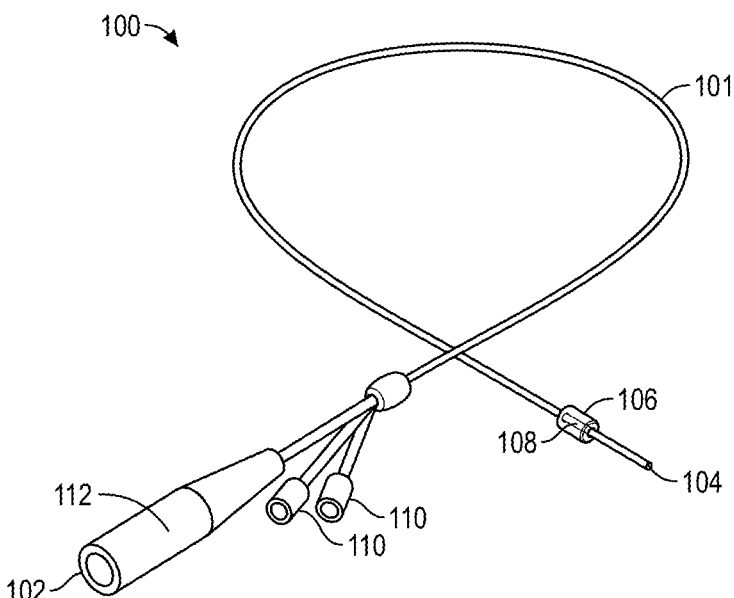
FIG. 1 is a perspective view of a catheter of a treatment system, in accordance with an embodiment.

Embodiments describe a treatment system having a generator and a fluid transfer cartridge, and methods of using the treatment system. The treatment system may be an ultrasound-based tissue treatment system, used to delivery unfocused ultrasonic energy radially outwardly to treat tissue within a target anatomical region, such as the renal nerves within a renal artery. Alternatively, the tissue treatment system may be used in other applications, such as to treat sympathetic nerves of the hepatic plexus within a hepatic artery. Thus, reference to the system as being a renal denervation system, or being used in treating, e.g., neuromodulating, renal nerve tissue is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "above" may indicate a first direction relative to a component. Similarly, "below" may indicate a second direction relative to the component, opposite to the first direction. Such terms are provided to establish relative frames of reference, however, and are not intended to limit the use or orientation of treatment system components, e.g., a fluid transfer cartridge or a generator, to a specific configuration described in the various embodiments below.

Existing hypertension treatment systems include generators to generate and deliver energy, e.g., RF or ultrasound energy, to a catheter-based intraluminal device. The treatment systems may also include components that engage with the generators to facilitate treatment. For example, cartridges may mount on the generators to deliver inflation or cooling fluid to a balloon mounted on an end of a catheter. The generator and/or cartridge may be large and bulky, especially in combination. Furthermore, mechanical and electrical connections between the generator and cartridge can be unreliable due to imperfect mounting, tolerance stack ups, or movement that occurs between the components during operation. In the case of cartridges that deliver fluids, the fluid transfer may not be accurately monitored either visually or automatically due to a lack of lighting in the procedure room and/or unstable sensor connections between the generator and the cartridge. The system may also integrate long lengths of internal tubing that increases an overall form factor of the equipment. Accordingly, treatment systems used to deliver energy and fluid to a catheter-based intraluminal device would benefit from more compact, mechanically stable, electrically stable, and ergonomic designs.

In an aspect, a treatment system for performing a medical procedure, e.g., a renal ablation catheterization, is provided. The treatment system includes a fluid transfer cartridge to deliver fluid to a catheter, and a generator to deliver energy to the catheter. The fluid transfer cartridge and the generator combine to form a control unit of the treatment system. The control unit is compact. More particularly, the fluid transfer cartridge fits within a cartridge receptacle of the generator to form a clean and compact profile of the control unit. Furthermore, the fluid transfer cartridge has syringe components that can be fully contained within a cartridge housing to reduce an overall form factor of the control unit. The control unit is mechanically stable. The fluid transfer cartridge can be fastened to the generator by a fastening mechanism that evenly distributes a retention force around the cartridge housing, and which has a quick release mechanism to make engagement and disengagement of the components fast and reliable. The control unit is electrically stable. Electrical connections between the fluid transfer cartridge and the generator may be via spring-loaded electrical contact pins, commonly referred to as pogo pins. The spring-loaded pins can maintain pressure at the electrical contact points between the components such that the connections are resilient against relative movement that can occur during operation. Furthermore, sensors used to detect movement of system components, such as a syringe piston of the fluid transfer cartridge, may include position sensors, such as magnetic switches or optical sensors, that are more stable and less susceptible to misalignment than, for example, mechanical switches. The control unit is user-friendly. The control unit can include one or more processors and various sensors that operate to determine a system readiness state, e.g., whether various electrical or component connections have been made, and to provide feedback to a user. By way of example, the system can detect whether the fluid transfer cartridge is mounted in the cartridge receptacle of the generator, and activate lights within the fluid transfer cartridge to illuminate the syringes to provide feedback about that state to the user. Accordingly, a treatment system having a compact, mechanically stable, electrically stable, and ergonomic design is provided.

Referring to FIG. 1, a perspective view of a catheter-based intraluminal device of a treatment system is shown in accordance with an embodiment. The catheter-based intraluminal device of a treatment system 100 can include a catheter 101 having an elongated catheter body extending from a proximal catheter end 102 to a distal catheter end 104. An expandable member 106, such as a balloon, may be mounted on the catheter 101 at the distal catheter end 104. One or more energy transducers 108, such as ultrasound transducers, may be positioned within the expandable member 106. The expandable member 106 can be adapted to inflate within a target anatomy, e.g., a renal artery, and the energy transducer 108 can be adapted to deliver ablation energy, e.g., ultrasound energy, to the target anatomy during a medical procedure, e.g., a renal denervation procedure.

The catheter 101 can include one or more lumens, such as: fluid lumens to deliver an inflation/cooling fluid to the expandable member 106, electrical cable passageways containing electrical cables to deliver energy to the transducer 108, guidewire lumens for exchanging guidewires, etc. The lumen(s) may be connected to corresponding connectors at the proximal catheter end 102. For example, the fluid lumens may connect to one or more fluid ports 110, which receive inflation/cooling fluid from a fluid transfer cartridge of the treatment system 100, as described below. Similarly, the electrical cables can connect to an external connector 112, which receives energy from a generator of the treatment system 100, as described below.

Figure 2:
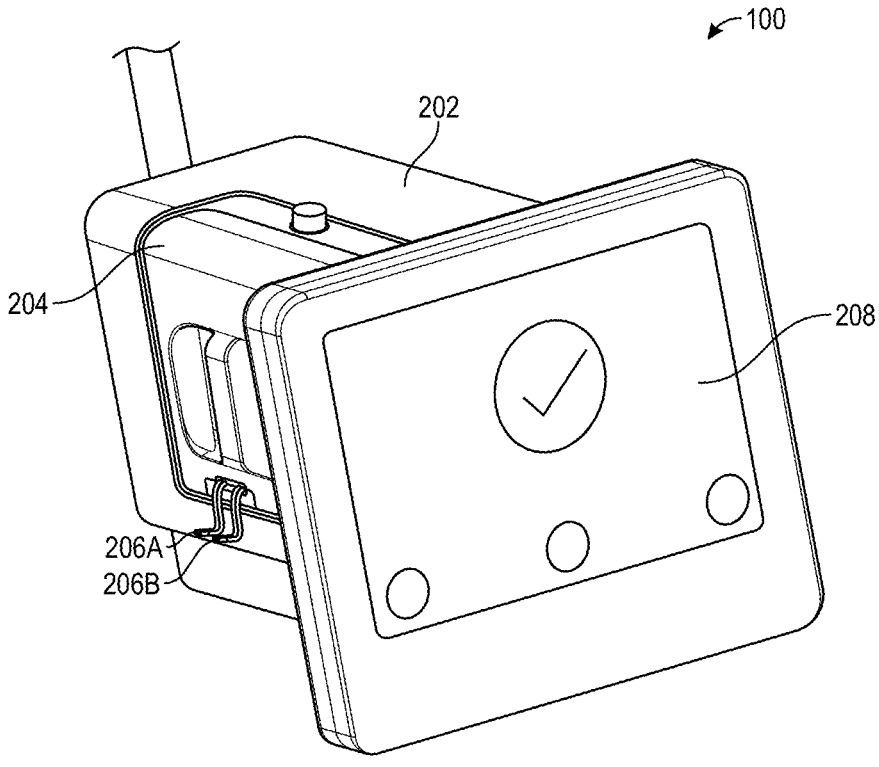
FIG. 2 is a front perspective view of a generator and a fluid transfer cartridge of a treatment system, in accordance with an embodiment.

Referring to FIG. 2, a front perspective view of a generator and a fluid transfer cartridge of a treatment system is shown in accordance with an embodiment. The treatment system 100 includes a control unit that connects to the catheter 101 to regulate the inflation of the balloon 106 with inflation/cooling fluid and to manage the delivery of ultrasound energy to the transducer 108. In an embodiment, the control unit includes a generator 202 to generate the ultrasound energy, and a fluid transfer cartridge 204 to transfer cooling fluid to and from the balloon 106 through one or more fluid conduits 206. For example, a fluid conduit 206A may transfer cooling fluid between a fluid reservoir, e.g., an intravascular fluid bag, and the fluid transfer cartridge 204. Similarly, a fluid conduit 206B can transfer cooling fluid between the fluid transfer cartridge 204 and the catheter 101. The control unit includes several other components, some of which are described below, to facilitate the energy and fluid transfer functions. Such components can include a display 208 to present procedural information to a user. Furthermore, the control unit can include one or more processors (not shown) configured to execute instructions stored in a memory device (not shown) to cause the treatment system 100 to perform various operations of the medical procedure, as described below.

Figure 3:
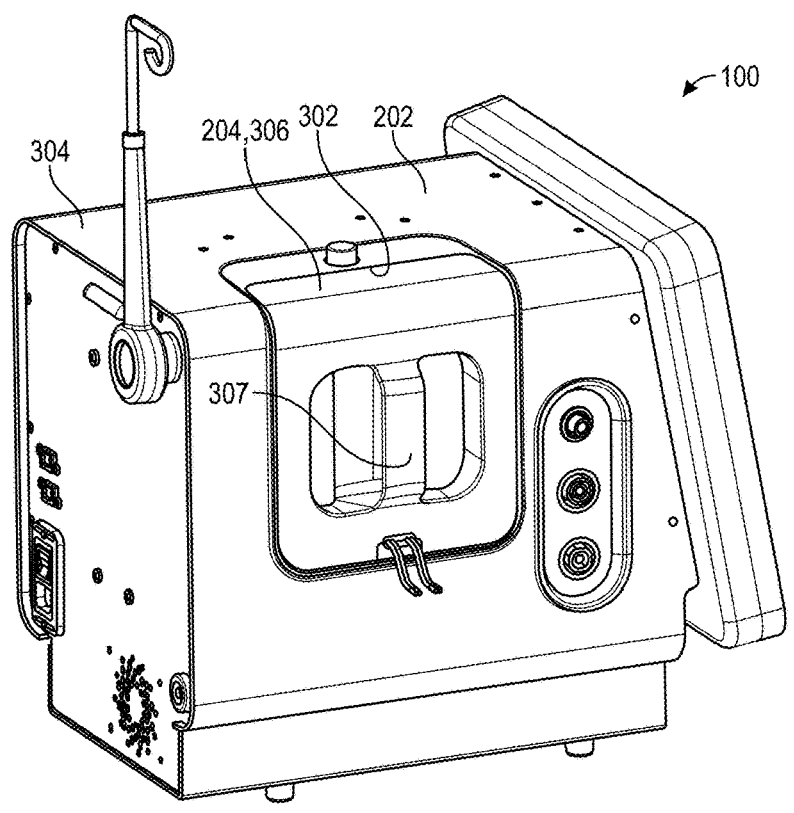
FIG. 3 is a rear perspective view of a generator and a fluid transfer cartridge of a treatment system, in accordance with an embodiment.

Referring to FIG. 3, a rear perspective view of a generator and a fluid transfer cartridge of a treatment system is shown in accordance with an embodiment. The generator 202 of the treatment system 100 can have a cartridge receptacle 302 shaped and sized to receive the fluid transfer cartridge 204. More particularly, the generator 202 can include a generator housing 304 having the cartridge receptacle 302 configured to receive the fluid transfer cartridge 204. The generator housing 304 can include an external wall having a shape, e.g., a box-like envelope, and the cartridge receptacle 302 may be a recessed region extending into the shape. The fluid transfer cartridge 204 can include a cartridge shell 306, which may fill the cartridge receptacle 302 of the generator 202. More particularly, the cartridge shell 306 can include an external wall having a shape that merges smoothly with the generator housing wall to complete the envelope of the generator 202. For example, the fluid transfer cartridge 204 and the generator 202 can combine to form the box-like envelope. In such case, the external, outward-facing surfaces of the fluid transfer cartridge 204 and generator 202 can be parallel and coplanar at a seam where the components meets such that the form factor of the combined components transitions smoothly, e.g., non-stepped, at the transition between the generator wall and the fluid transfer cartridge wall.

In an embodiment, the fluid transfer cartridge 204 includes a handle 307 that the user can hold when mounting or dismounting the cartridge from the generator 202. The handle 307 can include a curved, ergonomic shape that is easily grasped. Accordingly, the user can carry the fluid transfer cartridge 204 by the handle 307, and insert the fluid transfer cartridge 204 into the cartridge receptacle 302 to engage the components in the compact form factor having an external wall that extends continuously over the generator housing 304 and the cartridge shell 306.

In combination with the generator 202, the fluid transfer cartridge 204 can be used to drive fluid into the catheter 101 using one or more syringes. More particularly, the fluid transfer cartridge 204 can include one or more syringes that pump fluid to and from the balloon 106. As described below, each syringe can include a respective syringe piston disposed within a respective syringe barrel. Movement of the syringe piston relative to the syringe barrel can draw cooling fluid into the syringe or expel cooling fluid out of the syringe. The fluid can be transferred to and from the fluid transfer cartridge 204 through fluid conduits 206 that may be connected to a catheter 101, a fluid reservoir, or another fluid vessel external to the fluid transfer cartridge 204.

Figure 4:
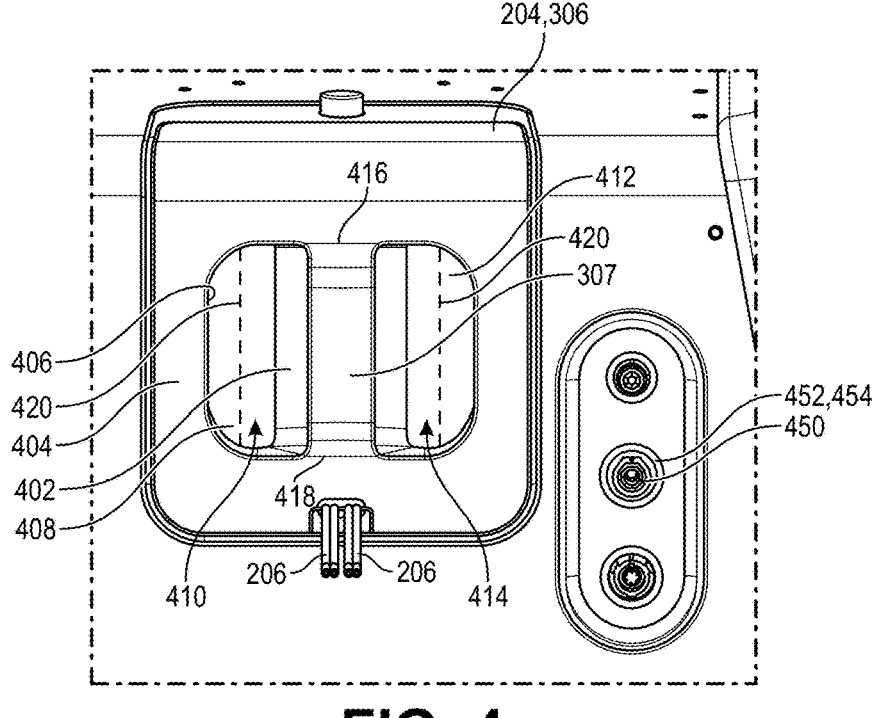
FIG. 4 is a perspective view of a cartridge receiving portion of a generator and a fluid transfer cartridge of a treatment system, in accordance with an embodiment.

Referring to FIG. 4, a perspective view of a cartridge receiving portion of a generator and a fluid transfer cartridge of a treatment system is shown in accordance with an embodiment. The cartridge shell 306 of the fluid transfer cartridge 204 can define a cartridge cavity 402 within which the one or more syringes are disposed. More particularly, the cartridge shell 306 can define the cartridge cavity 402 between a front face 404 of the cartridge shell 306, and a rear face 407 (FIG. 8) of the cartridge shell 306. A space between the front and rear faces 404, 407 of the cartridge shell 306 can contain the syringe(s). Accordingly, the syringes (including the syringe shafts of the syringes) may be stored internal to the cartridge shell 306, rather than being exposed outward from the shell. Thus, the overall form factor of the fluid transfer cartridge 204 may be compacted. The cartridge cavity 402 may further be defined between an upper face and a bottom face of the cartridge shell 306.

The one or more syringes of the fluid transfer cartridge 204 can be disposed within the cartridge cavity 402 parallel to the handle 307. For example, the handle 307 can extend from the front face 404 of the cartridge shell 306 over an opening that opens into the cartridge cavity 402. The opening can be a window 406 or a portal that exposes an internal volume of the cartridge cavity 402 to view from the surrounding environment. More particularly, the front face 404 can include the opening that visibly exposes the cartridge cavity 402 to view by the user. The handle 307 can extend vertically from an upper end 416 of the opening to a lower end 418 of the opening. Accordingly, the handle 307 can curve outward from the front face 404 above the opening, and vertically downward over the opening, to terminate at the front face 404 below the opening. Likewise, the syringe (s) can extend vertically through the cartridge cavity 402 such that the syringe barrels are visibly exposed through the opening.

In an embodiment, the fluid transfer cartridge 204 includes a first syringe barrel 408 within the cartridge cavity 402 and visibly exposed through the opening on a first side 410 of the handle 307. Similarly, the fluid transfer cartridge 204 can include a second syringe barrel 412 disposed within the cartridge cavity 402 and visibly exposed through the opening on a second side 414 of the handle 307. The syringes, like the handle 307, may extend vertically, e.g., within the cartridge cavity 402. More particularly, the first syringe barrel 408 and the second syringe barrel 412 can have respective syringe axes 420 that extend vertically, e.g., within the cartridge cavity 402. The syringe axes 420 can be central axes of the syringe barrels. For example, the syringe barrels may be cylindrical and may extend along the syringe axis 420 in a vertical direction. Accordingly, the handle 307 may be easily grasped from the front of the fluid transfer cartridge 204, however, the syringes may remain exposed to view through the opening in the front face 404. Thus, the fluid transfer cartridge 204 is easy to handle, easy to view, and has a compact form factor that meshes with the generator 202.

Figure 5:
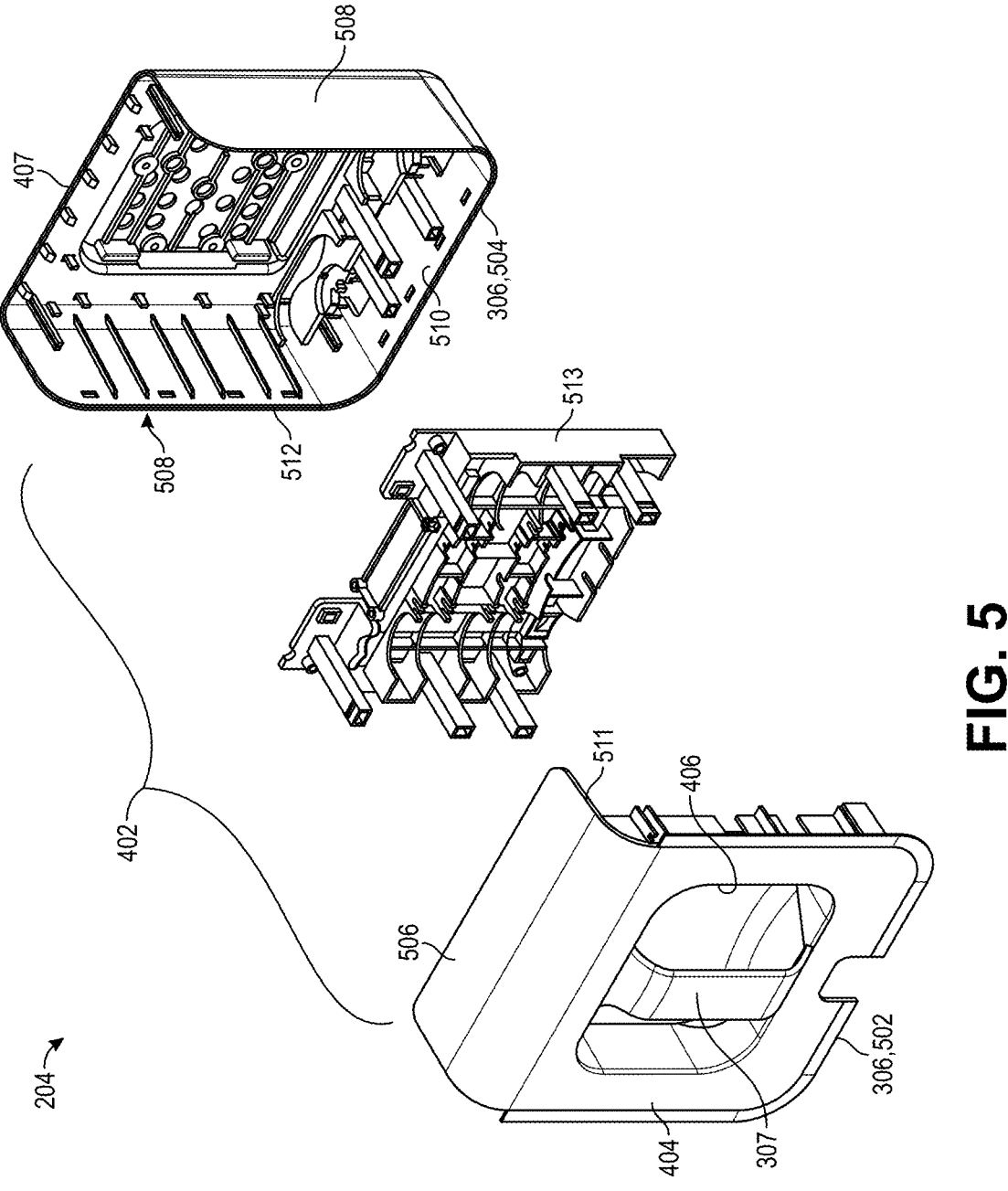
FIG. 5 is an exploded view of a cartridge shell of a fluid transfer cartridge, in accordance with an embodiment.

Referring to FIG. 5, an exploded view of a cartridge shell of a fluid transfer cartridge is shown in accordance with an embodiment. The cartridge shell 306 provides an external envelope of the fluid transfer cartridge 204 and can have a variety of geometries.

The fluid transfer cartridge 204 can include several portions that are snap-fit or otherwise fastened together. The cartridge shell 306 may include a handle front plate 502 and a back plate 504. The handle front plate 502 can include the handle 307, the front face 404 of the shell, and an upper face 506 of the shell. Similarly, the back plate 504 can include the rear face 407 of the shell, several sidewalls 508 laterally outward from the cartridge cavity 402, and a bottom face 510 of the shell. When combined, the handle front plate 502 and the back plate 504 can define the cartridge cavity 402 centrally located between the various walls and faces. As described above, the cartridge cavity 402 may nonetheless be visibly exposed through the opening 406 in the handle front plate 502.

The front face 404 can include a front face perimeter 511. The front face perimeter 511 can be an outer edge of the front face 404. The front face perimeter 511 can have curved and straight edges that combine to form an outline of the front face 404. Similarly, the rear face 407 can include a rear face perimeter 512. The rear face perimeter 512 can have curved and straight edges that combine to form an outline of the rear face 407. In an embodiment, the front face perimeter 511 has a same profile as the rear face perimeter 512. More particularly, an outline of the front face perimeter 511 can conform to an outline of the rear face perimeter 512 such that, when the front face perimeter 511 is engaged to the rear face perimeter 512, the perimeters effectively seal or contact each other. When the perimeters are in contact, the cartridge cavity 402 can be enclosed within the cartridge shell 306. The enclosed cartridge cavity 402 is defined between the front face 404 and the rear face 407.

When snapped or otherwise fit together, the handle front plate 502 and the back plate 504 can contain, within the cartridge cavity 402, one or more components to provide fluid transfer functionality. For example, the fluid transfer cartridge 204 can include a syringe holder 513 to hold the syringes within the cartridge cavity 402. The syringe holder 513 can stabilize the syringes during fluid delivery, as described below. The fluid transfer cartridge 204 can also include a manifold, tubing, electronics, etc. (not shown) that facilitate the movement of fluid from the syringes to the fluid conduits 206 and the catheter 101. The internal components of the fluid transfer cartridge 204 can be constrained within the internal space of the cartridge shell 306 and can interact mechanically and/or electrically with each other and with the generator 202 to perform the fluid transfer function of delivering inflation/cooling fluid to the fluid ports 110 of the catheter 101.

In an embodiment, the syringe holder 513, which is mounted within the cartridge cavity 402, limits movement of the syringe. The syringe may have a plunger that is driven axially within the syringe barrel 408 during operation. The plunger may rotate about the syringe axis 420, and thus, may impart some rotational loads to the syringe. The syringe holder 513 can resist rotation of the barrel that may otherwise be caused by the plunger. The syringe holder 513 can include one or more stop features. The stop features can be ribs, protrusions, or other features formed in the syringe holder 513. Stop features may remain fixed relative to the front and rear faces 404, 407 of the fluid transfer cartridge 204 when the cartridge is assembled. Furthermore, when assembled, a portion of the syringe barrel 408, such as a tab extending laterally outward from the cylindrical syringe barrel 408, can engage the stop feature. For example, the syringe barrel 408 can have finger tabs that are fit into a corresponding recess of the syringe holder 513. The finger tabs may be nestled within the recess between several ridges such that the syringe holder 513 mechanically interferes with movement of the tabs. Accordingly, the stop feature engages the interference feature of the syringe barrel 408 such that rotation of the syringe barrel 408 relative to the cartridge shell 306 is limited.

Figure 6:
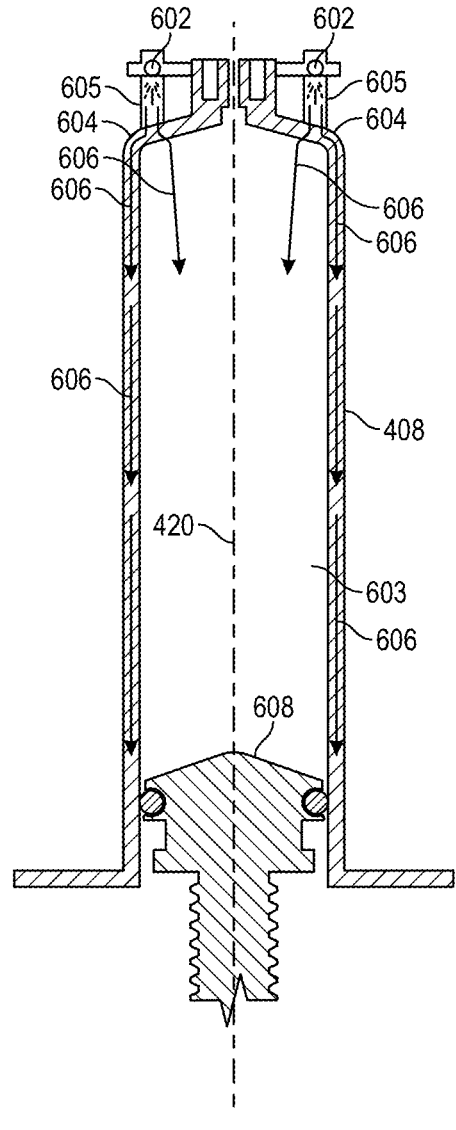
FIG. 6 is a sectional view of an end-lit syringe of a fluid transfer cartridge, in accordance with an embodiment.

Referring to FIG. 6, a sectional view of an end-lit syringe of a fluid transfer cartridge is shown in accordance with an embodiment. The fluid transfer cartridge 204 can include one or more light sources 602 within the cartridge cavity 402. For example, the light source(s) 602 can be light emitting diodes. As illustrated, two light sources 602 may be symmetrically located on each side of the syringe axis 420. Alternatively, three or more light sources 602 could be symmetrically disposed around the syringe axis 420. More particularly, when viewed from above, an angle between the light sources 602 may be 360° divided by the number of light sources 602 (e.g., 120° between each of the three light sources 602 when viewed along the syringe axis 420).

The light source 602 can illuminate one or more of the syringes such that the syringe barrel 408 and/or a cooling fluid 603 within the syringe can be seen by the user. More particularly, the light source 602 can be within the cartridge cavity 402, and can be directed through the syringe barrel 408 to illuminate the syringe barrel 408 contents and/or the wall of the syringe barrel 408. When the light source 602 is activated the user may look through the opening/window 406 in the fluid transfer cartridge 204 to see the syringe and cooling fluid operation. It will be appreciated that, especially when viewed within a dark procedure room, the light source 602 allows for easier monitoring of fluid transfer and troubleshooting of cooling fluid issues.

In an embodiment, the light source 602 is directed through the syringe barrel 408. For example, the syringe can be end-lit by the light source 602. Each of the one or more light sources 602 can direct light 606 into a respective light guide 605. The light guides 605 can include cylindrical transparent columns that act as light pipes to convey light 606 from the light source 602 to a distal (upper) end of the syringe. More particularly, the light source 602 may be directed through an end face 604 of the syringe barrel 408. The end face 604 can be a section of the barrel that is angled or tapered toward the syringe axis 420 from the substantially cylindrical side wall of the syringe barrel 408. Accordingly, an axis directed normal to the end face 604 outer surface may form an angle with the syringe axis 420 that is less than an angle formed between the syringe axis 420 and an axis normal to the barrel side wall.

The syringe may be side-lit by the light source 602. For example, rather than shining longitudinally into the syringe, the light source 602 may be directed in a transverse or radial direction relative to the syringe axis 420. Accordingly, the light 606 can illuminate the syringe barrel 408 and its contents from an end, side, or rear of the cartridge cavity 402.

In certain embodiments, the light source 602 may be directed through the syringe barrel 408 in order to help with assembly.

Light 606 can be emitted in a direction of the syringe axis 420. Accordingly, a portion of the light 606 can transmit through the end face 604 into the syringe barrel 408 and the fluid contained within. Furthermore, a portion of the light 606 can transmit into a wall of the syringe barrel 408. The light 606 can propagate along the wall creating a light pipe effect. The end-lit syringe barrel 408 can therefore provide good contrast against the fluid and mechanical components, e.g., a stopper 608, of the syringe. Accordingly, the light source 602 makes it easier to see syringe movement and otherwise visualize the function of the syringe during the medical procedure.

The light source 602 may have visible characteristics that are ergonomic. In an embodiment, the light source 602 emits a blue light. More particularly, a wavelength of the light 606 emitted by the light source 602 can be in the visible blue range. In a dark procedure room, the blue light can have a cool and calming effect. Furthermore, the blue light can have an intensity that is not distracting to the user, yet adequately lights the cooling fluid 603 for accurate monitoring.

In addition to illuminating the syringe components, the light source 602 may have visible characteristics that provide cues and visual feedback to the user. The control unit includes one or more processors configured to activate the light source 602 based on inputs from one or more sensors. In an embodiment, the light source 602 emits a first color of light 606 when the syringe barrel 408 is filled with a first volume of fluid. The first volume of fluid can be detected using flow or other fluid sensors. The one or more processors may receive a volume signal from the sensors indicating that the first volume of fluid is contained within the syringe barrel 408. In response to the volume signal, the one or more processors may cause the light source 602 to emit the first color of light, e.g., orange. The control unit may be configured such that the light source 602 emits a second color of light 606 when the syringe barrel 408 is filled with a second volume of fluid. For example, in response to detecting the second volume of fluid, the one or more processors may cause the light source 602 to emit the second color of light, e.g., blue. The user may therefore readily recognize whether the syringe is partially filled, based on the presence of orange light, or fully filled, based on the presence of blue light. Of course, the light colors may indicate different levels of fill, or amounts of fluid in the syringe barrel 408, and this example is not limiting. Similarly, an intensity or another light characteristic (other than color) may be altered based on fill level, and thus, the example of color changing is non-limiting.

Figure 7:
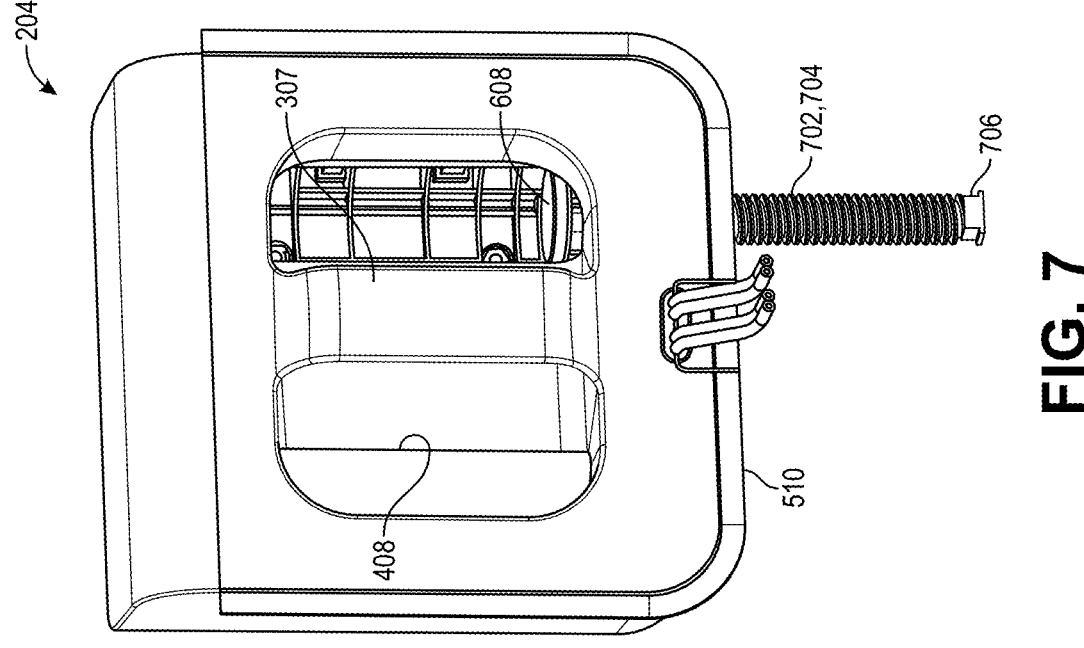
FIG. 7 is a front perspective view of a fluid transfer cartridge, in accordance with an embodiment.

Referring to FIG. 7, a front perspective view of a fluid transfer cartridge is shown in accordance with an embodiment. As described above, each syringe of the fluid transfer cartridge 204 can include a syringe piston 702 disposed within the syringe barrel 408. The leftward syringe barrel is illustrated as opaque, and the rightward syringe barrel is illustrated as transparent to expose the stopper 608 within the syringe cavity. An opacity of the syringe barrel may vary.

The syringe piston 702 can include the stopper 608, which may be a rubber stopper capable of imparting friction and spinning the syringe barrel 408 if not otherwise resisted by the syringe holder 513. The syringe piston 702 may also include a shaft 704 extending from the stopper 608 within the syringe barrel 408 to a shaft end 706 outside of the syringe barrel 408. As described below, the shaft end 706 can include an element to trigger a position sensor. For example, the element can include a magnet to trigger a magnetic sensor, or an optical feature, e.g., a tab, prong, flag, etc., to trigger an optical sensor. Regardless of a position of the stopper 608 within the syringe barrel 408, the shaft end 706 may be outside of the syringe barrel 408. The shaft end 706, however, may have several positions, and at least one of the positions may be inside of the cartridge cavity 402. For example, a bottom surface of the shaft end 706 can be flush with the bottom face 510 of the cartridge shell 306.

In an embodiment, the shaft end 706 is disposed within the cartridge cavity 402 when the stopper 608 is at a home position in the syringe barrel 408. Alternatively, the shaft end 706 may be flush with the bottom face 510 of the cartridge shell 306 when the stopper 608 is at the home position. In either case, the shaft end 706 may not be external to the envelope defined by the cartridge shell 306 when the stopper 608 is at the home position. The home position may be an uppermost position of the stopper 608, or a position nearest to the end face 604 of the syringe. In the home position, the shaft end 706 may be near but outside of the syringe barrel 408. More particularly, the shaft end 706 may have a vertical position between a proximal end of the syringe barrel 408 and the bottom face 510 of the fluid transfer cartridge 204. In the home position, the syringe components are entirely contained within the cartridge cavity 402. Accordingly, the fluid transfer cartridge 204 can have a compact form factor defined by the external surfaces of the cartridge shell 306, and without additional clearances required by the syringe or syringe components.

The fluid transfer cartridge 204 can be shipped with the syringe piston 702 in the home position. More particularly, prior to filling the syringe with the cooling fluid 603 (during shipment or upon initial mounting of the fluid transfer cartridge 204 on the generator 202), the stopper 608 can be at the home position. The package size may therefore be minimized, as compared to shipping the fluid transfer cartridge 204 with the syringe shaft 704 exposed from the cartridge shell 306, to reduce packaging requirements. Furthermore, the fluid transfer cartridge 204 may take up less space within the procedure room because the syringe and syringe components are not exposed outwardly from the cartridge. That is, the ability to move the shaft 704 entirely into the cartridge cavity 402 to contain the syringe entirely within the fluid transfer cartridge 204 can reduce an overall form factor of the fluid transfer cartridge 204. The reduced form factor makes the cartridge more compact for shipping and/or use.

In contrast to the home position, the shaft end 706 may be disposed outside of the cartridge cavity 402 when the stopper 608 is at an end position in the syringe barrel 408. The end position may be a lowermost position, or a position farthest from the end face 604 of the syringe within the syringe barrel. In the end position, the shaft end 706 may be outside of the syringe barrel 408 and the cartridge cavity 402. More particularly, the shaft end 706 can be exposed below the bottom face 510 of the fluid transfer cartridge 204, as shown in FIG. 7.

Figure 8:
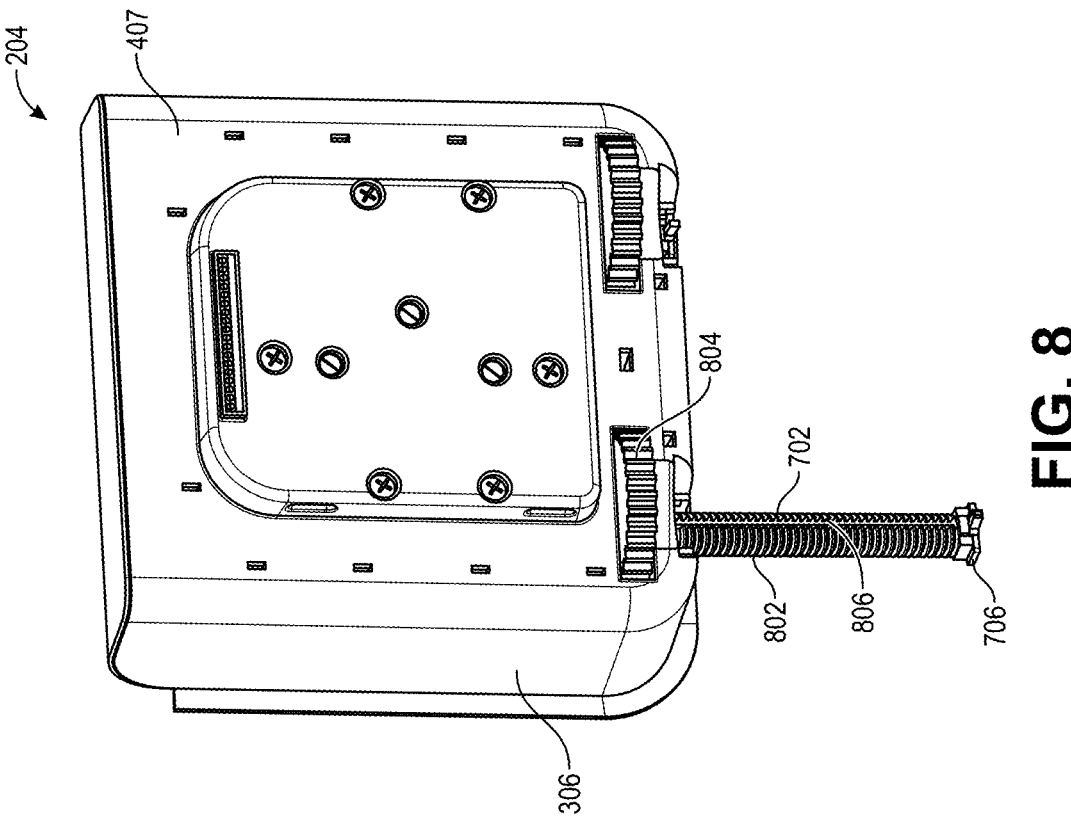
FIG. 8 is a rear perspective view of a fluid transfer cartridge, in accordance with an embodiment.

Referring to FIG. 8, a rear perspective view of a fluid transfer cartridge is shown in accordance with an embodiment. The fluid transfer cartridge 204 includes a drive mechanism to advance the syringe piston 702 relative to the syringe barrel 408. In an embodiment, the shaft 704 of the syringe piston 702 includes an external thread 802 extending along an outer surface of the shaft 704 between the stopper 608 and shaft end 706. The fluid transfer cartridge 204 can also include a gear 804 mounted on the cartridge shell 306. The gear 804 can include an internal thread engaging the external thread 802 of the syringe shaft 704. Accordingly, as the gear 804 rotates, e.g., when driven by a motor of the generator 202, the internal thread of the gear 804 can drive the external thread 802 of the shaft 704 in an axial direction. Thus, the shaft 704 can be driven upward toward the home position and/or downward toward the end position. As the shaft 704 is driven downward, the stopper 608 can move away from the end face 604 of the syringe barrel 408 to draw fluid into the syringe. By contrast, as the shaft 704 is driven upward, the stopper 608 can move toward the end face 604 to expel fluid from the syringe barrel 408.

A rotational frictional load can be applied to the syringe shaft 704 by the gear 804 as the gear 804 drives the syringe piston 702 in the direction of the syringe axis 420. Similar to the stabilizing effect that the syringe holder 513 has on the syringe barrel 408, the fluid transfer cartridge 204 may also include a feature to stabilize the syringe piston 702. In an embodiment, the shaft 704 of the syringe piston 702 includes a notch 806 extending longitudinally between the stopper 608 and the shaft end 706. The longitudinal notch 806 can receive a prong (not shown) that extends from the cartridge shell 306 and/or the syringe holder 513. For example, the prong may be built into the chassis of the cartridge to fix the prong relative to the cartridge housing. As the gear 804 rotates relative to the shaft 704, it may impart a frictional load to the external threads 802 of the shaft 704. To ensure that the shaft 704 does not rotate relative to the gear 804, the prong can slide within the notch 806 and interfere with the notch walls to resist and limit rotation of the shaft 704 relative to the gear 804. The rotational movement is thereby converted into translational movement along the syringe axis 420. More particularly, the prong can limit the rotation of the syringe piston 702 and constrain movement of the stopper 608 to be axial, with minimal rotation.

Figure 9:
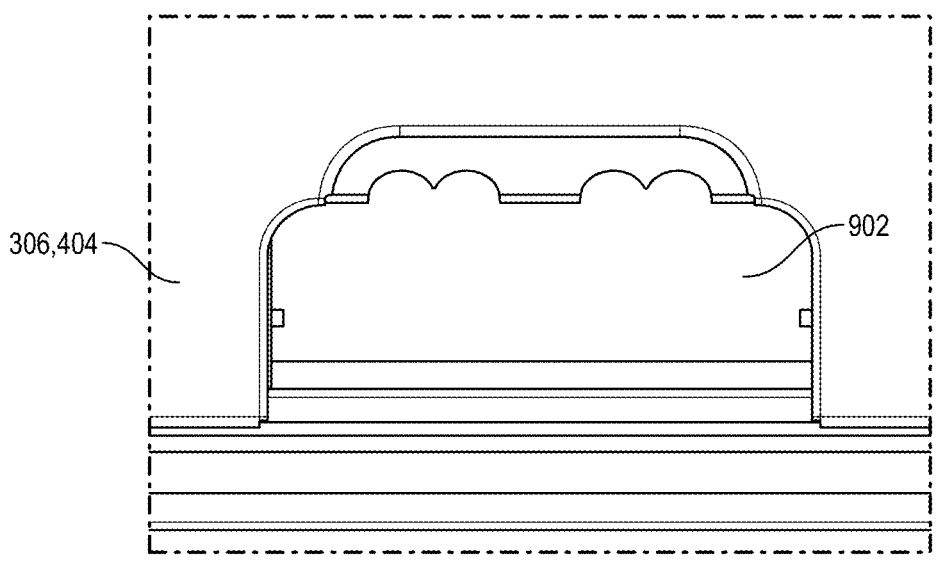
FIG. 9 is a perspective view of a conduit routing port of a fluid transfer cartridge, in accordance with an embodiment.

Referring to FIG. 9, a perspective view of a conduit routing port of a fluid transfer cartridge is shown in accordance with an embodiment. As described above, the components of the fluid transfer cartridge 204 may be fastened in various manners, including snap-fit connections. In an embodiment, the cartridge enclosure may include a conduit routing region through which the fluid conduits 206 may be routed. More particularly, the cartridge shell 306 can include a cartridge routing opening 902 in the front face 404. The cartridge routing opening 902 can improve manufacturability of the fluid transfer cartridge 204 by providing a cutout through which the fluid conduits 206, which may have substantial length, may be lodged into and/or routed through the fluid transfer cartridge 204. The cartridge routing opening 902 can be a cutout formed in the front face 404 along a lower edge of the cartridge. More particularly, the opening can have a lower edge that extends along the corner of the cartridge between the front face 404 and the bottom face 510 of the fluid transfer cartridge 204.

Figure 10:
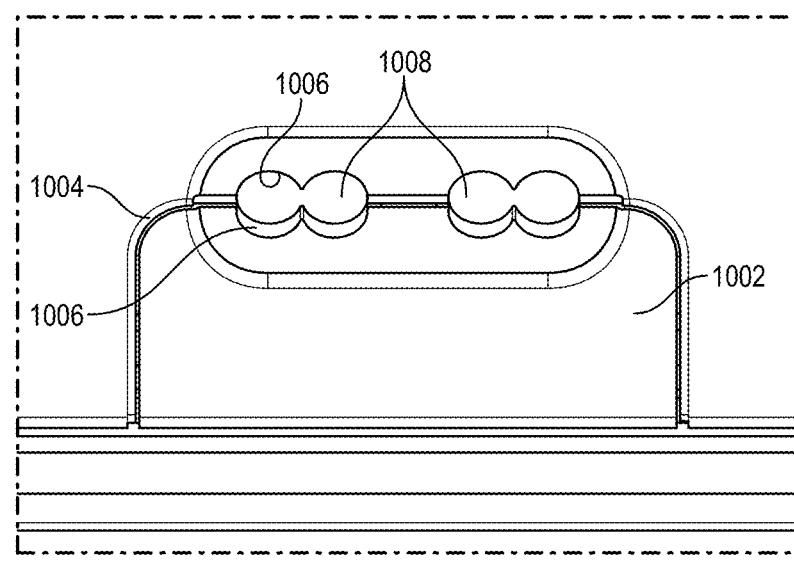
FIG. 10 is a perspective view of a conduit routing plate mounted in a conduit routing opening of a fluid transfer cartridge, in accordance with an embodiment.

Referring to FIG. 10, a perspective view of a conduit routing plate mounted in a conduit routing opening of a fluid transfer cartridge is shown in accordance with an embodiment. The cartridge shell 306 can include a conduit routing plate 1002 that engages the front face 404 along an edge 1004. The edge 1004 can be a perimeter of the conduit routing opening. In an embodiment, the conduit routing plate 1002 and a portion of the front face 404 extending along the conduit routing opening can include respective notches 1006 at the edge 1004. For example, the notches 1006 in the front face 404 can be semicircular notches 1006, and the notches 1006 in a conduit routing plate 1002 may also be semicircular notches 1006. The conduit routing plate 1002 may be snap fit into (or otherwise fastened to) the conduit routing opening to occlude the opening and to form a hole through which the fluid conduit 206 may be routed. For example, the partial cutouts in the enclosure can combine to form conduit ports for the fluid conduits 206. In the case of semicircular notches 1006, the notches can combine to form a circular conduit routing port 1008 in the front face 404 of the assembled fluid transfer cartridge 204. Prior to snapping the conduit routing plate 1002 into the opening, a predetermined length of the fluid conduits 206 may be left exposed outside of the cartridge. When the conduit routing plate 1002 is snapped into the opening, the edge 1004 of the plate and the cartridge shell 306 can clamp around the fluid conduit 206 to hold the fluid conduit 206 in place. The ability to easily determine a length of conduit to insert into the cavity through the opening, and a length of conduit to extend outside of the opening (the lengths being separated by the plate that is snap fit into the opening to clamp the conduit in place) can provide for efficient routing and the ability to quickly and effectively route the conduit during manufacturing.

Figure 11:
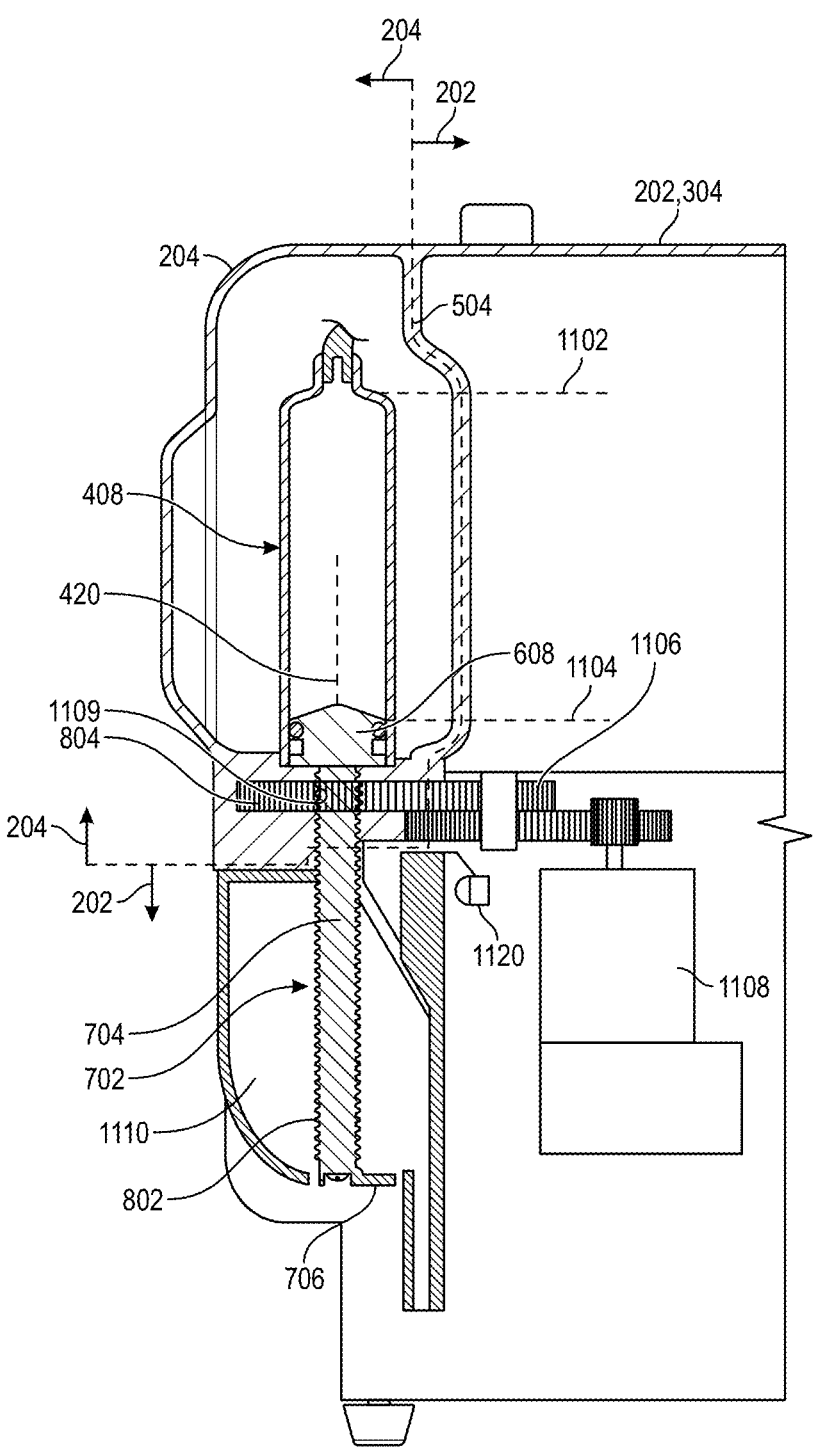
FIG. 11 is a cross-sectional view of a fluid transfer cartridge mounted in a cartridge receptacle of a generator of a treatment system, in accordance with an embodiment.

Referring to FIG. 11, a cross-sectional view of a fluid transfer cartridge mounted in a cartridge receptacle of a generator of a treatment system is shown in accordance with an embodiment. In cross-section, the interaction between the fluid transfer cartridge 204 and generator 202 can be recognized. For example, the back plate 504 of the fluid transfer cartridge 204 is seen to appose and conform to the generator 202 when the fluid transfer cartridge 204 is received within the cartridge receptacle 302. The separation between the fluid transfer cartridge 204 and the generator 202 is depicted in FIG. 11 by a dotted line. When received, the fluid transfer cartridge 204 can be actuated to drive the syringe shafts 704 from a home position 1102 to an end position 1104. More particularly, a generator gear 1106 (or gear train), which is driven by a motor 1108 of the generator 202, can mesh with and drive the gear 804 of the fluid transfer cartridge 204 to concurrently move the syringe piston 702 along the syringe axis 420. For example, the motor 1108 can be operably coupled to the shaft 704, and actuated by the one or more processors of the control unit, to cause an internal thread 1109 of the gear 804 to move the external thread 802 of the shaft 704 (and the syringe piston 702) during fluid transfer by the syringe.

When the stopper 608 is at the end position 1104, the shaft end 706 is outside of the cartridge cavity 402. In an embodiment, the generator housing 304 includes a well 1110 below the cartridge receptacle 302. The well 1110 can have an outer wall surrounding a space within which the shaft end 706 resides when the stopper 608 is at the end position 1104. The well 1110 can therefore receive the syringe piston 702 of the fluid transfer cartridge 204 during fluid transfer by the syringe. When the syringe piston 702 is contained within the well 1110, the shaft 704 can be protected from damage. More particularly, the well 1110 can shroud the shaft 704 such that it does not contact an external surface that might strain the syringe components. Similarly, the well 1110 shields the shaft 704 from the user, thereby reducing pinch points that could otherwise injure the user. Finally, by containing the shafts 704 within the generator 202, rather than extending the shafts 704 outward from the control unit, an overall form factor of the control unit may be compacted.

The well 1110 may be dimensioned to accommodate several functions. First, a size of the space within the well 1110 can allow the user to easily clean out the well 1110, e.g., by wiping the internal surfaces of the well 1110. Furthermore, a height of the well 1110 may be greater than a length of the syringe throw to ensure that the shaft end 706 does not directly contact the internal surface of the well 1110 when the stopper 608 reaches the end position 1104. Additionally, a depth of the well 1110 can allow the fluid transfer cartridge 204 to be removed from the generator 202 without requiring the stopper 608 to be homed. More particularly, when removing the cartridge with the shaft 704 fully extended, the cartridge may be tilted forward and there may be enough space within the well 1110 to allow the shaft 704 to be tilted and removed upward from the well cavity.

As described above, the syringe can be operated to move the stopper 608 within the syringe barrel 408 between the home position 1102 and the end position 1104. The stopper 608 may be placed at the home position 1102, for example, during shipment to the procedure room. The home position 1102 may also be a location at which, after the stopper 608 has been cycled one or more times between the home position 1102 and the end position 1104, the syringe barrel 408 is purged of air bubbles. More particularly, the travel of the syringe can include the home position 1102 of the syringe piston 702 in which the syringe piston 702 removes bubbles from the syringe. Similarly, when the stopper 608 is at the end position 1104, the cooling fluid 603 may be drawn into the syringe barrel 408 to fill the syringe. When the stopper 608 is moved to the end position 1104 after purging the syringe barrel 408, the cooling fluid 603 within the syringe may be free of bubbles. The method of purging the syringes is described in further detail below, however, at this stage it will be appreciated that movement of the syringe piston 702 is effected by the motor 1108, which may be controlled by one or more processors of the control unit.

The movement of the syringe piston 702 can be controlled by the one or more processors through control of the motor 1108. For example, the motor 1108 may be a stepper motor 1108, and the processors can drive the stepper motor 1108 through a predetermined angular rotation that, when considering a gearing ratio between the generator gear 1106 (or gear train) and the gear 804 of the cartridge, will result in a predetermined axial movement of the shaft 704. Additionally, the control unit may incorporate sensors to detect a position of the syringe piston 702, e.g., the shaft end 706. By sensing the shaft position, the one or more processors can determine a location of the stopper 608 within the syringe barrel 408, and thus, an amount of fluid contained within the syringe.

The sensors used to detect the shaft position may be magnetic, optical, mechanical, etc. In an embodiment, the sensors include one or more position switches 1120. For example, the treatment system 100 may include a position switch 1120, e.g., an optical switch such as an optical sensor, configured to detect the syringe piston 702 when the stopper 608 is at the home position 1102. An optical sensor may provide better resolution than a magnetic switch. A magnetic sensor, on the other hand, may require less maintenance than an optical sensor. Accordingly, the position switch 1120 can be selected based on design needs.

Optionally, a second position switch 1120 (not shown) may be configured to detect the syringe piston 702 when the stopper 608 is at the end position 1104. The position switch(es) 1120 may be mounted within or along a wall of the generator well 1110. For example, the position switch(es) 1120 can be mounted along a rear wall of the well 1110. When more than one switches are incorporated, the switches can be aligned in a series along a vertical axis that parallels and runs adjacent to the syringe axis 420.

In an embodiment, the shaft end 706 includes an element that can trigger the position switch(es) 1120. For example, the element can include an optical tab to trigger an optical sensor. The optical tab is described further with respect to FIG. 33, below, and may be mounted at the shaft end 706. The optical tab can travel along the vertical axis and pass by the optical switch(es) as the syringe piston travels vertically along the syringe axis 420. The optical switch(es) of the generator 202 can interact with the optical tab mounted on the syringe piston 702. For example, the optical tab may be disposed on the shaft 704 at the shaft end 706. When the optical tab is in proximity to the optical switch, e.g., adjacent to the optical switch, the optical tab can block the optical switch. For example, the optical sensor can have a light emitting diode to emit a light signal, and the tab can obstruct or reflect the light signal of the optical sensor. Accordingly, when the state of the optical switch changes, it indicates proximity between the optical tab and the optical switch. Such proximity between the optical tab and the optical switch can be detected and used by the one or more processors of the control unit to determine travel of the one or more syringes of the fluid transfer cartridge 204. More particularly, the one or more processors can monitor the state of the optical switch(es) to identify where the syringe pistons 702 are located relative to syringe barrels 408, and more particularly, a position of the shaft 704 and/or whether the stopper 608 is at the home position 1102, the end position 1104, or located at an intermediate position between the start and end of travel.

In an embodiment, the shaft end 706 includes an element that can trigger the position switch 1120. For example, the element can include a magnet, which may be mounted at the shaft end 706, and can travel along the vertical axis and pass by the switch(es) as the syringe piston 702 travels vertically along the syringe axis 420. The magnetic switch(es) of the generator 202 can interact with the magnet mounted on the syringe piston 702. For example, the magnet may be disposed on the shaft 704 at the shaft end 706. When the magnet is in proximity to the magnetic switch, e.g., adjacent to the magnetic switch, magnet moves contacts of the magnetic switch. Accordingly, when the state of the magnetic switch changes, it indicates proximity between the magnet and the magnetic switch. Such proximity between the magnet and the magnetic switch can be detected and used by the one or more processors of the control unit to determine travel of the one or more syringes of the fluid transfer cartridge 204. More particularly, the one or more processors can monitor the state of the magnetic switches to identify where the syringe pistons 702 are located relative to syringe barrels 408, and more particularly, whether the stopper 608 is at the home position 1102, the end position 1104, or located at an intermediate position between the start and end of travel.

The position switches 1120 may act as limit switches to provide information to the control unit that may be used to prepare the syringes for fluid delivery. Given that the magnetic switches do not require precise alignment between the magnet and the magnetic switch, magnetic switches may provide more reliable limit switches than, for example, mechanically-activated switches. Accordingly, one or more processors of the control unit can use the switch signals from the magnetic switches to control a prep cycle of the syringes.

In the prep cycle, the control unit cycles the syringes, using the limit switches to detect whether the syringes are appropriately filled with the cooling fluid 603, whether the fluid conduit 206 and the manifold of the fluid transfer cartridge 204 are filled with the cooling fluid 603, and to ensure that air bubbles are removed from the fluid conduit 206, the manifold, and the syringes. The control unit purges the syringes during the prep cycle to achieve these goals.

The fluid transfer cartridge 204 can be installed on the generator 202 with the stopper 608 in the home position 1102. When in the home position 1102, the shaft end 706 can be within the cartridge cavity 402, and thus, above and outside of the well 1110. In the home position 1102, the syringe is empty. To begin the prep cycle, the one or more processors of the control unit can drive the motor 1108 to actuate the syringe piston 702 in the downward direction. Movement of the stopper 608 generates a vacuum within the syringe barrel 408 and draws cooling fluid 603 into the syringe. Accordingly, an initial stage of the prep cycle fills the syringe with the cooling fluid 603.

As the syringe fills with fluid, the shaft end 706 moves into the well 1110 outside of the cartridge cavity 402. The one or more processors can determine a level or amount of fill of the syringes. For example, when the stopper 608 is at the end position 1104 in the syringe barrel 408, the shaft end 706 can be disposed adjacent to a lowest position switch 1120 of the generator 202. The proximity of the shaft end to the position switch can trigger, e.g., close (or open) the contacts of the switch, to generate a switch signal that is sent to the one or more processors. The processors can determine, based on the switch signal, that the syringes are filled with a predetermined amount of cooling fluid 603. For example, the predetermined amount of cooling fluid 603 may be a volume of the syringe barrel 408.

While the predetermined amount of cooling fluid 603 may correspond to a determination that the stopper 608 is in the end position 1104, the one or more processors may be configured to determine other fill levels. For example, one or more intermediate position switches 1120 may be placed between an uppermost position switch corresponding to the home position 1102 and the lowermost position switch corresponding to the end position 1104. The placement of the position switches may be selected to correspond to known volumes of fluid within the syringe. For example, position switches may be placed at locations corresponding to 10 mL increments of syringe fill levels.

When the syringes are filled, the prep cycle can proceed. The one or more processors may drive the motor 1108 to cause the syringe piston 702 to move upward to expel cooling fluid 603 from the syringes. The cooling fluid 603 is expelled into a fluid path of the cartridge. For example, the cooling fluid 603 can flow out of the syringe into the fluid conduit 206 that connects the fluid transfer cartridge 204 to the catheter 101. In an embodiment, the syringes are entirely emptied of the cooling fluid 603. The one or more processors may determine that the one or more syringes are empty based on switch signals generated by the position switches. The switch signals can indicate that the stopper 608 is in the home position 1102, and thus, the syringes are empty.

Driving the cooling fluid 603 out of the syringe can remove bubbles from one or more of the syringes or the fluid path of the fluid transfer cartridge 204. More particularly, air that is drawn into the syringe when the stopper 608 is initially moved from the home position 1102 to the end position 1104 can be expelled from the fluid network when the stopper 608 is then driven back toward the home position 1102. Purging the fluid network of air can prime the system to ensure that the fluid network is filled with incompressible fluid, e.g., sterile water, and stable.

In an operation of the prep cycle, after purging air from the syringe, the syringe may be filled with the cooling fluid 603. The one or more processors can drive the motor 1108 to move the stopper 608 from the home position 1102 to the end position 1104. Accordingly, the cooling fluid 603 can be drawn into the syringe barrel 408. After the purging operation, the fluid drawn into the syringe barrel 408 can be mostly or entirely bubble free. In an embodiment, the purging operation may be repeated one or more times until the cooling fluid 603 within the syringe is entirely bubble free.

It will be appreciated that the magnetic switches provide one type of limit switch, and other types of limit switches may be incorporated into the treatment system 100. In an embodiment, the limit switches are optical switches, e.g., optical proximity sensors 2910. Accordingly, the shaft end 706 may be configured to emit or reflect light to a light sensor of the treatment system 100, e.g., a light sensor located within the generator 202.

The optical limit switch may include a light source mounted on the shaft end 706. The light source can shine radially outward from a shaft axis 420, e.g., toward the rear wall of the well 1110 of the generator 202. The rear wall may include one or more light sensors to receive the light that is emitted from the shaft end 706. Alternatively, the rear wall may include proximity light sensors that emit light toward the shaft end 706, and receive the reflected light that is returned from the shaft end 706. Accordingly, the light sensor can detect when the shaft end 706 is proximate to the light sensor, based on the detected light, and send a corresponding switch signal to the one or more processors of the treatment system 100. The processor(s) may use the switch signals to detect and control shaft position, as described above. Accordingly, magnetic switches are a non-limiting example of a limit switch that may be integrated in the treatment system 100, and optical or mechanical switches may also be used to detect shaft position.

Figures 12, 13:
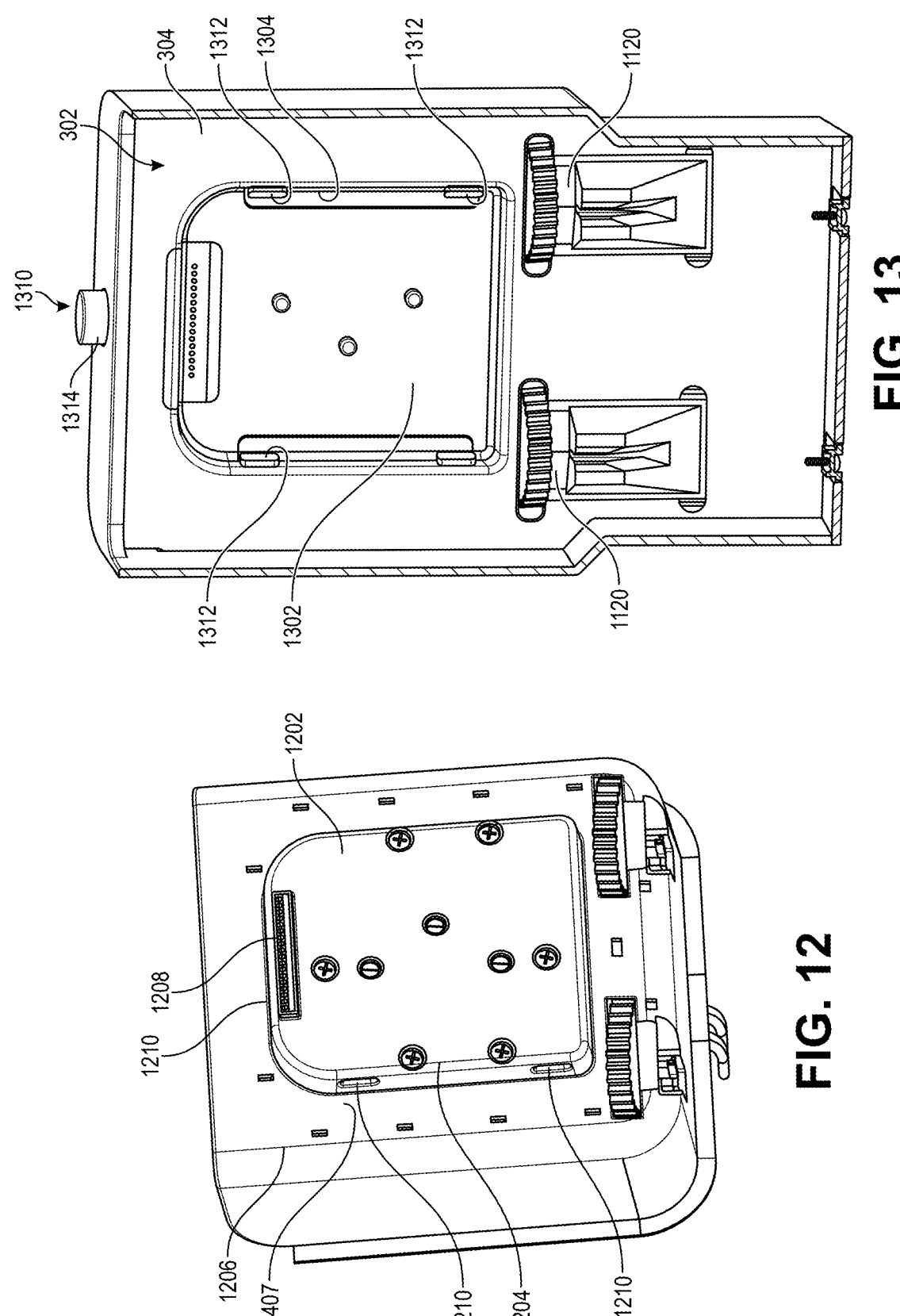
FIG. 12 is a rear perspective view of a fluid transfer cartridge, in accordance with an embodiment.
FIG. 13 is a front perspective view of a cartridge receiving portion of a generator, in accordance with an embodiment.

Referring to FIG. 12, a rear perspective view of a fluid transfer cartridge is shown in accordance with an embodiment. The rear face 407 of the fluid transfer cartridge 204 may appose a surface of the generator 202 defining the cartridge receptacle 302 when the cartridge is mounted on the generator 202. The rear face 407 can include a boss 1202 projecting outward from a surrounding base surface. In an embodiment, the boss 1202 has a boss perimeter 1204 extending around the portion of the rear face 407 on the boss 1202. The boss perimeter 1204 may be laterally inward of an outer perimeter of the rear face 407. More particularly, a rear face perimeter 1206 can define an edge separating the rear face 407 from the top, side, and bottom surfaces of the cartridge. Accordingly, the rear face 407 can have a portion covering the base surface laterally outward of the portion covering boss 1202. The rear face portions may be offset from each other, e.g., at different locations in the rearward direction. Accordingly, the rear surface has a stepped profile when viewed from the side.

In an embodiment, the fluid transfer cartridge 204 includes one or more electrical contact pads 1208 or pins to connect to corresponding circuitry of the generator 202. More particularly, the electrical contact pads 1208 or pins can connect to an electrical circuit board. For example, the electrical circuit board can be a pressure sensor board having sensors and/or processors configured to detect and/or determine pressure along fluid pathways of the control unit. The electrical contact pads 1208 or pins may include spring-loaded electrical contact pins that are exposed through the rear face 407 of the cartridge near an upper end of the boss 1202. The electrical contact pads 1208 may include conductive contact pads exposed through the rear face 407 near the upper end of the boss 1202 and located to make contact with spring-loaded electrical contact pins extending from the generator 202. In this case, the upper end may refer to a side of the boss perimeter 1204 farthest from the floor. The electrical contact pads or pins and their placement at the upper region of the cartridge can provide several benefits. First, in the case of the contact pins, the spring-loaded structure permits the pins to deflect when placed in contact with the generator 202. Thus, the pins can conform to the generator 202 in the event of misalignment or movement between the components during operation. Such benefit is similarly realized when the contact pads of the fluid transfer cartridge 204 engage contact pins of the generator 202. Accordingly, the deflectable pins allow a better connection between the generator 202 and the cartridge during operation. Second, placement of the pads or pins along the top of the cartridge can reduce a likelihood of electrical shorting in the event of a conduit leak. More particularly, the pads or pins can be placed vertically above the fluid path that is internal to the cartridge shell 306 such that any leak from the fluid path will fall downward to the floor without contacting (and potentially shorting) the electrical connections.

Referring to FIG. 13, a front perspective view of a cartridge receiving portion of a generator is shown in accordance with an embodiment. The boss 1202 of the fluid transfer cartridge 204 may engage a corresponding feature in the generator 202. In an embodiment, the cartridge receptacle 302 includes a back recess 1302 to receive the boss 1202. The back recess 1302 can have a recess perimeter 1304 extending around the surface of the generator 202 that is recessed. The recess perimeter 1304 of the back recess 1302 can have a profile that matches a profile of the boss perimeter 1204. For example, the boss 1202 may be a rectangular protrusion and the back recess 1302 may be a rectangular depression. The boss 1202 may therefore engage and fill the back recess 1302 such that a lateral side wall of the boss 1202 apposes and conforms to a lateral side wall of the back recess 1302. Similarly, the rear surface of the fluid transfer cartridge 204 can appose and conform to a front surface of the generator housing 304. The conforming surfaces of the components can stabilize the fluid transfer cartridge 204 relative to the generator 202 and minimize movement between the components during operation.

The contact pads or pins of the fluid transfer cartridge 204 can extend toward or face a slot located in an upper region of the back recess 1302. The slot can expose one or more electrical contacts that the contacts of the fluid transfer cartridge 204 can engage when the cartridge is mounted on the generator 202. Accordingly, an electrical connection can be made between the cartridge and the generator 202 to communicate signals, including switch signals, light activation signals, etc.

To further stabilize the control unit components and secure the fluid transfer cartridge 204 to the generator 202, the treatment system 100 can include a fastening mechanism 1310 to latch the fluid transfer cartridge 204 within the cartridge receptacle 302. The fastening mechanism 1310 can include corresponding catches 1312 and recesses 1210 arranged on the fluid transfer cartridge 204 and the generator 202. Referring again to FIG. 12, the boss 1202 may include several recesses 1210 distributed around the boss perimeter 1204 of the boss 1202. By way of example, the boss 1202 can have a rectangular profile and four or more recesses 1210 may be located within the lateral side wall of the boss 1202 around the boss perimeter 1204. In an embodiment, each of the four recesses 1210 can be located adjacent to a respective corner of the rectangular profile. Distributing the recesses 1210 around the boss perimeter 1204 can distribute the retention load applied to the fluid transfer cartridge 204 by the generator 202, and thus, may optimally stabilize the cartridge relative to the generator housing 304.

Referring again to FIG. 13, the fastening mechanism 1310 can include several catches 1312 distributed around the recess perimeter 1304. By way of example, the back recess 1302 can have a rectangular profile and four latches may be located along the lateral side wall of the back recess 1302 around the recess perimeter 1304. In an embodiment, there are four latches at locations corresponding to the locations of recesses 1210 in the boss 1202. More particularly, the catches 1312 may be configured to engage the recesses 1210 of the boss 1202 to secure the fluid transfer cartridge 204 to the generator 202.

In an embodiment, each catch 1312 is a spring-loaded catch 1312 operably coupled to a release button 1314 of the fastening mechanism 1310. The release button 1314 may be movable between a latched position and an unlatched position. For example, the release button 1314 may be in a latched position when it is fully extended (not pressed). Pressing the release button 1314 can move the button from the latched position to an unlatched position. The release button 1314 can be operably coupled to the catches 1312 such that moving the release button 1314 from the latched position to the unlatched position causes the catches 1312 to move out of the cartridge receptacle 302. More particularly, movement of the release button 1314 can cause the catches 1312 to move from an extended position within the recesses 1210 of the cartridge to a recessed position outside of the boss recesses 1210. When the catches 1312 are engaged with the boss recesses 1210, the cartridge is secured to the generator 202. By contrast, when the catches 1312 retract from the boss recesses 1210, the cartridge may be released from the generator 202. Accordingly, the fastening mechanism 1310 provides a quick release mechanism to install and remove the fluid transfer cartridge 204 from the generator 202.

In addition to providing a quick release mechanism, the fastening mechanism 1310 promotes a secure and stable mechanical connection between the cartridge 204 and the generator 202. The distributed latches around the boss 1202 and back recess 1302 ensure that mechanical loading of the cartridge during operation is evenly distributed, and thus, the latches can share the loading and minimize deflection at any given location around the cartridge. Although the fastening mechanism 1310 can have four or more friction points at which the catches 1312 engage the recesses 1210, the cartridge can be disengaged smoothly using the release button 1314 that actuates the spring-loaded latches. In an embodiment, the catches 1312 are driven by a linkage system, a plate having a cam mechanism, or another intermediate structure between the release button 1314 and the catch 1312. Such mechanisms can operate smoothly and in a manner that provides a favorable degree of tactile feedback to the user. The fastening mechanism 1310 may therefore advantageously secure the cartridge to the generator 202 in a user-friendly manner.

The fastening mechanism 1310 may include one or more catches 1312 that are operably coupled to the release button 1314 such that moving the release button 1314 from the latched position to the unlatched position causes the one or more catches 1312 to move out of the cartridge receptacle 302. The catches 1312 need not be directly spring-loaded, but rather, may be biased in relation to the release button

1314. More particularly, the release button 1314 can be movable from the latched position to the unlatched position, and the release button 1314 may be operably coupled to one or more springs to bias the release button 1314 toward the latched position. Accordingly, the one or more springs can bias the catch(es) 1312 into the cartridge receptacle 302.

In an embodiment, the one or more springs that bias the release button 1314 is a single spring. More particularly, the release button 1314 can be driven to the latched position by the single spring. The one or more catches 1312, by contrast, can include several catches 1312 that are interconnected by a linkage. More particularly, the linkage can interconnect the catches 1312 such that movement of the release button 1314 acts as an input to cause linkage movement that in turn drives the catches 1312 into and out of the cartridge receptacle 302. When the release button 1314 is moved from the latched position to the unlatched position, the one or more catches 1312 can move out of the cartridge receptacle 302.

The treatment system 100 can include one or more processors configured to execute instructions stored in a non-transitory computer readable medium to cause the treatment system 100 to perform various methods, such as the prep cycle described above. The methods can include methods of providing visual feedback to a user to indicate that electrical connections have been made between components of the treatment system 100 or between the treatment system and external components. Several such methods are described below.

In an embodiment, the treatment system 100 can illuminate the syringe upon mounting the fluid transfer cartridge 204 on the generator 202. In an operation, the one or more processors are configured to determine whether the fluid transfer cartridge 204 is received within the cartridge receptacle 302. Detection of cartridge mounting may be made by various sensors. For example, one or more of the electrical contact pads 1208 may engage a corresponding electrical contact of the generator 202 when the cartridge is received in the cartridge receptacle 302. The electrical contact can cause an input signal to be sent to the one or more processors. In response to detecting the input signal, and thus, in response to determining that the fluid transfer cartridge 204 is received within the cartridge receptacle 302, one or more processors can activate the light source 602 of the fluid transfer cartridge 204. The light source 602 may be directed toward the syringe, as described above. Accordingly, when the syringe becomes end-lit, the user is provided with visual feedback to confirm that the components of the treatment system 100 are engaged and ready for operation.

In an embodiment, the treatment system 100 includes one or more indicator lights 452 to indicate that a connection between the generator 202 and one or more external components has been made. Referring again to FIG. 4, the generator 202 may include one or more electrical connectors 450 configured to connect to external connectors of corresponding external components. For example, an electrical connector 450 of the generator 202 may be an electrical socket to receive the external connector 112 of the catheter 101. Additional electrical connectors 450 may include plugs to receive external connectors of other components, such as a remote control device. The external connectors can be plugs that engage the sockets of the external connectors, or vice versa.

The generator 202 can include an indicator light 452 located near the electrical connector 450. For example, the indicator light 452 can be a single light-emitting diode (LED) adjacent to the electrical socket, or several LEDs positioned around the socket. In an embodiment, the indicator light 452 includes an indicator light ring 454 extending around the electrical connector 450. More particularly, as shown in FIG. 4, the indicator light ring 454 can include an annular bezel that circumferentially surrounds the electrical connector 450. One or more LEDs can be mounted behind the bezel such that illumination of the lights causes the bezel to appear as a solid light ring. The light ring can allow the light to be viewed from any direction without being blocked from view, e.g., by a cable or catheter 101.

The indicator light 452 can have a lighting state or mode that provides visual feedback to the user. For example, the one or more processors of the treatment system 100 may be configured to determine whether the electrical connector 450 is electrically connected to the external connector 112. By way of example, when the external connector 112 is plugged into the electrical connector 450, a signal may be sent to the one or more processors that indicates, and allows the processors to determine, that the connection has been made. In an operation, in response to determining that the electrical connector 450 is connected to the external connector 112, a lighting mode of the indicator light 452 can change. In an embodiment, the indicator light 452 changes from a deactivated, unlit state to an activated, lit state. Accordingly, the user can see that the indicator light 452 has become lit to confirm that the external component is electrically connected to the generator 202.

The change in lighting mode from an unlit to a lit state is provided as a non-limiting example. Alternatively, the change in the lighting mode may be from a first lighting mode in which the indicator light 452 emits light, e.g., blinks, to a second lighting mode in which the indicator light 452 continuously emits lights, e.g., the lighting is viewed as being solid. In another alternative, the change in the lighting mode may be from a first lighting mode in which the indicator light 452 emits a first color of light, e.g., red, to a second lighting mode in which the indicator light 452 emits a second color of light, e.g., blue. In any case, the change in the lighting mode provides visual feedback to the user that the external component is electrically connected to the generator 202 and therefore ready for use.

Figure 14:
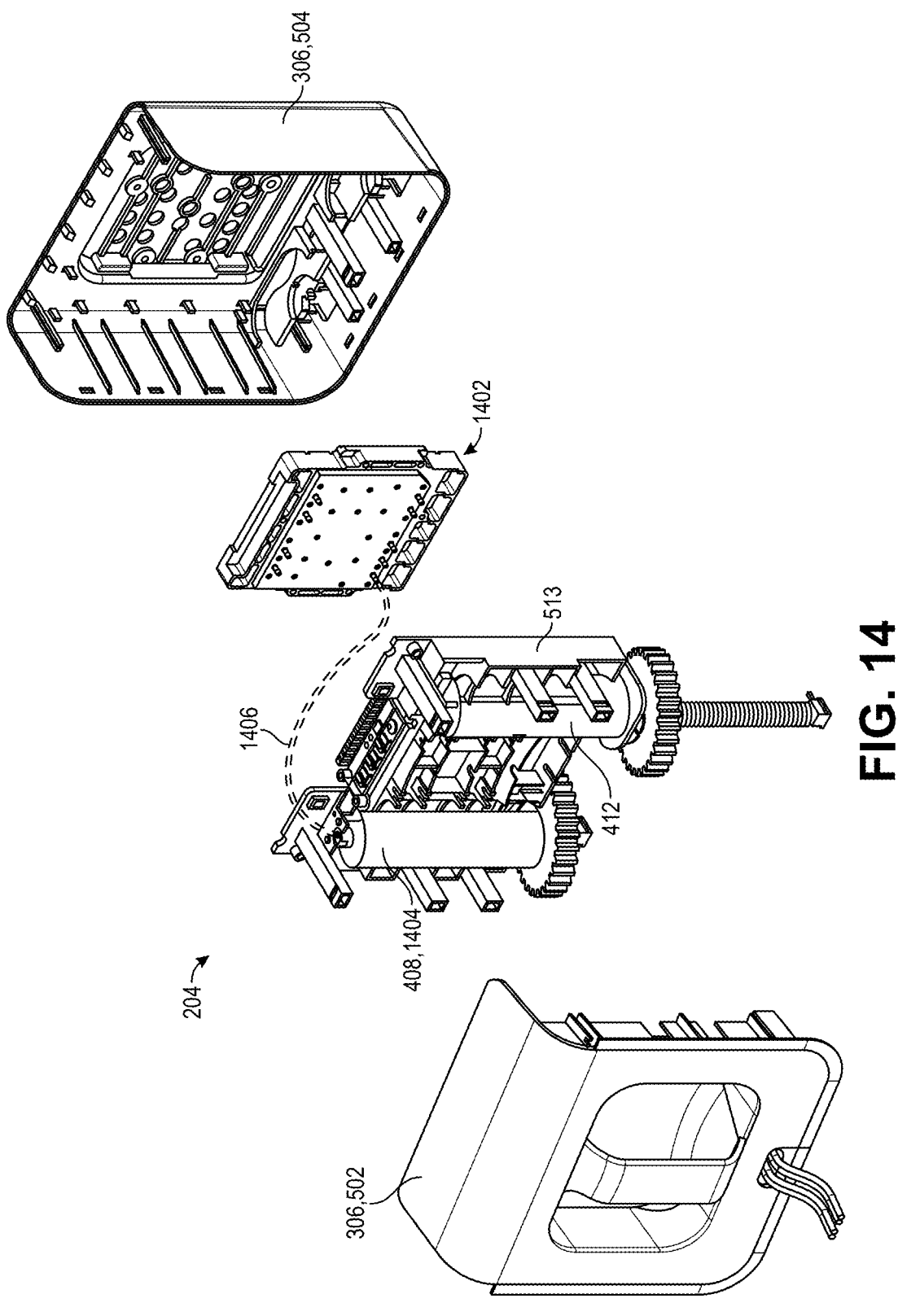
FIG. 14 is an exploded view of a cartridge shell of a fluid transfer cartridge, in accordance with an embodiment.

Referring to FIG. 14, an exploded view of a cartridge shell of a fluid transfer cartridge is shown in accordance with an embodiment. As described above, the cartridge shell 306 of the fluid transfer cartridge 204 can include the handle front plate 502 and the back plate 504. When combined, the handle front plate 502 and the back plate 504 can define the cartridge cavity 402 centrally located between the various walls and faces.

When snapped or otherwise fit together, the handle front plate 502 and the back plate 504 can contain, within the cartridge cavity 402, one or more components to provide fluid transfer functionality. For example, the fluid transfer cartridge 204 can include the syringe holder 513 to hold the syringe barrels 408, 412 within the cartridge cavity 402. The syringe holder 513 can stabilize the syringes during fluid delivery. The fluid transfer cartridge 204 can also include tubing 1406 to facilitate the movement of fluid from the syringes to the catheter 101.

The use of tubing to transfer fluid throughout the fluid transfer cartridge 204 may require long conduit lines and many glue joints to achieve the fluid pathway and interconnections that are needed for fluid transfer. For example, the exclusive use of tubing could require more than five feet of tubing and forty glue joints to create the fluid network. Such a fluid network, however, could occupy a substantial volume, could lead to leaks and/or flow inconsistency at the glued joints, and may be challenging to assemble during manufacturing. In an embodiment, a cartridge manifold 1402 may be used to replace much of the tubing length and joints, thereby providing a more compact, reliable, and easier to manufacture fluid network. Due to the reduced size and weight of the fluid network, the corresponding size and weight of the fluid transfer cartridge 204 may also be reduced, allowing more cartridges to be sterilized at once and more cartridges to be shipped per unit volume.

The cartridge manifold 1402 may replace some, but not all, of the fluid tubing within the fluid transfer cartridge 204. By way of example, the syringe barrel 408 may have a syringe cavity 1404, which is connected to fluid channels of the cartridge manifold 1402 by one or more conduits 1406. Other conduits 1406, e.g., between the cartridge manifold 1402 and the second syringe barrel 412, the balloon catheter 101, a fluid reservoir, etc., may also be routed through the cartridge cavity 402. Such conduits 1406 are not shown in FIG. 14 to avoid cluttering the illustration.

Figure 15A:
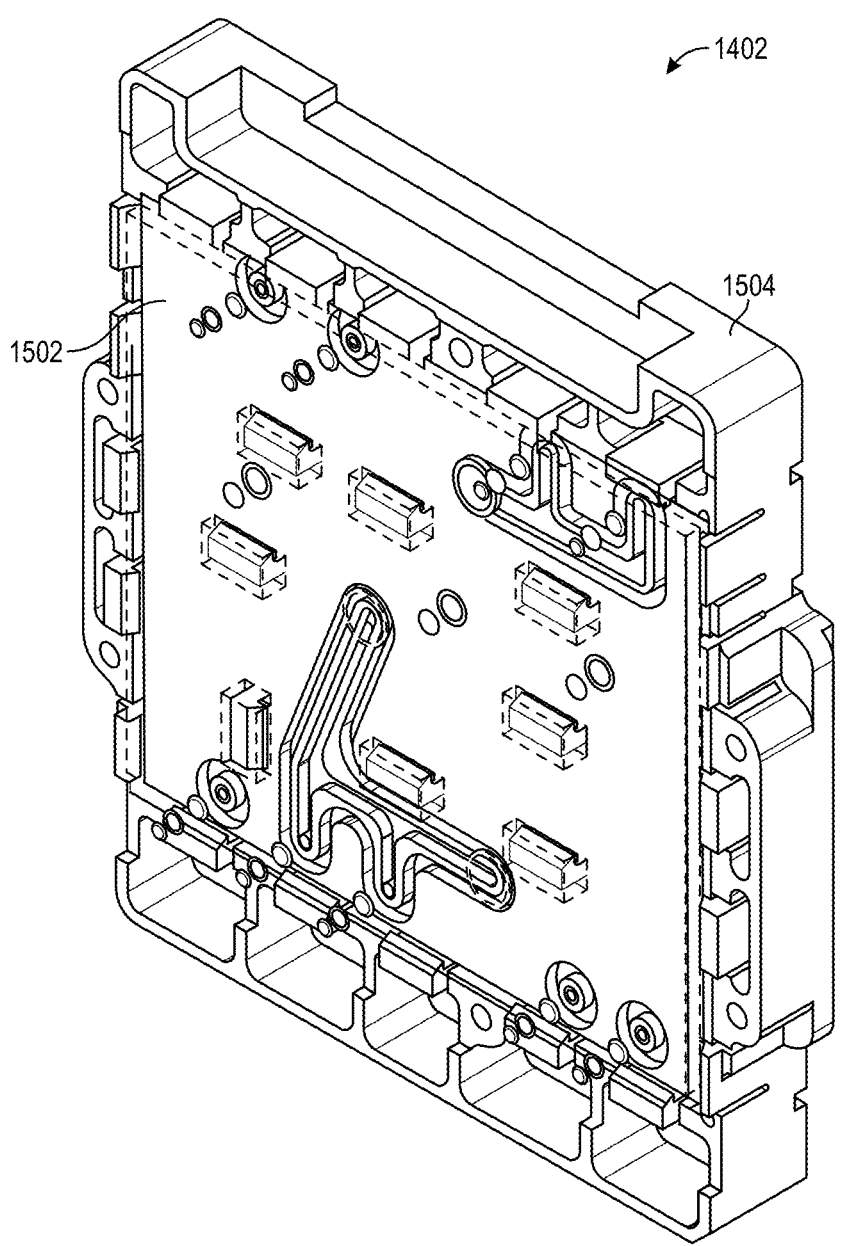
FIGS. 15A-15B are perspective views of a cartridge manifold, in accordance with an embodiment.

Referring to FIG. 15A, a perspective view of a cartridge manifold is shown in accordance with an embodiment. The cartridge manifold 1402 can include several plates assembled to each other. In an embodiment, the cartridge manifold 1402 includes a fore plate 1502 assembled to an aft plate 1504. The fore plate 1502 and the aft plate 1504 can be secured to each other. For example, the fore plate 1502 may be snap fit, e.g., secured by snap closures, to the aft plate 1504. As described below, the fore plate 1502 and the aft plate 1504 can secure an intermediate plate that has channels and ports to move cooling fluid throughout the cartridge manifold 1402, and to exchange the cooling fluid with external components such as the balloon catheter 101 and the fluid reservoir. The fore plate 1502 is rendered transparent to allow the intermediate plate to be viewed in FIG. 15A.

Figure 15B:
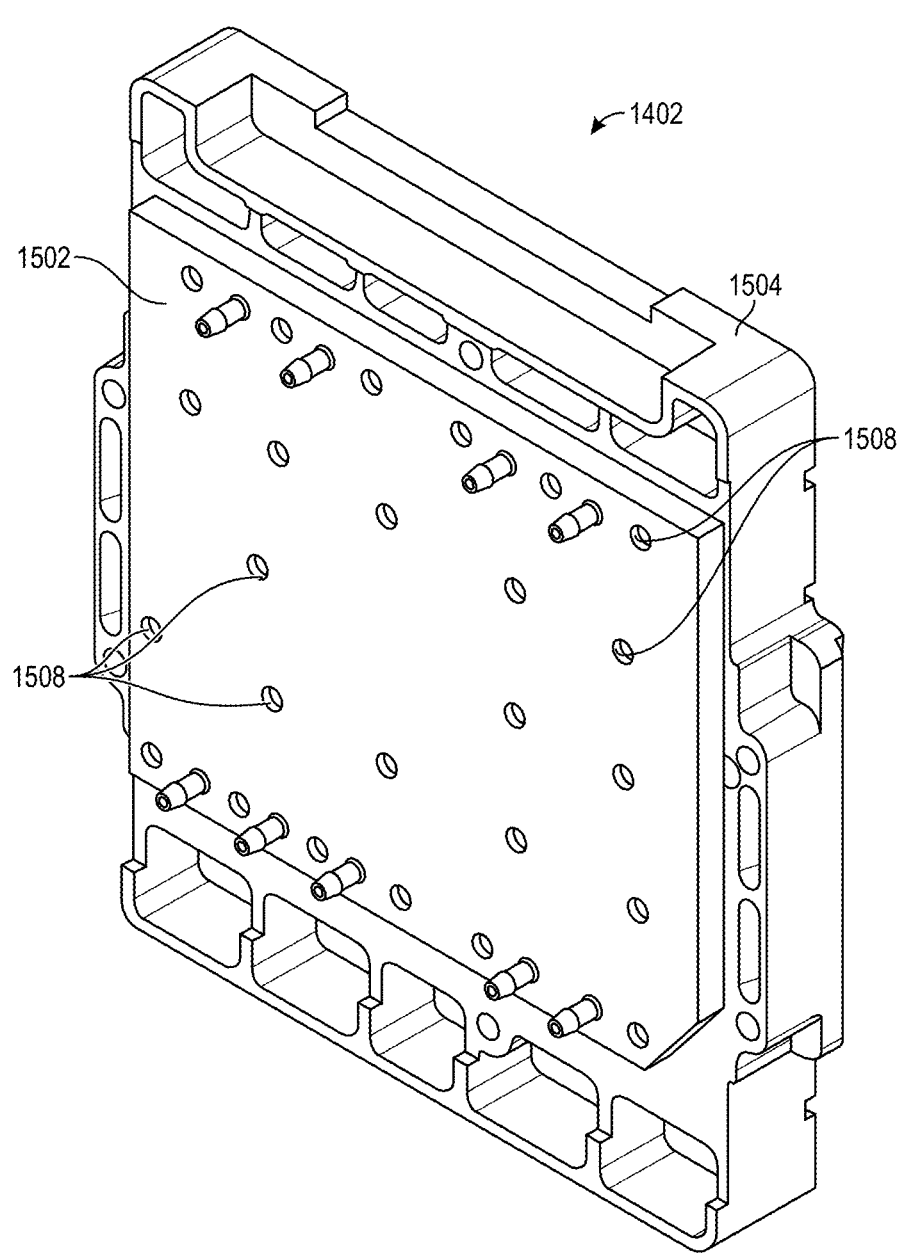

Referring to FIG. 15B, a perspective view of a cartridge manifold is shown in accordance with an embodiment. Alternatively, the fore plate 1502 and the aft plate 1504 may be fastened by screws or otherwise secured to each other. More particularly, several manifold fasteners 1508 can extend through through-holes in the aft plate 1504 and screw into threaded holes formed in the fore plate 1502. The fasteners 1508 can hold the plates together to sandwich an intermediate plate, as described below.

Figure 16:
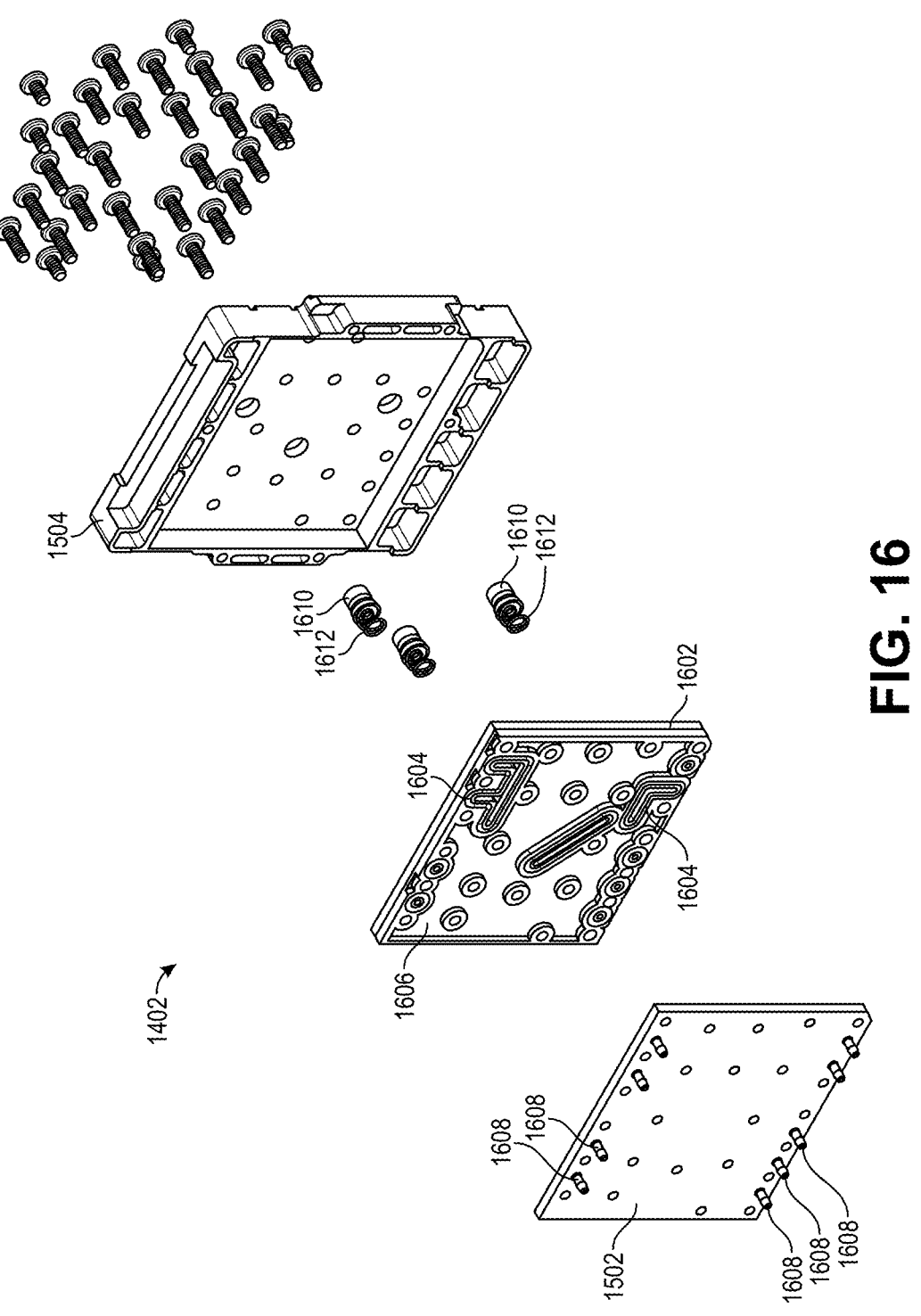
FIG. 16 is an exploded view of a cartridge manifold, in accordance with an embodiment.

Referring to FIG. 16, an exploded view of a cartridge manifold is shown in accordance with an embodiment. The cartridge manifold 1402 in the cartridge cavity 402 can include a fluid transfer plate 1602 sandwiched between the fore plate 1502 and the aft plate 1504. The fluid transfer plate 1602 can include channels on front and rear surfaces that are connected through various ports in the plate. More particularly, one or more front fluid channel 1604 in a front plate surface 1606 can carry the cooling fluid, via channels on the rear surface, to one or more outlet ports 1608 for transfer to the external components.

In an embodiment, the outlet ports 1608 of the fore plate 1502 connect to external components. More particularly, the outlet ports 1608 can include fittings, e.g., barb fittings, that connect to fluid conduits 1406, and those conduits can extend to connect to external components, such as syringes, fluid reservoirs, the balloon catheter 101, or pressure sensors. Accordingly, the fore plate outlet ports 1608 can function as fluid interfaces to the external components. Through the outlet ports 1608, fluid can be transferred into and out of the cartridge manifold 1402. In an embodiment, the fore plate 1502 includes four outlet ports 1608 along an upper edge 1004 and five outlet ports 1608 along a lower edge 1004, although the number and locations of these outlet ports 1608 can be varied according to a layout of the external components and the fluid transfer cartridge 204.

Movement of the fluid through the channels and ports of the cartridge manifold 1402 can be controlled by one or more pistons 1610. Each piston 1610 may be associated with, or include, a spring 1612. More particularly, the piston 1610 may be spring-loaded to bias the piston 1610 to a given position. For example, as described below, the spring 1612 may bias the piston 1610 to an open position and a solenoid can actuate the piston 1610 to move the piston 1610 to a closed position. In particular, the piston 1610 can be moved between positions that seal or unseal fluid ports in the fluid transfer plate 1602 to start or stop flow of the cooling fluid 603 through the fluid channels.

Figures 17, 18:
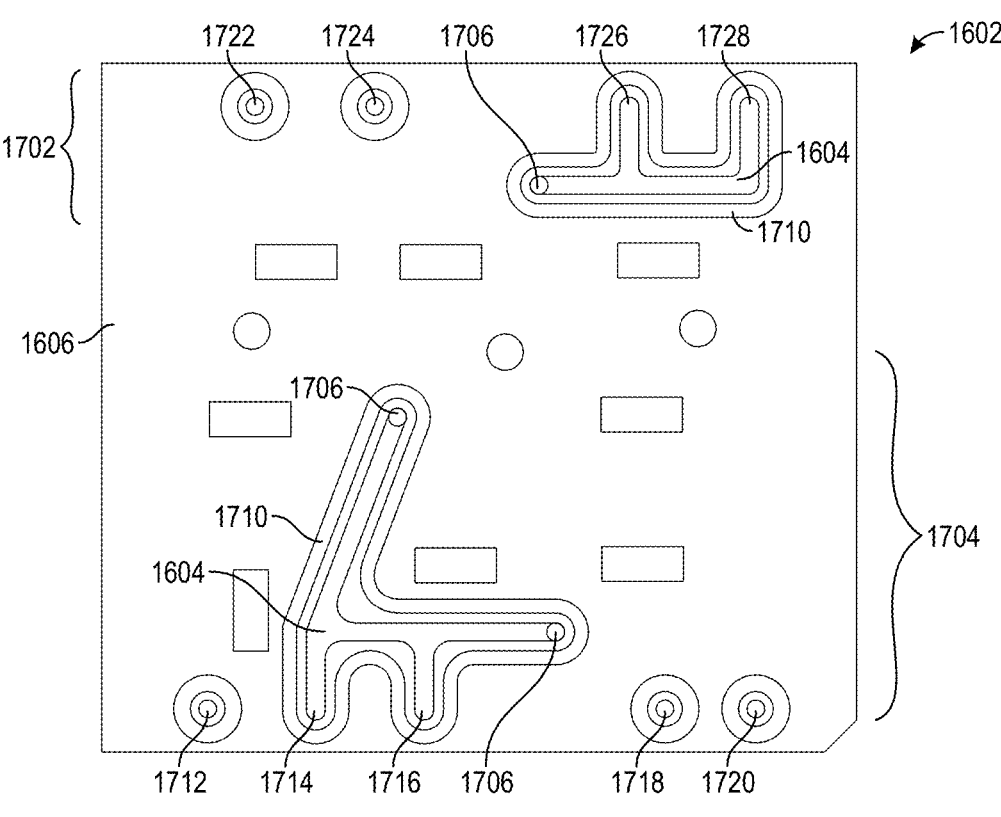
FIG. 17 is a front view of a fluid transfer plate of a cartridge manifold, in accordance with an embodiment.
FIG. 18 is a rear view of a fluid transfer plate of a cartridge manifold, in accordance with an embodiment.

Referring to FIG. 17, a front view of a fluid transfer plate of a cartridge manifold is shown in accordance with an embodiment. The front plate surface 1606 of the fluid transfer plate 1602 can include several front fluid channels 1604. In an embodiment, the front fluid channels 1604 belong to respective fluid circuits. More particularly, some channels and ports may belong to an upper fluid circuit 1702, and other channels and ports may belong to a lower fluid circuit 1704. Each of the fluid circuits can include respective front fluid channels 1604 and one or more outlets. The fluid channels and outlets, as described below, can be interconnected with outlet ports 1608 of the fore plate 1502 to transfer fluid to and from external components. Furthermore, the fluid transfer plate 1602 can include one or more fluid port 1706. Each fluid port 1706 can extend through the fluid transfer plate 1602 from the front fluid channels 1604 in the front plate surface 1606 to rear fluid channels in a rear plate surface (FIG. 18). Accordingly, cooling fluid 603 can be moved from the channels in front of the fluid transfer plate 1602 to channels behind the fluid transfer plate 1602 through the fluid ports 1706.

In an embodiment, the fluid channels of the fluid transfer plate 1602 may be surrounded by respective channel seals 1710. The channel seals 1710 can be gaskets, e.g., O-rings, or strips of elastomeric material having circular, rectangular, cross-shaped, or other cross-sectional profiles, that are placed along an outer perimeter of the fluid channels. The seals can be fit into grooves, overmolded into the plate, or otherwise attached to the fluid transfer plate 1602. When the fluid transfer cartridge 204 is assembled, the channel seals 1710 can be sandwiched between the fluid transfer plate 1602 and an adjacent fore plate 1502 or aft plate 1504. The sandwiched seals can form a hermetic seal around the fluid channels to isolate the cooling fluid 603 within the channels.

The lower fluid circuit 1704 may be associated with the syringe barrel 408 that is used to deliver fluid to the balloon catheter 101. More particularly, cooling fluid 603 may be transferred from an external fluid reservoir, e.g., a fluid-filled bag, through the lower fluid circuit 1704 to the syringe barrel 408. The outlets of the front plate surface 1606, which connect to respective outlet ports 1608 of the fore plate 1502, can be labeled for ease of reference. For example, the lower fluid circuit 1704 can have an L1 outlet 1712, an L2 outlet 1714, an L3 outlet 1716, an L4 outlet 1718, and an L5 outlet 1720. Each of the L1-L5 outlets 1720 can connect to fittings on the fore plate 1502 that are in turn connected to conduits 1406. More particularly, the L1-L5 outlets can be in fluid communication with the outlet ports 1608 along the lower edge 1004 of the fore plate 1502. Those conduits 1406 may connect to external components such as the fluid reservoir, the syringe barrel 408, an inlet line of the balloon catheter 101, and/or one or more pressure sensors.

The upper fluid circuit 1702 may be associated with the second syringe barrel 412 that is used to draw fluid from the balloon catheter 101. More particularly, cooling fluid 603 may be transferred from the balloon catheter 101 through the upper fluid circuit 1702 to transfer the fluid to the external fluid reservoir. The outlets of the front plate surface 1606, which interconnect to respective outlet ports 1608 of the fore plate 1502, can be labeled for ease of reference. For example, the upper fluid circuit 1702 can have a U1 outlet 1722, a U2 outlet 1724, a U3 outlet 1726, and a U4 outlet 1728. Each of the U1-U4 outlets can connect to fittings on the fore plate 1502 that are in turn connected to conduits 1406. More particularly, the U1-U4 outlets can be in fluid communication with the outlet ports 1608 along the upper edge 1004 of the fore plate 1502. Those conduits 1406 may connect to external components such as an outlet line of the balloon catheter 101, the second syringe barrel 412, the fluid reservoir, and/or one or more pressure sensors.

It is apparent that some of the outlets are in fluid communication with each other through the fluid channels. For example, the U3 outlet 1726 and the U4 outlet 1728 are in fluid communication with each other through the front fluid channel 1604 of the upper fluid circuit 1702. Similarly, the L2 outlet 1714 and the L3 outlet 1716 are in fluid communication with each other through the front fluid channel 1604 of the lower fluid circuit 1704. As described below, the outlets that are isolated on the front side of the fluid transfer plate 1602, e.g., the U1, U2, L1, L4, and L5 outlets 1720, may also be in fluid communication with other outlets through fluid channels on the back side of the fluid transfer plate 1602. More particularly, each outlet and/or channel can include a respective fluid port 1706 extending through the fluid transfer plate 1602 to connect to corresponding channel(s) on the back side of the fluid transfer plate 1602.

Referring to FIG. 18, a rear view of a fluid transfer plate of a cartridge manifold is shown in accordance with an embodiment. The cartridge manifold 1402 includes a rear plate surface 1802 having one or more rear fluid channels 1804. Like the front fluid channels 1604, the rear fluid channels 1804 can be surrounded by channel seals 1710 to isolate fluid within the fluid channels. For example, the aft plate 1504 can be apposed to the rear plate surface 1802 such that the channel seals 1710 are sandwiched between the rear plate surface 1802 and the aft plate 1504. By extending around the rear fluid channels 1804, the channel seals can therefore define fluid pathways for transferring the cooling fluid 603.

The rear fluid channels 1804 belong to respective fluid circuits. More particularly, some channels and ports may belong to the upper fluid circuit 1702, and other channels and ports may belong to a lower fluid circuit 1704. The fluid channels and outlets on the rear plate surface 1802 can interconnect with the fluid channels and outlets on the front plate surface 1606 through the fluid ports 1706. More particularly, each fluid port 1706 can extend through the fluid transfer plate 1602 to interconnect the front fluid channels 1604 and ports to the rear fluid channels 1804 and ports. Similarly, given that the fluid channels and ports of the fluid transfer plate 1602 are connected to fittings on the fore plate 1502, which are in turn connected to the syringe barrel 408 through the conduit 1406, then the front fluid channel 1604, the rear fluid channel 1804, and the fluid ports 1706 are in fluid communication with the syringe cavity 1404. Accordingly, cooling fluid 603 can be moved between the syringe cavity 1404 and the channels in the fluid transfer plate 1602. Similarly, cooling fluid 603 can be moved between other external components and the channels in the fluid transfer plate 1602.

The outlets in the rear plate surface 1802 are labeled in FIG. 18 to show correspondence to the outlets in the front plate surface 1606 of FIG. 17. It is therefore apparent that the labeled outlets extend through the plate from the front plate surface 1606 to the rear plate surface 1802. More particularly, in the upper fluid circuit 1702, the U1 outlet 1722 and the U2 outlet 1724 are through-holes that extend through the plate. Similarly, in the lower fluid circuit 1704, the L1 outlet 1712, the L4 outlets 1718, and the L5 outlet 1720 are through-holes that extend through the plate. Accordingly, outlets that are isolated from each other on the front plate surface 1606 may be interconnected through the rear plate surface 1802. For example, the U1 outlet 1722 and the U2 outlet 1724 are physically isolated on the front plate surface 1606, however, those outlets are interconnected through the rear fluid channel 1804 on the rear plate surface 1802. Similarly, the L1 outlet 1712 and L5 outlet 1720 are physically isolated on the front plate surface 1606, however, those outlets are interconnected through the rear fluid channel 1804 on the rear plate surface 1802.

Whereas the fluid channels can interconnect outlets on one side of the plate that are isolated from each other on the other side of the plate, fluid ports 1706 can be used to reversibly interconnect fluid channels on one side of the plate with fluid channels on the other side of the plate. In an embodiment, each fluid port 1706 can be located within a corresponding valve seat on the rear plate surface 1802. The valve seats are labeled for ease of reference in the valve actuation logic described below. The upper fluid circuit 1702 can include a V1 valve seat 1730. The V1 valve seat 1730 can receive a corresponding piston 1610 to open and close the fluid port 1706 that interconnects the front fluid channel 1604 of the upper fluid circuit 1702 with the rear fluid channel 1804 of the upper fluid circuit 1702 at that location. Accordingly, the fluid port 1706 corresponding to the V1 valve seat 1730 can allow or stop fluid transfer between the front fluid channel 1604 and the rear fluid channel 1804 of the upper fluid circuit 1702. Thus, the fluid port 1706 corresponding to the V1 valve seat 1730 can cause the U1 and U2 outlets 1724 to be isolated from, or interconnected with, the U3 and U4 outlets 1728.

In an embodiment, the lower fluid circuit 1704 includes several valves seats. A V2 valve seat 1732 can receive a corresponding piston 1610 to open and close the fluid port 1706 that interconnects the front fluid channel 1604 of the lower fluid circuit 1704 with a first rear fluid channel 1804 of the lower fluid circuit 1704. The first rear fluid channel 1804 can interconnect the L1 outlet 1712 to the L5 outlet 1720. Accordingly, the fluid port 1706 corresponding to the V1 valve seat 1730 can allow or stop fluid transfer between the front fluid channel 1604 and the first rear fluid channel 1804 of the lower fluid circuit 1704. Thus, the fluid port 1706 corresponding to the V2 valve seat 1732 can cause the L2 and L3 outlets 1716 to be isolated from, or interconnected with, the L1 and L5 outlets 1720.

In an embodiment, a V3 valve seat 1734 can receive a corresponding piston 1610 to open and close the fluid port 1706 that interconnects the front fluid channel 1604 of the lower fluid circuit 1704 with a second rear fluid channel 1804 of the lower fluid circuit 1704. The second rear fluid channel 1804 can interconnect the fluid port 1706 at the V3 valve seat 1734 to the L4 outlets 1718. Accordingly, the fluid port 1706 corresponding to the V3 valve seat 1734 can allow or stop fluid transfer between the front fluid channel 1604 and the second rear fluid channel 1804 of the lower fluid circuit 1704. Thus, the fluid port 1706 corresponding to the V3 valve seat 1734 can cause the L2 and L3 outlets 1716 to be isolated from, or interconnected with, the L4 outlets 1718. It will also be appreciated, by examination of the illustrated fluid network, that actuating the pistons 1610 to simultaneously open the fluid ports 1706 at the V2 valve seat 1732 and the V3 valve seat 1734 would therefore place all of the outlets of the lower fluid circuit 1704 in fluid communication with each other through the front fluid channel 1604, the first rear fluid channel 1804, and the second rear fluid channel 1804.

As described above, the fluid network formed by the various channels and ports of the fluid transfer plate 1602 can be used to interconnect various components external to the cartridge manifold 1402. An embodiment of external component connections is now described. Beginning with the upper fluid circuit 1702, the U1 outlet 1722 can connect to the second syringe barrel 412. Accordingly, transferring fluid through the U1 outlet 1722 can transfer fluid to or from the second syringe barrel 412. The U2 outlet 1724 can connect to the fluid reservoir. Accordingly, transferring fluid through the U2 outlet 1724 can transfer fluid to or from the fluid reservoir. The U3 outlet 1726 can connect to a pressure sensor. Accordingly, the U3 outlet 1726 can allow the fluid pressure in the front fluid channel 1604 (or the rear fluid channel 1804 of the upper fluid circuit 1702 when the corresponding valve is opened) to be sensed. The U4 outlet 1728 can connect to an outlet line of the balloon catheter 101. Accordingly, transferring fluid though the U4 outlet 1728 can transfer fluid to or from the outlet line of the balloon catheter 101.

With respect to the lower fluid circuit 1704, the L1 outlet 1712 can connect to an inlet line of the balloon catheter 101. Accordingly, transferring fluid through the L1 outlet 1712 can transfer fluid to or from the inlet line of the balloon catheter 101. The L2 outlet 1714 can connect to the syringe barrel 408. Accordingly, transferring fluid through the L2 outlet 1714 can transfer fluid to or from the syringe barrel 408. The L3 outlet 1716 can connect to a pressure sensor. Accordingly, the L3 outlet 1716 can allow the fluid pressure in the front fluid channel 1604 (or one or both of the rear fluid channels 1804 of the lower fluid circuit 1704 when the corresponding valves are opened) to be sensed. The L4 outlets 1718 can connect to the fluid reservoir. Accordingly, transferring fluid though the L4 outlets 1718 can transfer fluid to or from the fluid reservoir. The L5 outlet 1720 can connect to a pressure sensor. Accordingly, the L5 outlet 1720 can allow the fluid pressure in the first rear fluid channel 1804 of the lower fluid circuit 1704 (or one or both of the front fluid channel 1604 or the second rear fluid channel 1804 of the lower fluid circuit 1704 when the corresponding valves are opened) to be sensed.

Having described the fluid network and, in an embodiment, the external components connected to the fluid network, it is now possible to describe a method of circulating cooling fluid 603 from the fluid reservoir to the balloon catheter 101 and then back to the fluid reservoir. In a first operation, the fluid port 1706 at the V2 valve seat 1732 may be closed and the fluid port 1706 at the V3 valve seat 1734 may be opened. This closing/opening action can be produced by actuation of the pistons 1610, as described below. Alternatively, other valve designs may be integrated with the fluid transfer plate 1602 to open and close the respective fluid ports 1706.

At a first operation, with the V3 valve open, the L2, L3, and L4 outlets may be in fluid communication with each other, and the L1 and L5 outlets may be isolated from the other outlets in the lower fluid circuit 1704. Accordingly, the syringe piston 702 of the syringe barrel 408 may be retracted to draw fluid into the syringe cavity 1404 from the fluid reservoir. More particularly, the cooling fluid 603 can pass from the fluid reservoir into the L4 outlet 1718, through the fluid port 1706 at the V3 valve seat 1734, into the front fluid channel 1604, and out of the L2 outlet 1714 into conduit 1406 connected to the syringe barrel 408. At this stage, the pressure sensor connected to the L3 outlet 1716 can sense pressure of the transferred cooling fluid 603, e.g., in the syringe cavity 1404.

At a second operation, the V3 valve is closed and the V2 valve is opened. At this stage, the L1, L2, L3, and L5 outlets can be in fluid communication with each other, and the L4 outlet 1718 may be isolated from the other outlets in the lower fluid circuit 1704. Accordingly, the syringe piston 702 of the syringe barrel 408 can be advanced to push fluid out of the syringe cavity 1404 into the inlet line of the balloon catheter 101. More particularly, the cooling fluid 603 can pass from the syringe cavity 1404 into the L2 outlet 1714, through the fluid port 1706 at the V2 valve seat 1732, and out of the L1 outlet 1712 into the inlet line of the balloon catheter 101. At this stage, the pressure sensor connected to the L5 outlet 1720 can sense pressure of the transferred cooling fluid 603, e.g., in the balloon catheter 101.

At a third operation, with the V1 valve open, the U1, U2, U3, and U4 outlets may be in fluid communication with each other. Accordingly, the syringe piston 702 of the second syringe barrel 412 may be retracted to draw fluid into the syringe cavity 1404 from the outlet line of the balloon catheter 101. More particularly, the cooling fluid 603 can pass from the outlet line of the balloon catheter 101 into the U4 outlet 1728, through the front fluid channel 1604 and the fluid port 1706 at the V1 valve seat 1730, into the rear fluid channel 1804, and out of the U1 outlet 1722 into conduit 1406 connected to the second syringe barrel 412. The conduit 1406 connecting the U2 outlet 1724 to the fluid reservoir may have a one-way check valve that prevents backflow, and thus, no suction may be applied to the fluid reservoir at the U2 outlet 1724. At this stage, the pressure sensor connected to the U3 outlet 1726 can sense pressure of the transferred cooling fluid 603, e.g., in the syringe cavity 1404.

At a fourth operation, the V1 valve is closed. At this stage, the U1 and U2 outlets 1724 can be in fluid communication with each other, and the U3 and U4 outlets 1728 may be isolated from the other outlets in the upper fluid circuit 1702. Accordingly, the syringe piston 702 of the second syringe barrel 412 can be advanced to push fluid out of the syringe cavity 1404 into the fluid reservoir. More particularly, the cooling fluid 603 can pass from the syringe cavity 1404 into the U1 outlet 1722, through the rear fluid channel 1804 of the upper fluid circuit 1702, and out of the U2 outlet 1724 through the conduit 1406 (and the check valve) to fill the fluid reservoir.

The operations described above can be performed in series and/or in parallel to circulate cooling fluid 603 through the balloon catheter 101. For example, adding fluid to the balloon at the second operation can be performed simultaneously with removing fluid from the balloon at the third operation to balance positive and negative pressures in the balloon such that the balloon diameter remains constant while maintaining a temperature of the cooling fluid 603 within the balloon. Control of the operations can be provided in part based on pressure data fed back to one or more processors by the pressure sensors connected to the cartridge manifold 1402.

Figure 19:
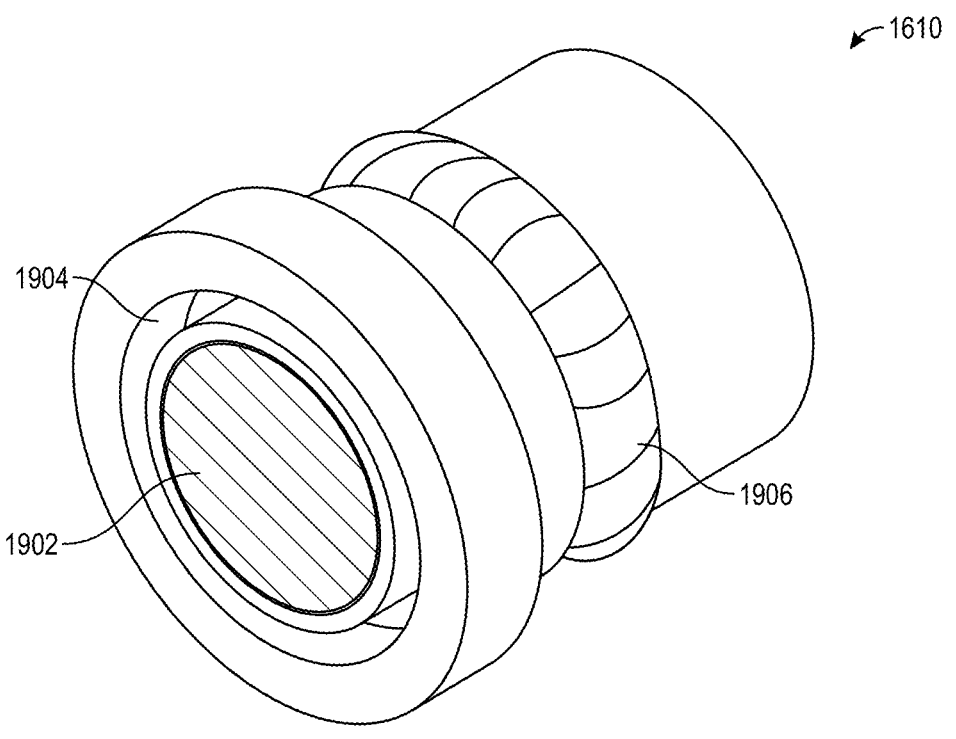
FIG. 19 is a perspective view of a piston of a cartridge manifold, in accordance with an embodiment.

Referring to FIG. 19, a perspective view of a piston of a cartridge manifold is shown in accordance with an embodiment. The valves used to open and close the fluid ports 1706 can include the pistons 1610. More particularly, the pistons 1610 can interact with the fluid transfer plate 1602 to seal and unseal the fluid ports 1706. In an embodiment, the piston 1610 include an end seal 1902. As described below, the piston 1610 can be placed in an open position in which the end seal 1902 unseals (does not occlude) a corresponding fluid port 1706 to allow cooling fluid 603 to pass through the fluid port 1706. The piston 1610 can be moved from the open position to a closed position in which the end seal 1902 seals (occludes) the corresponding fluid port 1706 to stop the cooling fluid 603 from passing through the fluid port 1706. Accordingly, the piston 1610 acts as a valve by covering or uncovering the fluid port 1706 to control fluid flow therethrough.

In an embodiment, the end seal 1902 has a circular distal surface. The distal surface can be flat. The seal can include an elastomeric, cylindrical plug that is lodged into a body of the piston 1610. A face of the plug can extend distally from the body to seal against an opposing surface. For example, the end seal 1902 can press against the rear plate surface 1802 of the fluid transfer plate 1602. More particularly, the face of the end seal 1902 can seal against the rear plate surface 1802 at a corresponding valve seat surrounding the corresponding fluid port 1706 to close the valve. Accordingly, the end seal 1902 can be sized to be larger than the fluid port 1706. For example, a diameter of the face of the end seal 1902 may be larger than, e.g., twice as large as, a diameter of the fluid port 1706.

As described above, the piston 1610 can be spring-loaded. The piston 1610 may include a spring groove 1904. The spring groove 1904 can include an annular groove sized and shaped to receive a proximal end of the spring 1612. The spring 1612 can be a helical compression spring 1612. A distal end of the spring 1612 can be similarly engaged to a corresponding spring groove 1904 at the valve seat. The spring grooves 1904 can stabilize the spring 1612, and allow the spring 1612 to act against both the rear plate surface 1802 and the piston 1610. Accordingly, the spring 1612 can bias the piston 1610 outward to maintain the piston 1610 in a normally open position in which the end seal 1902 is offset from the rear plate surface 1802 to allow fluid flow through the fluid port 1706.

The piston 1610 can include a side seal 1906 to seal against one of the manifold plates. For example, the side seal 1906 can seal against the aft plate 1504. Accordingly, the piston 1610 can include the end seal 1902 to press against the rear plate surface 1802 of the fluid transfer plate 1602, and a side seal 1906 to seal against the aft plate 1504. In an embodiment, the side seal 1906 can include an O-ring that fits within a groove of the piston 1610 body. Thus, the end seal 1902 may have an annular distal surface. The O-ring can extend laterally beyond a cylindrical wall of the body, and thus, when the piston body is inserted into a receiving hole of the aft plate 1504, the side seal 1906 can press against and seal to the aft plate 1504. The side seal 1906 can maintain the seal while sliding against the aft plate 1504, and thus, the piston 1610 may be moved axially within the aft plate 1504. Accordingly, the piston 1610 can be advanced to occlude the corresponding fluid port 1706 or retracted to open the corresponding fluid port 1706.

Figure 20:
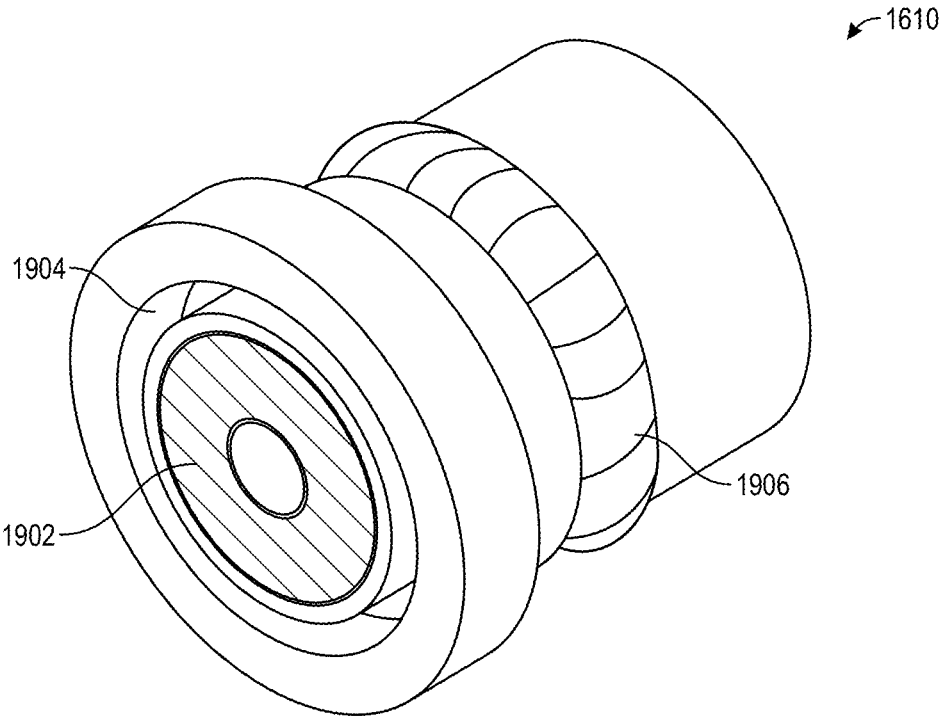
FIG. 20 is a perspective view of a piston of a cartridge manifold, in accordance with an embodiment.

Referring to FIG. 20, a perspective view of a piston of a cartridge manifold is shown in accordance with an embodiment. The end seal 1902 may include an O-ring. The O-ring may be set within a groove in an end of the piston 1610. For example, the groove can be machined and the O-ring may be pressed into the groove. Alternatively, to create a more secure hold of the O-ring, the piston 1610 body may be overmolded around the O-ring. Accordingly, the end seal 1902 may be tightly secured within the piston 1610 body. In either case, the end seal 1902 can extend distally from the piston 1610 body such that the seal can press against the rear plate surface 1802 when the piston 1610 is moved to the closed position. An outer diameter of the annular end seal 1902 can be sized to be larger than the fluid port 1706. For example, the outer diameter of an O-ring end seal 1902 may be larger than, e.g., twice as large as, a diameter of the fluid port 1706.

Figure 21:
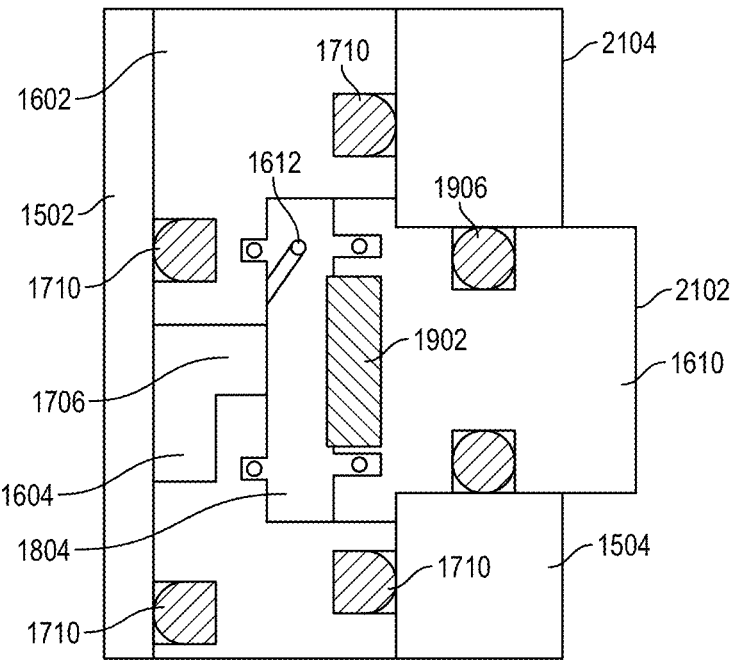
FIG. 21 is a sectional view, taken about line A-A of FIG. 18, of a piston of a cartridge manifold in an open position, in accordance with an embodiment.

Referring to FIG. 21, a sectional view, taken about line A-A of FIG. 18, of a piston of a cartridge manifold in an open position is shown in accordance with an embodiment. The piston 1610 can be a free floating piston 1610 having a side seal 1906 to radially seal against the aft plate 1504, as described above. Furthermore, the end seal 1902 can face the fluid port 1706 in the fluid transfer plate 1602. In the open position, however, the spring 1612 can maintain the end seal 1902 spaced apart from the fluid port 1706. Furthermore, the fluid pressure within the fluid channels in front of the end face 604 can press against the end face 604, biasing the piston 1610 to the open position. Accordingly, cooling fluid 603 may flow through the front fluid channel 1604 and the fluid port 1706 into the rear fluid channel 1804.

Figure 22:
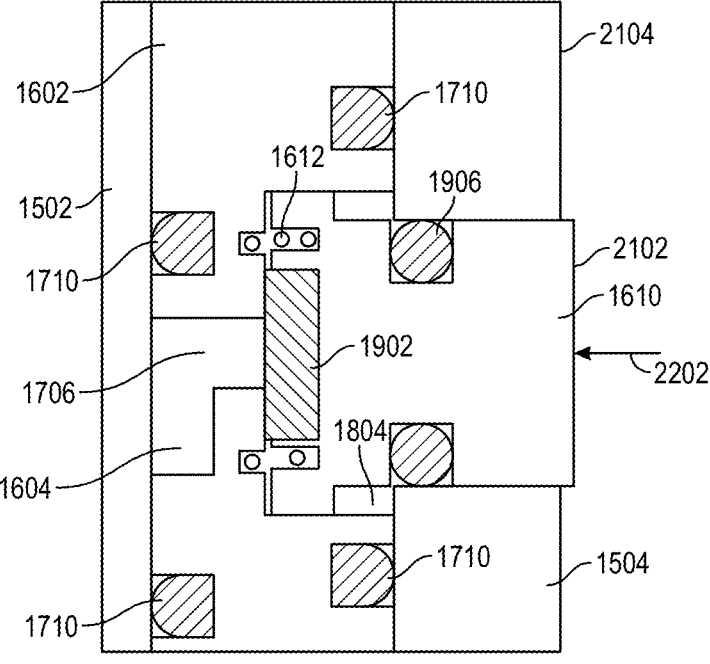
FIG. 22 is a sectional view, taken about line A-A of FIG. 18, of a piston of a cartridge manifold in an closed position, in accordance with an embodiment.

Referring to FIG. 22, a sectional view, taken about line A-A of FIG. 18, of a piston of a cartridge manifold in an closed position is shown in accordance with an embodiment. A solenoid 2202 (force vector shown, but solenoid 2202 omitted) can be actuated to press the piston 1610 forward. The solenoid 2202 force can overcome the spring 1612 and fluid pressure acting against the piston 1610 in an opposite direction to cause the piston 1610 to move to the closed position. In the closed position, the end seal 1902 obstructs the path of fluid flow through the fluid port 1706. More particularly, the cooling fluid 603 is stopped from flowing through the fluid port 1706 to or from the front fluid channel 1604.

Notably, the solenoid 2202 can close the valve using a force of less than 10 lbf, e.g., 5 lbf or less. Such closing force compares favorably relative to alternative valve designs, such as pinch valves that squeeze conduit 1406 tubing. As a result, the cartridge manifold 1402 can also be designed to withstand lower compression forces, allowing for less material to be used in the design and a more compact form factor to be achieved.

The valve can be reversibly moved from the closed position of FIG. 22 to the open position of FIG. 21 by de-energizing the solenoid 2202. When the solenoid 2202 is no longer energized, the compression spring 1612 can act on the piston 1610 to return the piston 1610 to the open position.

As illustrated in FIGS. 21-22, a rear surface 2102 of the piston 1610 can be rearward of a back surface 2104 of the aft plate 1504 in both the open position (FIG. 21) and the closed position (FIG. 22). By maintaining the rear surface 2102 proud of the back surface 2104 in both piston 1610 positions, contact between the solenoids 2202 and the pistons 1610 is facilitated. More particularly, a likelihood of the solenoids 2202 losing contact with the rear surface 2102 is reduced because the rear surface 2102 does not recess 1210 into the hole in the aft plate 1504, below the back surface 2104.

Non-Invasive Pressure/Flow Sensor

As described above, pressure sensors used to monitor balloon inflation may be integrated directly within the system disposables, e.g., the fluid transfer cartridge 204. The pressure sensors are invasive, however, meaning that the pressure sensor contact the inflation fluid directly. As a result of the direct contact, the pressure sensors must be discarded after each procedure. The pressure sensors are expensive, however, so the current practice of using invasive pressure sensing drives up the per procedure cost.

Figure 23:
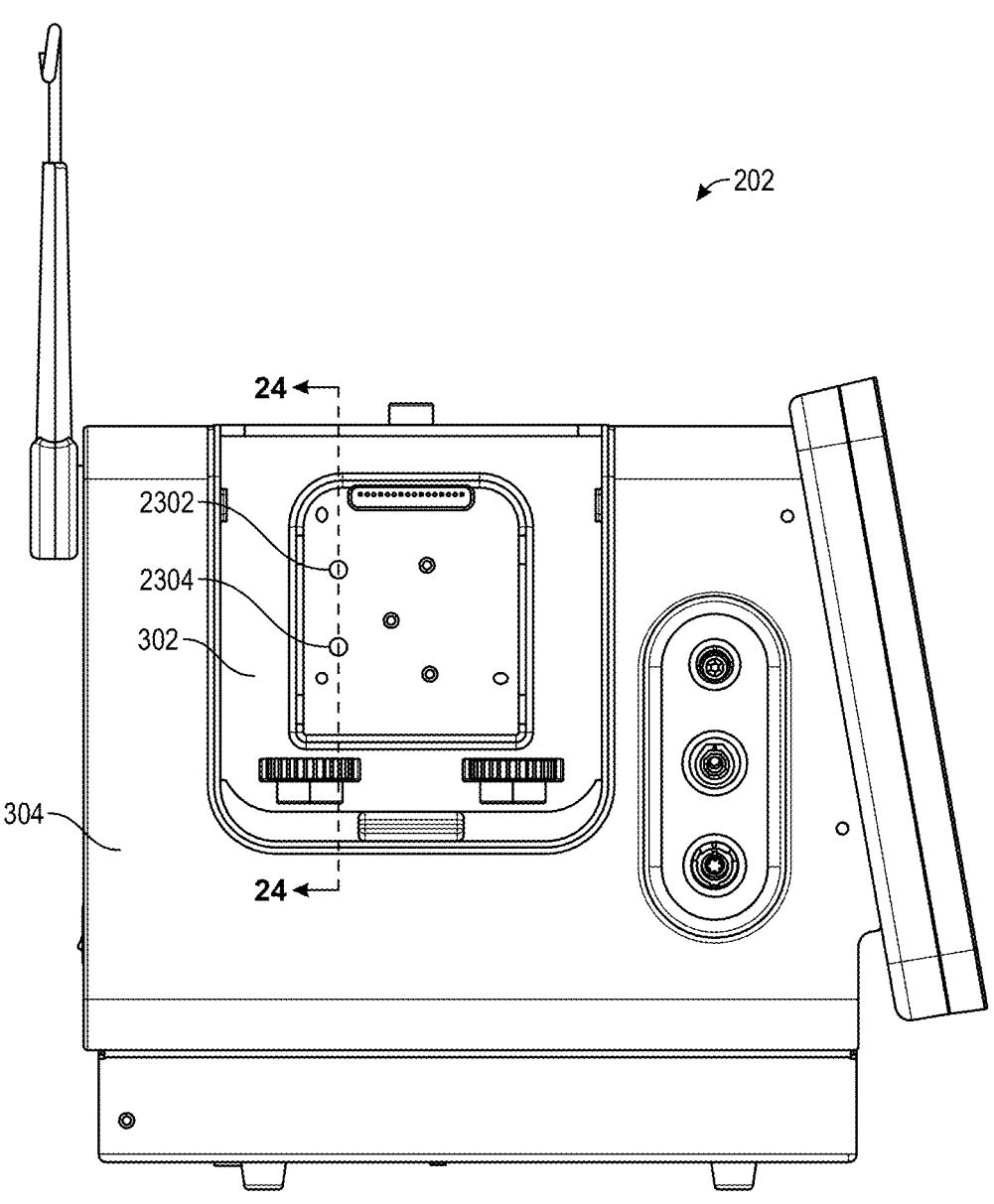
FIG. 23 is a side view of a generator for an ultrasound-based treatment system, in accordance with an embodiment.

Referring to FIG. 23, a side view of a generator for an ultrasound-based treatment system is shown in accordance with an embodiment. Pressure and/or flow sensors can be integrated in the generator 202, rather than being incorporated in the fluid transfer cartridge 204. Furthermore, the generator-located pressure and/or flow sensors can be non-invasive, meaning that they do not directly contact the inflation fluid used to inflate the balloon. The non-invasive sensors can be used for multiple procedures, and thus, can reduce the cost of the disposable by removing costly sensors from the cartridge design.

In an embodiment, a pressure fitting 2302 is mounted on the generator housing 304. As described above, the generator housing 304 has the cartridge receptacle 302 configured to receive the fluid transfer cartridge 204. Accordingly, the pressure fitting 2302 can be behind the cartridge when the fluid transfer cartridge 204 is loaded into the cartridge receptacle 302 of the generator 202. The pressure fitting 2302 may be configured to connect to one or more conduits 1406 of the fluid transfer cartridge 204. For example, when the fluid transfer cartridge 204 is loaded into the generator 202, a fitting of the fluid transfer cartridge 204 that is connected to the conduit 1406 can engage the pressure fitting 2302 of the generator 202. In an embodiment, the pressure fitting 2302 may be connected to the cartridge manifold 1402, e.g., to the outlets of the manifold, through the conduit 1406. Thus, the pressure fitting 2302 may be used to transmit pressure from the cartridge manifold 1402 to the generator 202.

Figure 24:
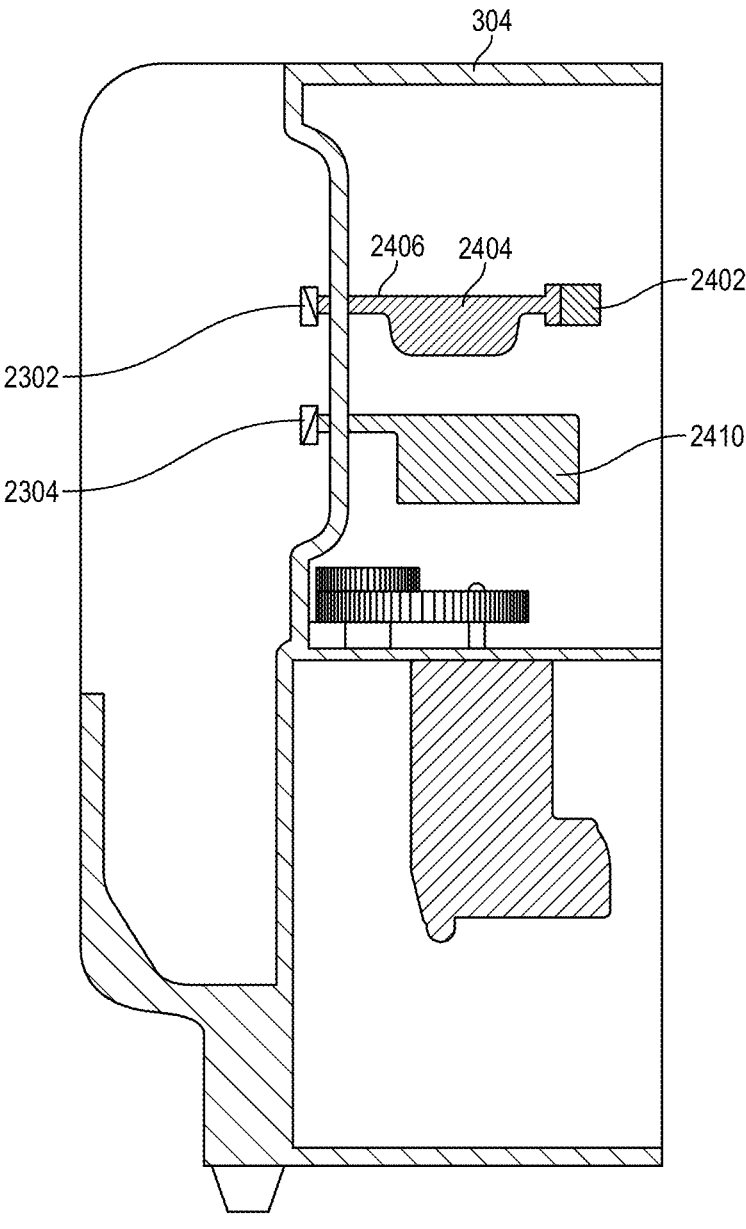
FIG. 24 is a sectional view, taken about line A-A of FIG. 23, of a generator for an ultrasound-based treatment system, in accordance with an embodiment.

Referring to FIG. 24, a sectional view, taken about line A-A of FIG. 23, of a generator for an ultrasound-based treatment system is shown in accordance with an embodiment. In an aspect, the generator 202 incorporates non-invasive pressure sensors 2402 to monitor and measure fluid being transferred through the fluid transfer cartridge 204, e.g., being delivered to the balloon. In an embodiment, the generator 202 includes a pressure sensor 2402 within the generator housing 304. The pressure sensor 2402, which is integrated within the generator 202, is separate from the fluid transfer cartridge 204. The pressure sensor 2402 may be configured to sense pressure at the pressure fitting 2302. Thus, the pressure sensor 2402 may be used to measure fluid pressure being delivered to the balloon through the fluid transfer cartridge 204. Nonetheless, the pressure sensor 2402 may remain within the generator 202 (and re-used) when the cartridge is removed and discarded.

The generator-located pressure sensor 2402, which may replace the cartridge-located pressure sensors described above, can sense the inflation fluid non-invasively. For example, the pressure fitting 2302 may have a diaphragm that contacts the cooling fluid 603, but separates the cooling fluid 603 from the generator cavity. The pressure sensor 2402 may therefore connect to fluid lines that fluidly connect, e.g., tee into, the fluid lines in the cartridge, however, the pressure and/or flow sensors in the generator 202 may be isolated from the fluid in the cartridge. Cooling fluid 603 being fed to the balloon may therefore be sensed without being touched by the pressure sensor 2402. The sensors in the generator 202 can effectively monitor the fluid being fed to the balloon without becoming contaminated. Accordingly, the pressure sensor 2402 is non-invasive and re-usable, and thus, can reduce the cost of the disposable portions of the treatment system 100.

In an embodiment, the diaphragm of the pressure fitting 2302 acts on a fluid, such as air, that is in a line between the pressure fitting 2302 and the pressure sensor 2402. For example, a chamber, e.g., an air chamber 2404, can intervene between the pressure fitting 2302 (and thus, the fluid lines in the cartridge) and the fluid lines in the generator 202. The chamber can have a chamber inlet 2406 connected to the pressure fitting 2302 and a chamber outlet 2408 connected to the pressure sensor 2402. The air in the chamber can compress when the diaphragm is acted upon by the fluid in the cartridge, and thus, the air pressure can change with changes in the balloon inflation pressure. The changes may be sensed by the pressure sensor 2402.

Several types of non-invasive sensors are contemplated, as described further below. In an alternative embodiment, the chamber is a fluid chamber, which rather than being filled with air, may be filled with a liquid. More particularly, the chamber and/or lines between the diaphragm of the pressure fitting 2302 and the pressure sensor 2402 may be filled with an incompressible fluid. Such incompressible fluid may be acted upon by the diaphragm to relay pressure from the fluid transfer cartridge 204 to the generator 202 for non-invasive sensing.

Figure 25:
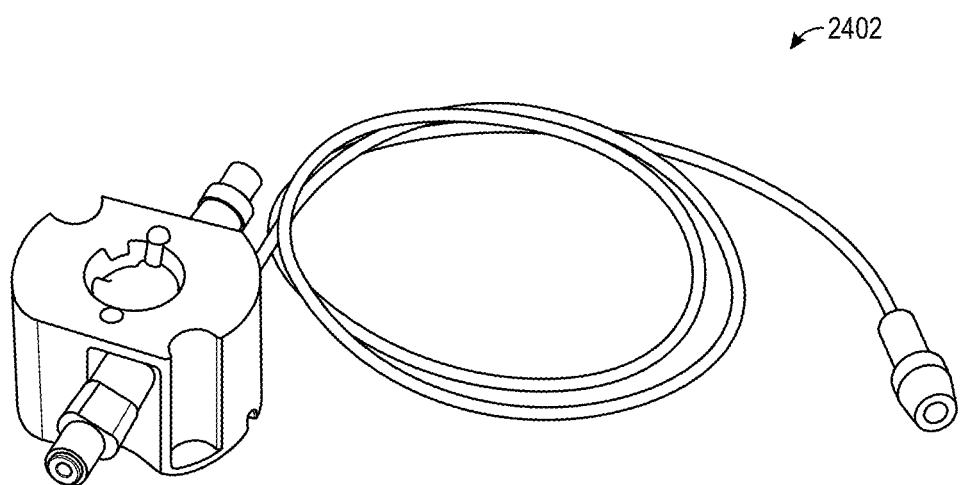
FIG. 25 is a perspective view of a non-invasive sensor, in accordance with an embodiment.

Referring to FIG. 25, a perspective view of a non-invasive sensor is shown in accordance with an embodiment. The pressure sensor 2402 may instead be a flow sensor. The non-invasive pressure and/or flow sensor in the generator 202 may be an ultrasonic sensor. Such sensors can use an ultrasonic signal that is directed into the fluid lines in the generator 202 to detect a Doppler shift of a reflected signal. A processor of the generator 202 can receive the sensed signals and determined, based on the Doppler shift, a flow of fluid within the fluid line. The sensor is non-invasive because the ultrasonic sensor does not contact fluid being fed to the balloon and the information is communicated thru a plastic tube.

Figure 26:
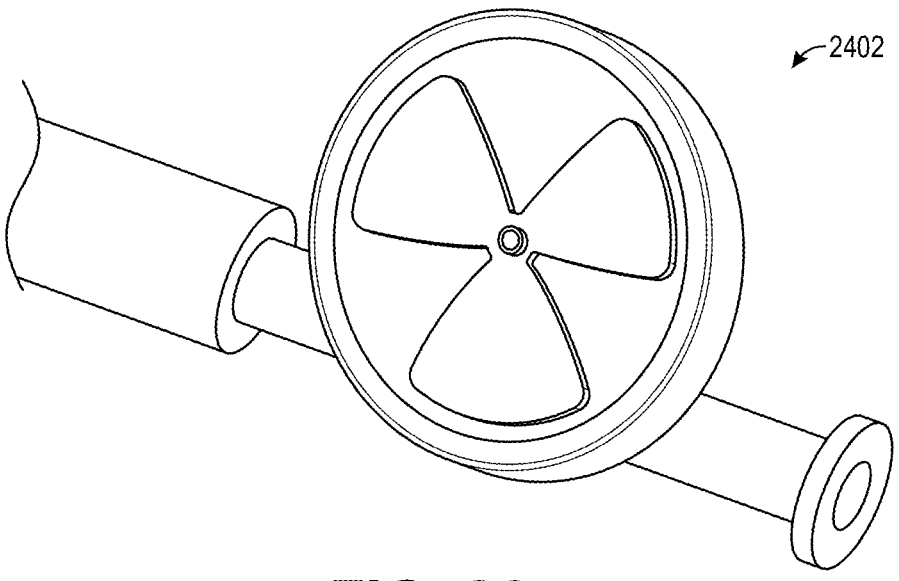
FIG. 26 is a perspective view of a non-invasive sensor, in accordance with an embodiment.

Referring to FIG. 26, a perspective view of a non-invasive sensor is shown in accordance with an embodiment. The non-invasive fluid sensor can include a rotatable element mounted in a housing having an inlet and an outlet. The inlet and outlet can be connected to a fluid line within the generator 202, which is in turn in fluid communication with a fluid line within the cartridge. As fluid flows through the housing, vanes of the rotatable element will be driven. An optical sensor mounted outside of the housing can detect, through a housing wall, a speed of the vanes. The sensed signal may be provided to a processor of the generator 202 to determine, based on the vane movement, a pressure and/or flow of fluid within the fluid lines.

It will be appreciated that other non-invasive sensor types may be used. For example, a motor 1108 may drive a plunger of the cartridge to deliver and retrieve fluid from the balloon. The force required to drive the motor 1108, or a torque output of the motor 1108, may be sensed. The sensed motor parameters (either input or output parameters) can be used by a processor of the generator 202 to determine pressure and/or flow of fluid being transferred to the balloon without actually requiring the sensor to touch the fluid.

In an embodiment, a force sensor can detect force applied to the sensor by the fluid line. For example, the fluid line can include a compliant tubing portion that can be disposed against the force sensor. As pressure increases or decreases within the compliant tubing, the force applied to the sensor will increase or decrease because the tubing wall will expand or contract. The sensed force can be provided to a generator processor to determine, based on the force, a pressure or flow of fluid within the fluid line. The force sensor does not contact the fluid directly, and thus, is a non-invasive sensor that can be used in multiple procedures.

The use of non-invasive sensors in the generator 202 to monitor fluid delivery to/from the balloon, rather than using invasive sensors in the fluid transfer cartridge 204, allows for: the cost of manufacturing the cartridge to be reduced, fluid monitoring sensors to be used for multiple procedures, and thus, a reduction in the per procedure cost.

Pneumatic Syringe Drive

As described above, the fluid drive system may be mechanically-driven. More particularly, the drive system can include a stepper motor, and a transmission having several gears and a worm screw. The mechanical system components may, however, increase the cost and space requirements of the system. Furthermore, the drive system may be complex.

The mechanically-driven fluid drive system may be replaced by a pneumatically-driven fluid drive system. More particularly, the screw drive can be replaced by pneumatic pressure lines. Whereas the screw drive moves the shaft of the syringes by gearing that advances the worm screw, the pneumatic pressure lines can advance/retract the stoppers 608 using positive and negative pressure.

Referring again to FIG. 24, the system can integrate a pneumatic drive system 2410 to advance and/or retract stoppers 608 of the syringes that feed inflation fluid to the balloon. The generator 202 can include a pneumatic fitting 2304 (FIG. 23) connected to the pneumatic drive system 2410. More particularly, the pneumatic fitting 2304 can be mounted on the generator housing 304.

The pneumatic fitting 2304 can be connected to a pneumatic drive system 2410. The pneumatic drive system 2410 can be in the generator housing 304. The pneumatic drive system 2410 may be configured to apply one or more of positive pressure or negative pressure to the pneumatic fitting 2304. For example, the pneumatic drive system 2410 can include a pneumatic pump and/or a vacuum pump that increases or decreases the pressure at the pneumatic fitting 2304.

Figure 27:
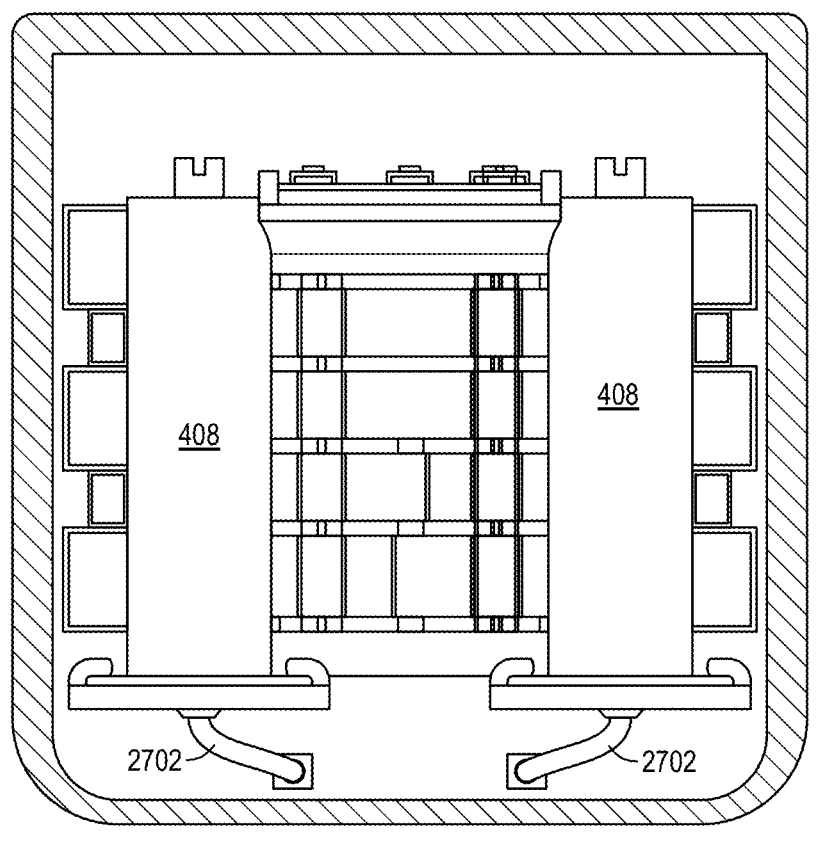
FIG. 27 is a front view of an internal portion of a fluid transfer cartridge, in accordance with an embodiment.

Referring to FIG. 27, a front view of an internal portion of a fluid transfer cartridge is shown in accordance with an embodiment. The pneumatic drive system 2410 can connect to a pressure line 2702 that connects to the syringe. The pressure line 2702, for example, can be a segment of tubing extending from the pneumatic fitting 2304 to a syringe connector that attaches to a base of the syringe barrel 408. By applying positive and negative pressure to the pressure line 2702, a stopper 608 of the syringe can be driven back and forth within the syringe barrel 408. More particularly, positive pressure delivered to the pressure line 2702 through the pneumatic fitting 2304 can drive the stopper 608 upward to advance cooling fluid 603 into a distal fluid line, and negative pressure applied to the pressure line 2702 through the pneumatic fitting 2304 can drive the stopper 608 downward to retract inflation fluid from the fluid line. The inflation fluid can therefore be delivered to and retrieved from the balloon during a procedure.

Figure 28:
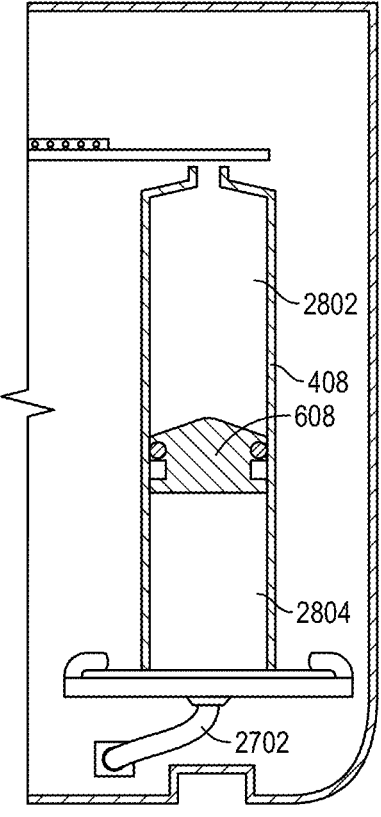
FIG. 28 is a sectional view of an internal portion of a fluid transfer cartridge having a pneumatically driven syringe, in accordance with an embodiment.

Referring to FIG. 28, a sectional view of an internal portion of a fluid transfer cartridge having a pneumatically driven syringe is shown in accordance with an embodiment. The syringes can include respective stoppers 608. The stopper 608 can be disposed within the syringe barrel 408 between a distal syringe cavity 2802 and a proximal syringe cavity 2804. The proximal syringe cavity 2804 is in fluid communication with the pneumatic fitting 2304, and the distal syringe cavity 2802 is in fluid communication with the fluid network distal to the syringe. As described above, the fluid network can include the fluid reservoir. Thus, the distal syringe cavity 2802 can be in fluid communication with the fluid reservoir, e.g., via the cartridge manifold 1402. When the pneumatic fitting 2304 delivers positive pressure to the proximal syringe cavity 2804, the stopper 608 advances to expel cooling fluid 603 from the distal syringe cavity 2802. When the pneumatic fitting 2304 draws vacuum from the proximal syringe cavity 2804, the stopper 608 retracts to draw cooling fluid 603 into the syringe barrel 408.

The use of a pneumatic drive system 2410 simplifies the fluid drive design. The pneumatic system requires fewer parts in the disposable because it replaces a gear and worm screw with a simple pressure line 2702. Accordingly, complexity and cost of the system can be reduced.

In an embodiment, the syringes may be totally removed from the cartridge and relocated next to the fluid reservoir. Alternatively, the syringes could be provided as part of an assembly including the syringes and the fluid reservoir, which can then be connected to the generator 202. In either case, it may be possible to eliminate the cartridge entirely, since the fluid transfer function can be performed directly by the generator 202. In such case, the generator 202 may have inlet/outlet fluid lines that transfer fluid directly from the fluid reservoir to the balloon without being transferred through a cartridge. The generator 202 can include pressure lines 2702 that connect to the syringes, and the syringes can receive/output fluid directly to the reservoir. The generator 202 can include pinch valves that connect to the syringes, and the syringes can receive/output fluid directly to the reservoir. Accordingly, transitioning from a mechanical to a pneumatic drive paradigm has the potential to substantially reduce complexity and cost of the treatment system 100.

Non-Contact Syringe Position Sensing

Positioning of the syringe pistons 702 can be sensed by switches, as described above. More particularly, mechanical switches and/or magnetic switches may be used to detect a position of a piston end. Position feedback may be used by one or more processors of the generator 202 to detect and/or determine when the syringes are empty or full. Mechanical switches may be prone to failure. Furthermore, such switches require precise placement in the generator 202 to provide accurate data. Magnetic switches tend to offer low positional resolution. A precision of such switches is therefore wanting. Accordingly, the treatment system 100 may benefit from position-sensing components that are robust, durable, and accurate. The system can also benefit from information about the syringe piston 702 position over an entire stroke, rather than only at an empty or full position.

Figure 29:
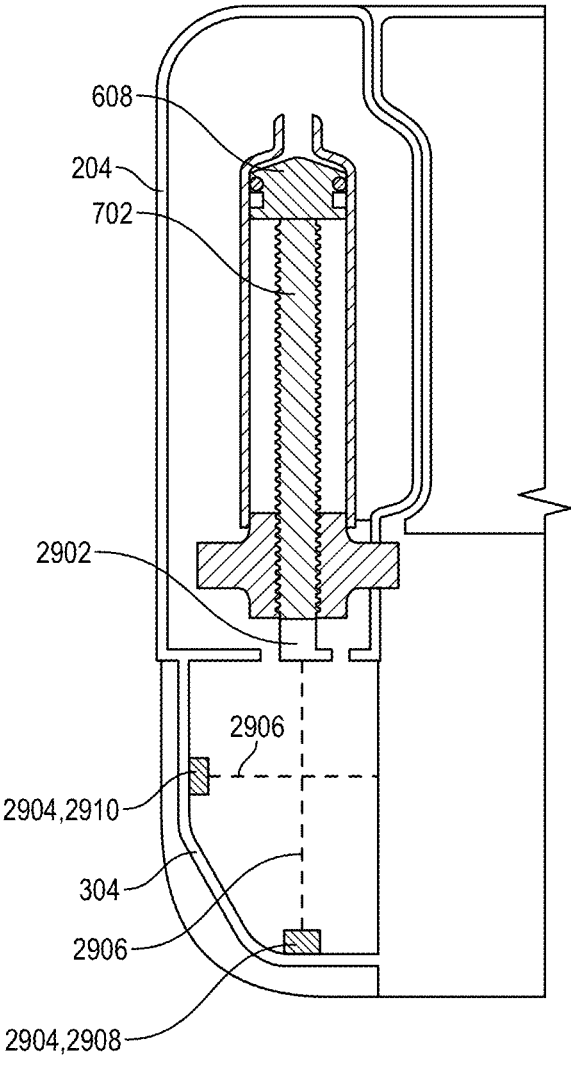
FIG. 29 is a sectional view of an internal portion of a fluid transfer cartridge having a non-contact position sensor, in accordance with an embodiment.

Referring to FIG. 29, a sectional view of an internal portion of a fluid transfer cartridge having a non-contact position sensor is shown in accordance with an embodiment. The generator 202 can include a non-contact position sensor 2904 mounted in the generator housing 304. The non-contact position sensor 2904 may be configured to detect a position of the syringe piston 702 1610. More particularly, the non-contact position sensor 2904 can be positioned and oriented such that a line of sight 2906 of the sensor is directed at a portion of the syringe that is connected to the stopper 608. For example, the sensor can direct radiation, e.g., light, toward the piston and sense reflected radiation that indicates the position of the piston end 2902.

In an embodiment, the non-contact position sensor 2904 includes a time-of-flight sensor 2908. The time-of-flight sensor 2908 may be directed parallel to a central axis of the syringe and/or syringe piston 702. For example, the time-of-flight sensor 2908 can be mounted on a bottom wall of the generator housing 304 facing upward toward the syringe. Accordingly, the sensor can be directed in a longitudinal direction, which is a direction of shaft movement.

The time-of-flight sensor 2908 can emit radiation toward the piston end 2902, and some amount of the radiation may be reflected by the piston 1610 back to the time-of-flight sensor 2908. The reflected signal can be processed by one or more processors of the generator 202 to determine a distance between the time-of-flight sensor 2908 and the piston end 2902. More particularly, a time that the radiation took to move to the piston end 2902 and bounce back to the sensor can be measured and used to determine the distance. Based on known geometrical relationships between the piston end 2902 and the stopper 608 of the syringe, information about a volume of cooling fluid 603 in the syringe can be determined.

In an embodiment, the non-contact position sensor 2904 includes a proximity sensor 2910. The proximity sensor 2910 may be directed parallel to the direction of shaft movement, as described above. However, in an embodiment, the proximity sensor 2910 has a line of sight 2906 that is orthogonal to the direction of shaft movement. For example, the non-contact position sensor 2904 can be mounted on a side wall of the generator housing 304, and may be directed radially through a cavity that receives the syringe piston 702 during syringe operation.

The proximity sensor 2910 can provide a go-no-go indication of whether the piston end 2902 has reached a predetermined location along the direction of movement. As the piston end 2902 moves downward to the location, within the cavity, the proximity sensor 2910 will detect the presence of the piston end 2902. More particularly, an intensity of reflected radiation that is sensed by the proximity sensor 2910 will change when the piston end 2902 passes through the line of sight 2906. Thus, the proximity sensor 2910 can detect the location of the piston end 2902. Several proximity sensors 2910 can be placed along the side wall to detect different locations of the piston end 2902 that correspond to fluid levels of the syringe. For example, several proximity sensors 2910 could sense piston locations corresponding to the syringe being full of the cooling fluid, half-full, and empty.

The syringe position data generated by the non-contact position sensor 2904 can be used to determine a volume of fluid delivered to the balloon catheter 101. The data may be continuous, e.g., over an entire stroke of the syringe, and therefore may provide an indication of the position of the syringe at every position along the stroke. Furthermore, the non-contact position sensors 2904 can be stably mounted on the generator housing 304 and their locations can be calibrated, thus, the position data can be accurate. Time-of-flight, proximity, and other types of non-contact position sensors 2904 are inexpensive, and thus, can be implemented at low cost.

It will be appreciated that alternative sensors and sensor placements may be used. For example, the non-contact position sensor 2904 can include an acoustic sensor, rather than a light sensor. Acoustic sensors emit and receive sound signals to determine presence and distance to a surface (such as the piston end 2902).

The position of the sensor may also be moved to any location within the generator 202. For example, a structure other than the generator housing 304 may provide a mounting location for the non-contact position sensor 2904. In an embodiment, the non-contact position sensor 2904 can be mounted on a structure other than the generator 202. For example, the sensor could be placed on the syringe shaft 704. In such case, the time-of-flight sensor 2908 could be mounted on the shaft end 706. The sensor may be directed in the direction of shaft movement to sense movement of the shaft 704 based on changing distance between the sensor and an adjacent surface, e.g., the generator housing 304.

The position of the sensor may also be moved to any location within the cartridge. For example, a structure other than the cartridge housing may provide a mounting location for the non-contact position sensor 2904. In an embodiment, the non-contact position sensor 2904 can be mounted on a structure other than the cartridge. For example, the sensor could be placed on the syringe shaft 704. In such case, the time-of-flight sensor 2908 could be mounted on the shaft end 706. The sensor may be directed in the direction of shaft movement to sense movement of the shaft 704 based on changing distance between the sensor and an adjacent surface, e.g., the cartridge housing.

Fluid Reservoir Detection

The treatment system 100 includes a fluid reservoir containing the cooling fluid 603 that is circulated through the balloon catheter 101. The fluid reservoir can be a container holding the cooling fluid 603. For example, the container can be a bag containing the cooling fluid 603. The cooling fluid 603 may be selected based on the procedure and/or device that is being used. For example, some balloon catheters 101 may perform optimally with sterilized water, while others may function using saline. Accordingly, the presence and type of fluid reservoir, e.g., its volume and contents, is important to proper system performance. In an embodiment, the treatment system 100 is capable of detecting a presence and/or type of fluid reservoir that is being used during the procedure.

Figure 30:
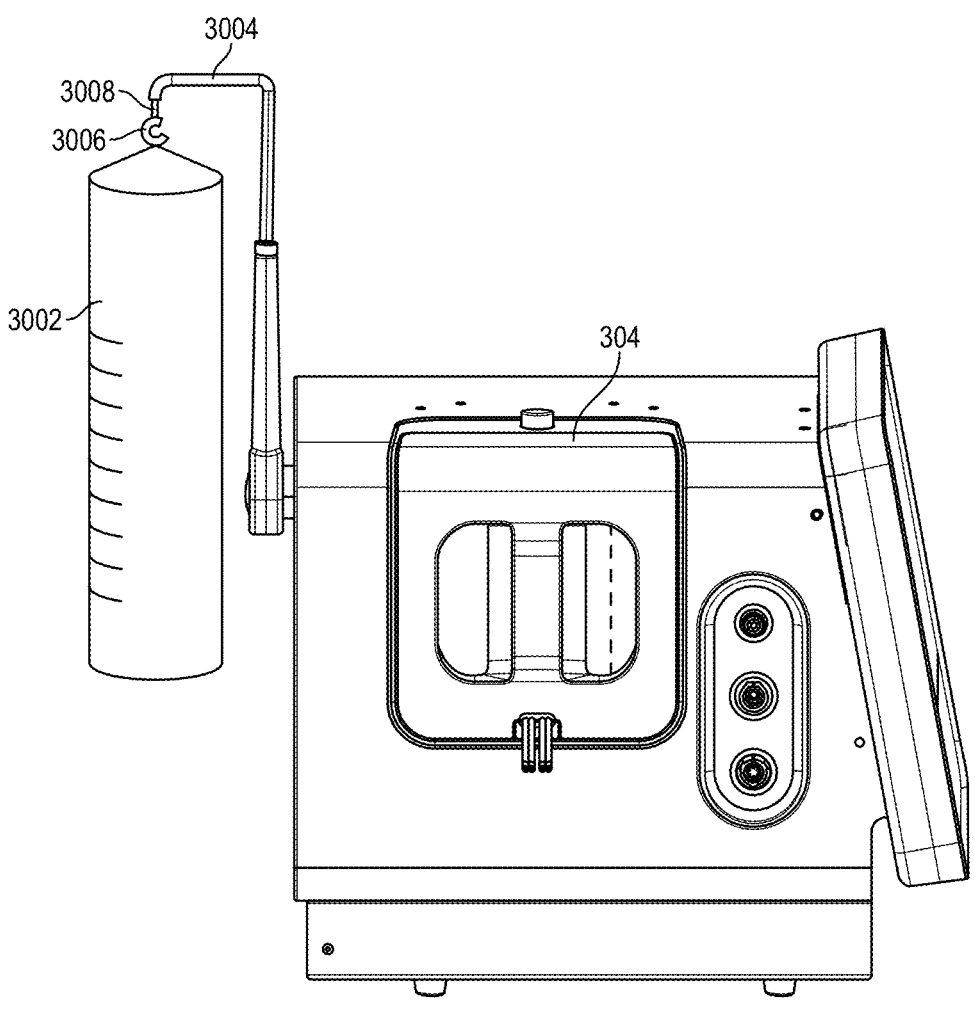
FIG. 30 is a perspective view of an ultrasound-based treatment system, in accordance with an embodiment.

Referring to FIG. 30, a perspective view of an ultrasound-based treatment system is shown in accordance with an embodiment. The treatment system 100 can include a fluid reservoir holder 3004 to hold a fluid reservoir 3002. The fluid reservoir holder 3004 may have an attachment 3006, e.g., a hook, to hold the reservoir. For example, the fluid reservoir 3002 can be a sterilized-water filled bag having a loop that can be placed on the attachment 3006 to hang the bag from the fluid reservoir holder 3004.

In an embodiment, the system includes a sensor to sense a presence and/or characteristic of the fluid reservoir 3002. The characteristic may be a weight of the fluid reservoir 3002. For example, a weight sensor 3008 may be coupled to the attachment 3006 to generate weight data based on a weight of the fluid reservoir 3002. The weight sensor 3008 can be mounted within or on the generator housing 304. Alternatively, the weight sensor 3008 can be integrated with the fluid reservoir holder 3004. For example, the weight sensor 3008 can include a strain gauge having an end connected to the attachment 3006 and an end connected to a crossbar or upright of a bag suspension structure 3004. Accordingly, the strain gauge can be located at any location that undergoes tension, compression, or bending moments as a result of the fluid reservoir weight. Accordingly, the weight sensor 3008 can detect and/or measure physical strain resulting from such loads to generate data corresponding to a weight of the fluid reservoir 3002.

The generated data may be used by one or more processors to determine information about the fluid reservoir 3002. More particularly, the one or more processors can receive the weight data from the weight sensor 3008, and determine, based on the weight data, information corresponding to the fluid reservoir 3002.

In an embodiment, the one or more processors determine whether the fluid reservoir 3002 is present. Presence detection can be used to verify that the fluid reservoir 3002 is available at the right time in the procedure (or determine whether it is removed). The fluid reservoir 3002 may be essential to one or more procedure operations, such as preparing and inflating the balloon catheter 101. When the fluid reservoir 3002 is not present, e.g., when the fluid bag is not hung on the bag stand, those procedural operations can fail, which can undesirably prolong the procedure.

The one or more processors can determine presence of the fluid reservoir 3002 based on the weight data being above a predetermined weight threshold, or within a predetermined range of weight. The one or more processors can generate a presence signal based on the weight. The presence signal may be used as a gate to a logical sequence in the procedure. For example, the presence signal can allow the user interface to advance to subsequent operations in the preparation procedure, or else generate an error message to prompt the user to load or replace the fluid reservoir 3002.

In addition to being a logical gate, the weight data can be used as an interlock to other system components. For example, when the fluid reservoir 3002 is not present, the syringe drive system may be disabled to prevent operation when there is no cooling fluid 603 available to fill the syringe barrel 408. Presence is only one characteristic that can drive the above decisions. Other characteristics that can be sensed include a fluid reservoir type (including cooling fluid type) and/or leak detection.

In an embodiment, the one or more processors determine whether the fluid reservoir is a predetermined fluid reservoir. Weights of fluid reservoirs 3002 may be known based on a volume and density of the cooling fluid 603 stored in the reservoir. For example, a specific volume of saline may have a different weight than the same volume of sterilized water. Furthermore, fluid reservoirs may be made from different materials, e.g., vinyl or silicone, which can also affect the predetermined weight of the fluid reservoir 3002. The treatment system 100 may be calibrated or programmed with the known weights of specific fluid reservoirs. Accordingly, the weight data may be used by the one or more processors to determine whether a particular fluid reservoir having a specified cooling fluid volume and/or type is mounted on fluid reservoir holder 3004.

Certain balloon catheters 101 may use transducers 108 that perform optimally with sterile water as the cooling fluid 603. For example, using saline rather than sterile water with such transducers may cause the transducer to malfunction. Accordingly, the one or more processors can determine whether the fluid reservoir 3002 contains sterile water or saline, based on the weight of the bag. When the one or more processors determine that the fluid reservoir 3002 contains sterile water, the procedure may be allowed to proceed. Alternatively, if the bag contains saline, the one or more processors may generate the error signal and/or lockout operation of other system components to prevent damage to the transducer 108. For example, if the specific weight is not detected, the system can prompt the user to verify that sterile water (or dextrose, etc.) is being used. Accordingly, the weight sensor 3008 can be used to detect whether a correct fluid is being used based on the bag having a specific and unique weight.

In an embodiment, the one or more processors determine whether there is a leak in the fluid reservoir 3002. The weight data may be used to detect that the bag weight is changing during the procedure. More particularly, one or more processors can detect a change in the weight of the fluid reservoir 3002 during the procedure, which may indicate the loss of fluid due to a leak. In response to the leak detection, the system can generate an error message and/or prompt the user to verify that the fluid reservoir 3002 is not leaking, or to take another corrective action.

Figure 31:
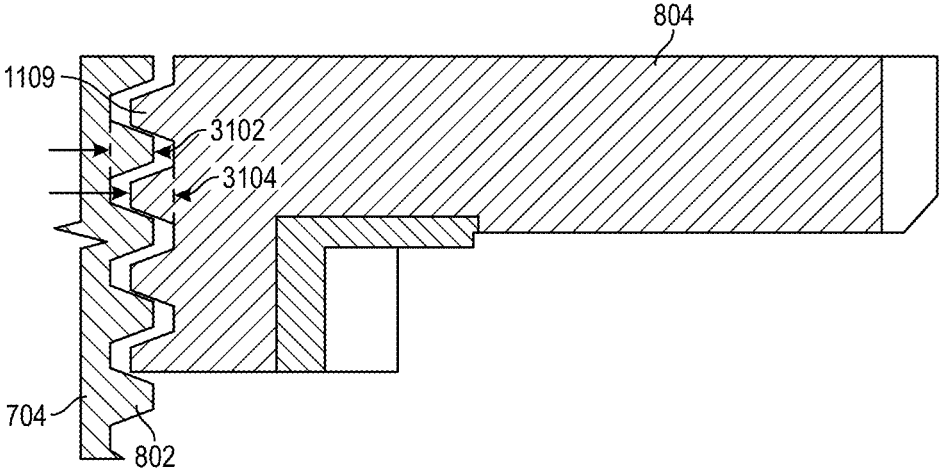
FIG. 31 is a sectional view of a drive mechanism of a fluid transfer cartridge, in accordance with an embodiment.

Referring to FIG. 31, a sectional view of a drive mechanism of a fluid transfer cartridge is shown in accordance with an embodiment. As described above with respect to FIG. 8, the drive mechanism include the shaft 704 of the syringe piston 702 having an external thread 802, and the gear 804 having an internal thread 1109 engaging the external thread 802. In an embodiment, the external thread 802 and the internal thread 1109 are configured to avoid binding between the threads. Binding between the threads can occur, for example, when standard thread designs are used that do not allow for sufficient clearance between the crest and root of the engaged threads. More particularly, binding can occur more frequently when the working depth of the external thread 802 and the internal thread 1109 are equal. In an embodiment, the external thread 802 and the internal thread 1109 have different working depths. For example, the external thread 802 can have an external working depth 3102, and the internal thread 1109 can have an internal working depth 3104. The external working depth 3102 may be greater than the internal working depth 3104. For example, the external working depth 3102 can be at least 25%, e.g., 50%, greater than the internal working depth 3104. The different working depths allow the threads to engage securely without binding as the shaft 704 is driven by the gear 804.

Figure 32:
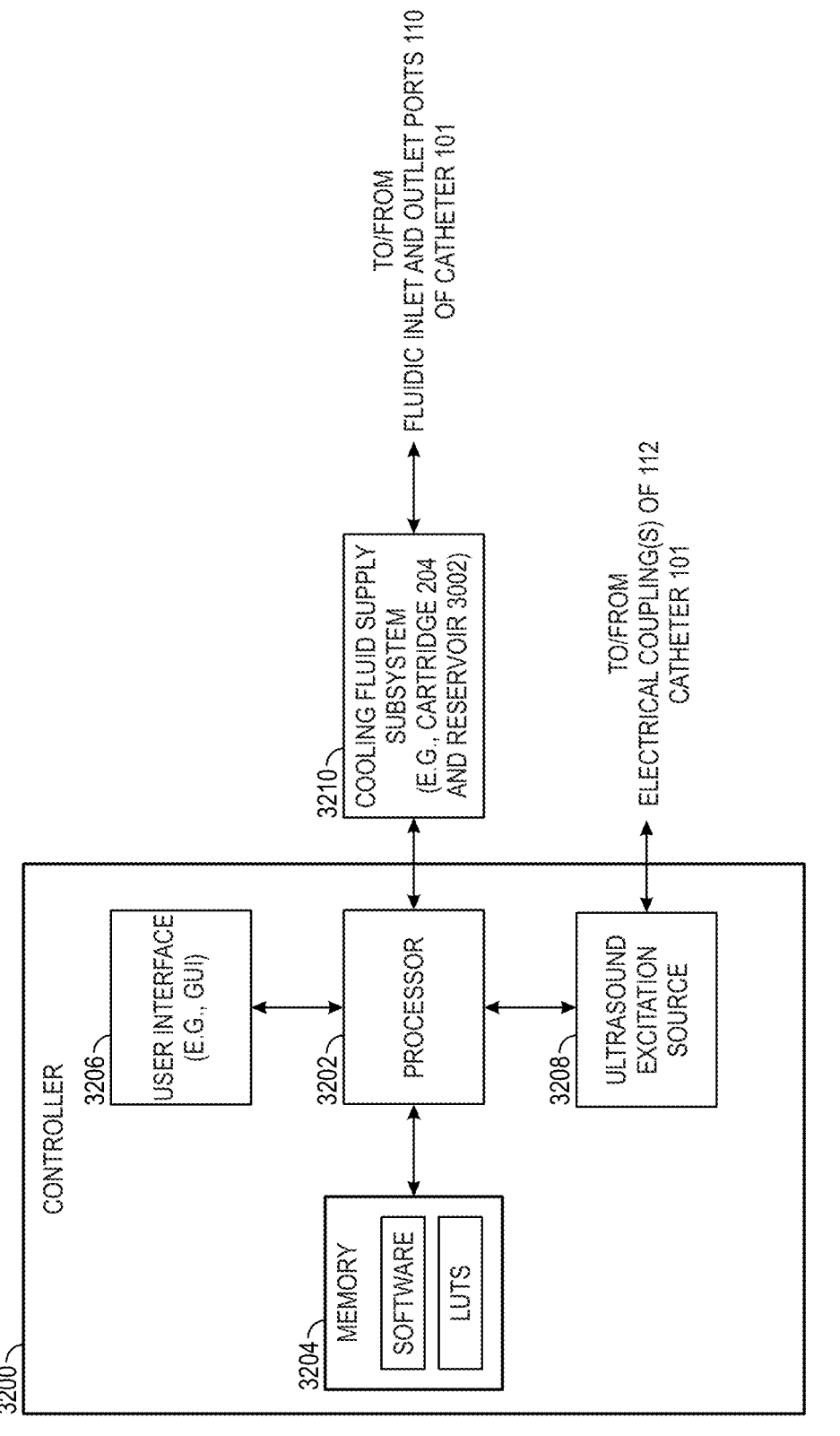
FIG. 32 is a block diagram of a controller of a treatment system, in accordance with an embodiment.

Referring to FIG. 32, a block diagram of a controller of a treatment system is shown in accordance with an embodiment. The block diagram represents an example implementation of the controller, which was introduced above. A controller 3200 is shown as including one or more processors 3202, a memory 3204, a user interface 3206, and an ultrasound excitation source 3208, but can include additional and/or alternative components. While not specifically shown, a processor 3202 can be located on a control board, or more generally, a printed circuit board (PCB) along with additional circuitry of the controller 3200. The processor 3202 can communicate with the memory 3204, which can include a non-transitory computer-readable medium storing instructions. The processor 3202 can execute the instructions to cause the treatment system 100 to perform the methods described herein. The user interface 3206 interacts with the processor 3202 to cause transmission of electrical signals at selected actuation frequencies to the ultrasound transducer 108 via wires of the connection cable and the cabling that extends through the catheter shaft 704. These wires electrically couple the controller 3200 to the transducer 108 so that the controller 3200 can send electrical signals to the transducer 108, and receive electrical signals from the transducer 108. The processor 3202 can control the ultrasound excitation source 3208 to control the amplitude and timing of the electrical signals so as to control the power level and duration of the ultrasound signals emitted by transducer 108. More generally, the controller 3200 can control one or more ultrasound treatment parameters that are used to perform sonication. In certain embodiments, the excitation source can also detect electrical signals generated by transducer 108 and communicate such signals to the processor 3202 and/or circuitry of a control board. While the ultrasound excitation source 3208 in FIG. 32 is shown as being part of the controller 3200, it is also possible that the ultrasound excitation source 3208 is external to the controller 3200 while still being controlled by the controller 3200, and more specifically, by the processor 3202 of the controller 3200.

The user interface 3206 can include a touch screen and/or buttons, switches, etc., to allow for an operator (user) to enter patient data, select treatment parameters, view records stored on a storage/retrieval unit (not shown), and/or otherwise communicate with the processor 3202. The user interface 3206 can include a voice-activated mechanism to enter patient data or may be able to communicate with additional equipment so that control of the controller 3200 is through a separate user interface 3206, such as a wired or wireless remote control. In some embodiments, the user interface 3206 is configured to receive operator-defined inputs, which can include, e.g., a duration of energy delivery, one or more other timing aspects of the energy delivery pulses (e.g., frequency, duty cycle, etc.), power, body lumen length, mode of operation, patient parameter, such as height and weight, and/or verification of artery diameter, or a combination thereof. Example modes of operation can include (but are not limited to): system initiation and set-up, catheter preparation, balloon inflation, verification of balloon apposition, pre-cooling, sonication, post-cooling, balloon deflation, and catheter removal, but are not limited thereto. In certain embodiments, the user interface 3206 provides a graphical user interface (GUI) that instructs a user how to properly operate the treatment system 100. The user interface 3206 can also be used to display treatment data for review and/or download, as well as to allow for software updates, and/or the like.

The controller 3200 can also control a cooling fluid supply subsystem 3210, which can include the fluid transfer cartridge 204 and fluid reservoir 3002, which were described above, but can include alternative types of fluid pumps, and/or the like. The cooling fluid supply subsystem 3210 is fluidically coupled to one or more fluid lumens (e.g., 110) within the catheter shaft which in turn are fluidically coupled to the balloon. The cooling fluid supply subsystem 3210 can be configured to circulate a cooling liquid through the catheter 101 to the transducer 108 in the balloon. The cooling fluid supply subsystem 3210 may include elements such as the fluid reservoir 3002 for holding the cooling fluid 603, pumps (e.g., syringes), a refrigerating coil (not shown), or the like for providing a supply of cooling fluid 603 to the interior space of the balloon at a controlled temperature, desirably at or below body temperature. The processor 3202 interfaces with the cooling fluid supply subsystem 3210 to control the flow of cooling fluid 603 into and out of the balloon. For example, the processor 3202 can control motor control devices linked to drive motors 1108 associated with pumps for controlling the speed of operation of pumps (e.g., syringes). Such motor control devices can be used, for example, where the pumps are positive displacement pumps, such as peristaltic pumps. Alternatively, or additionally, a control circuit may include structures such as controllable valves connected in the fluid circuit for varying resistance of the circuit to fluid flow (not shown). The processor 3202 can monitor pressure measurements obtained by the pressure sensors (e.g., P1, P2 and P3) to monitor and control the cooling fluid 603 through the catheter 101 and the balloon. The pressure sensors can also be used to determine if there is a blockage and/or a leak in the catheter 101. While the balloon is in an inflated state, the pressure sensors can be used to maintain a desired pressure in the balloon, e.g., at a pressure of between 10 psi and 30 psi, but not limited thereto. As will be described in additional detail below, the processor 3202 can use sensor measurements from one or more of the pressure sensors 2402 and/or other sensors to determine when the balloon is in apposition with a body lumen as well as to estimate an inner diameter of a body lumen in order to select an appropriate dose of ultrasound energy to be delivered to treat tissue surrounding the body lumen.

The controller 3200 can control operation of the generator 202 and fluid transfer cartridge 204 components to drive the inflation of the balloon prior to or during an interventional procedure. For example, the controller 3200 can control a priming process. The priming process can fill one or more of the syringes, the fluid manifold, the fluid conduit lines, and the balloon of the treatment system 100 with fluid, and remove bubbles from the system. More particularly, the priming process can purge air from the fluidic system and prepare the treatment system 100 for delivery into the patient. The priming process may, as described below, include expelling fluid from a return syringe before filling an injection syringe to avoid sending air into the injection syringe. The controller 3200 may also control the inflation procedure, as described above, by driving the syringe piston 702 vertically to move the stopper 608 within the syringe and thus draw fluid into or expel fluid out of the syringe.

A position of the stopper 608 within the syringe can be determined by the controller 3200 based on several sensor inputs. The controller 3200 can receive feedback from the motor 1108 that drives the syringe piston 702 to determine stopper position. For example, the motor 1108 can provide data corresponding to a number of rotations of the gear 804, and the controller 3200 can determine, based on the rotations and known thread pitch information, a distance that the stopper 608 has been moved within the syringe. Furthermore, as described above, a magnetic or optical sensor can detect a location of the shaft end 706, e.g., a home position 1102. When the shaft end 706 is at the home position 1102, the stopper 608 can be at a known location within the syringe.

Although the motor 1108 feedback and home position sensor(s) can provide precise determination of the home position 1102, system slippage in the gear teeth or motor 1108 can lead to some inaccuracy as to whether the stopper 608 is accurately located at a same home position 1102 after each inflation/deflation cycle. More particularly, as the piston is driven upward and downward within the syringe over several cycles, the shaft end 706 may be driven based on motor 1108 rotations to a different home position 1102 in which the homing sensor is not triggered. When this happens, an error may be generated by the system. However, there may be only a marginally different amount of fluid remaining in the syringe when the error is triggered, as compared to when the stopper 608 was at the original home position 1102, which could create a nuisance requiring the user to re-home the system even when there is no practical impact to the system efficacy.

To avoid such nuisances, a homing process can be used that will dynamically adjust the home position when changes in the home position do not negatively affect system operation, and to generate an error when the changes may negatively affect system operation.

In an operation, the fluid transfer cartridge 204 is loaded into the generator 202. When operation begins, the shaft end

706 of the fluid transfer cartridge 204 will either be detected by the homing sensor, or not. If the shaft end 706 is not detected, then the controller 3200 can determine that the syringe must be homed prior to proceeding with fluidic priming and/or balloon inflation/deflation. If the shaft end 706 is detected, then the syringe can already be determined to be homed.

In the first case, when the shaft end 706 is not initially detected, the controller 3200 can drive the motor 1108 to raise the syringe pistons 702 until the shaft end 706 is detected by the position sensors. This is the initial home position. The controller 3200 can set the encoder volumes to zero at the initial home position. More particularly, the controller 3200 can determine a position value of the motor 1108 encoders and the position value can be set as the initial home position (corresponding to the home position of shaft end 706).

Switches include always on, always off, and intermittent (between always on and always off) positions. In an embodiment, the shaft end 706, upon reaching the initial home position, can be in either the always on or intermittent positions. If the initial home position is in the always on position, then lowering and raising the shaft end 706 to the initial home position should trigger a home position sensor. If the initial home position is in the intermittent position, then lowering and raising the shaft end 706 to the initial home position may or may not trigger a home position sensor.

It will be appreciated that, by monitoring shaft end position and motor encoders, a comparison of shaft end 706 location and remaining fluid volume can be performed. For example, at any location, the motor 1108 encoder information can be used to determine a stopper position and, thus, how much cooling fluid 603 remains in the syringe. In an embodiment, when the home position sensor is triggered, the controller 3200 can determine a remaining fluid volume in the syringe. When the remaining fluid volume is less than a predetermined volume, e.g., 3 to 5 mL, when the shaft end 706 is detected by the position sensor, even if the motor encoder is not at the same location as the initial home position, then the controller 3200 may set the motor position as a new home position. Alternatively, if the remaining volume is greater than the predetermined volume, e.g., greater than 5 mL, then the controller 3200 may generate an error to require the user to troubleshoot and re-home the system. In either case, the motor encoder can be used to determine cooling fluid volumes within the syringe at all states of the priming and/or inflation/deflation processes.

In the second case, when the shaft end 706 is initially detected, the controller 3200 can drive the motor 1108 to lower the syringe piston 702 to draw a predetermined volume of cooling fluid 603, e.g., 3 to 5 mL, into the syringe. The home position sensor can be monitored during the lowering process. If the home position sensor turns off during the lowering movement, then the motor encoder position can be set as a new home position by the controller 3200. The controller 3200 may proceed to control the system to perform the priming and/or inflation/deflation processes. Alternatively, if the home position sensor is still on after lowering the syringe to draw the predetermined volume of cooling fluid 603 into the syringe, then the controller 3200 can generate an error to require the user to troubleshoot and re-home the system. More particularly, the sensor remaining on after the lowering of the syringe likely indicates that the sensor has malfunctioned and the user may be notified accordingly. In either case, the motor encoder can be driven to perform the priming and/or inflation/deflation processes.

Figure 33:
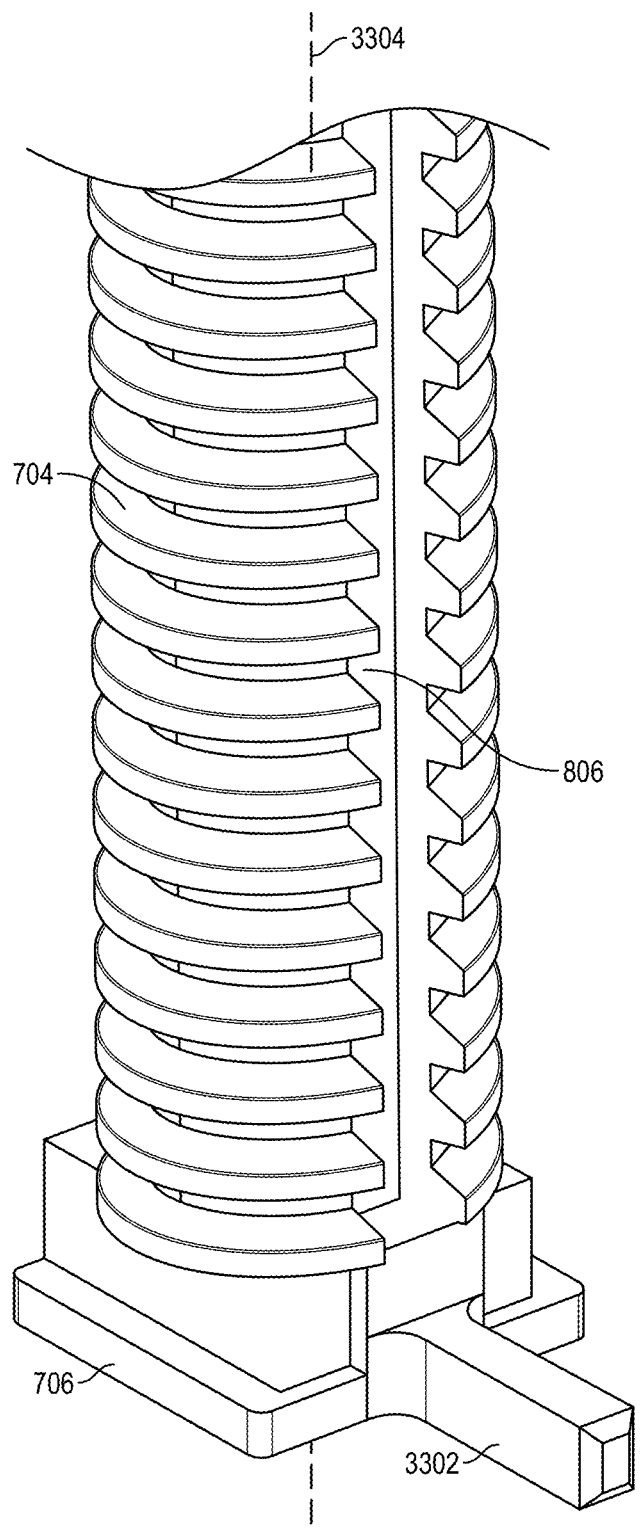
FIG. 33 is a perspective view of a shaft end having an optical tab, in accordance with an embodiment.

Referring to FIG. 33, a perspective view of a shaft end having an optical tab is shown in accordance with an embodiment. As described above, the shaft end 706 can include a feature to trigger the position sensor. For example, the feature can be an optical tab 3302, also referred to as an optical feature. The optical tab 3302 can include a tab, prong, flag, etc., to trigger an optical sensor. In an embodiment, the optical tab 3302 extends radially outward from a shaft axis 3304. The shaft axis 3304 can be a longitudinal axis of the shaft 704. The radial extension can protrude outward such that light emitted by the optical sensor in a direction transverse to the shaft axis 3304 can reflect from the optical tab 3302 when the shaft end 706 is adjacent to the optical sensor. Accordingly, the optical tab 3302 can block the optical sensor to trigger the sensor and indicate to the controller 3200 that the shaft 704 and the stopper 608 are at a particular position.

Embodiments of a treatment system are described above. More particularly, embodiments of the treatment system are described, either explicitly or implicitly. The following paragraphs summarize some of the described embodiments.

In an embodiment, a fluid transfer cartridge includes a cartridge shell defining a cartridge cavity between a front face and a rear face. The front face includes an opening. The fluid transfer cartridge includes a handle extending from the front face of the cartridge shell over the opening. The fluid transfer cartridge includes a syringe barrel disposed within the cartridge cavity and visibly exposed through the opening on a first side of the handle.

In an embodiment, the fluid transfer cartridge includes a second syringe barrel disposed within the cartridge cavity and visibly exposed through the opening on a second side of the handle.

In an embodiment, the handle extends vertically from an upper end of the opening to a lower end of the opening.

In an embodiment, the syringe barrel has a syringe axis extending vertically within the cartridge cavity.

In an embodiment, the fluid transfer cartridge includes a light source within the cartridge cavity. The light source is directed through the syringe barrel.

In an embodiment, the light source is directed through an end face of the syringe barrel.

In an embodiment, the light source emits a blue light.

In an embodiment, the light source emits a first color of light when the syringe barrel is filled with a first volume of fluid. The light source emits a second color of light when the syringe barrel is filled with a second volume of fluid.

In an embodiment, the fluid transfer cartridge includes a syringe holder mounted within the cartridge cavity. The syringe holder holds the syringe barrel such that rotation of the syringe barrel relative to the cartridge shell is limited.

In an embodiment, the cartridge cavity is defined between the front face, the rear face, an upper face, and a bottom face, and further including a syringe piston disposed within the syringe barrel. The syringe piston includes a stopper and a shaft extending from the stopper to a shaft end. The shaft end is flush with the bottom face when the stopper is at a home position in the syringe barrel. The shaft end is below the bottom face when the stopper is at an end position in the syringe barrel.

In an embodiment, the shaft includes an external thread, and further including a gear mounted on the cartridge shell. The gear includes an internal thread engaging the external thread.

In an embodiment, the external thread and the internal thread have different working depths.

In an embodiment, the shaft includes a notch extending longitudinally between the stopper and the shaft end.

In an embodiment, the syringe piston includes an optical tab disposed on the shaft at the shaft end.

In an embodiment, the rear face includes a boss. The fluid transfer cartridge includes one or more electrical contact pads exposed through the rear face near an upper end of the boss.

In an embodiment, the boss includes four or more recesses distributed around a boss perimeter of the boss.

In an embodiment, the cartridge shell includes a conduit routing plate engaging the front face along an edge. The conduit routing plate and the front face include respective notches at the edge. The respective notches combine to form a conduit routing port through which a fluid conduit is routed.

In an embodiment, a treatment system includes a fluid transfer cartridge including a cartridge shell defining a cartridge cavity between a front face and a rear face. The front face includes an opening, a handle extending from the front face of the cartridge shell over the opening, and a syringe barrel disposed within the cartridge cavity and visibly exposed through the opening on a first side of the handle. The treatment system includes a generator having a generator housing including a cartridge receptacle configured to receive the fluid transfer cartridge.

In an embodiment, the cartridge cavity is defined between the front face, the rear face, an upper face, and a bottom face, and further including a syringe piston disposed within the syringe barrel. The syringe piston includes a stopper and a shaft extending from the stopper to a shaft end. The shaft end is flush with the bottom face when the stopper is at a home position in the syringe barrel. The shaft end is below the bottom face when the stopper is at an end position in the syringe barrel.

In an embodiment, the generator includes an optical switch. The shaft includes an optical tab to block the optical switch to indicate a position of the shaft.

In an embodiment, the generator includes one or more processors configured to determine, based on the position of the shaft, a travel of the one or more syringes.

In an embodiment, the travel of the one or more syringes includes a home position of the syringe piston in which the syringe piston removes bubbles from the one or more syringes.

In an embodiment, the generator includes a motor operably coupled to the shaft. The one or more processors are configured to actuate the motor to move the syringe piston during preparation of the syringe for fluid transfer.

In an embodiment, the one or more processors are configured to drive the motor to fill the syringe with a cooling fluid. The one or more processors are configured to determine the syringe is filled with a predetermined amount of the cooling fluid. The one or more processors are configured to drive the motor to empty the cooling fluid from the syringe. The one or more processors are configured to determine the syringe is empty.

In an embodiment, a fluid transfer cartridge shell includes a front face having a front face perimeter and a handle extending over an opening. The fluid transfer cartridge shell includes a rear face having a rear face perimeter. When the front face perimeter is engaged to the rear face perimeter a cartridge cavity is defined between the front face and the rear face such that the cartridge cavity is visibly exposed through the opening on a first side of the handle.

In an embodiment, the handle extends vertically from an upper end of the opening to a lower end of the opening.

In an embodiment, the fluid transfer cartridge shell includes a light source within the cartridge cavity. The light source emits a blue light.

In an embodiment, the rear face includes a boss. The generator includes one or more electrical contact pads exposed through the rear face near an upper end of the boss.

In an embodiment, the boss includes four or more recesses distributed around a boss perimeter of the boss.

In an embodiment, the cartridge shell includes a conduit routing plate engaging the front face along an edge. The conduit routing plate and the front face include respective notches at the edge, the respective notches combining to form a conduit routing port through which a fluid conduit is routed.

In an embodiment, a fluid transfer cartridge includes a cartridge shell having a cartridge cavity between a front face and a rear face. The fluid transfer cartridge includes a syringe barrel disposed within the cartridge cavity and having a syringe cavity. The fluid transfer cartridge includes a cartridge manifold in the cartridge cavity. The cartridge manifold includes a fluid transfer plate having a front fluid channel in a front plate surface, a rear fluid channel in a rear plate surface, and a fluid port extending through the fluid transfer plate from the front fluid channel to the rear fluid channel. The front fluid channel, the rear fluid channel, and the fluid port are in fluid communication with the syringe cavity.

In an embodiment, the cartridge manifold includes a piston having an end seal. The piston is movable from an open position in which the end seal unseals the fluid port to allow cooling fluid to pass through the fluid port to a closed position in which the end seal seals the fluid port to stop the cooling fluid from passing through the fluid port.

In an embodiment, the end seal has a circular distal surface.

In an embodiment, the end seal includes an O-ring.

In an embodiment, the cartridge manifold includes an aft plate apposed to the rear plate surface of the fluid transfer plate. The cartridge manifold includes a channel seal extending around the rear fluid channel. The channel seal is sandwiched between the rear plate surface and the aft plate.

In an embodiment, a rear surface of the piston is rearward of a back surface of the aft plate in the closed position and the open position.

In an embodiment, the end seal presses against the rear plate surface of the fluid transfer plate and a side seal to seal against the aft plate.

In an embodiment, the piston is spring-loaded to move the piston from the open position to the closed position.

In an embodiment, the piston includes an annular groove to receive a spring to spring-load the piston.

In an embodiment, the fluid transfer plate is sandwiched between a fore plate and the aft plate. The fore plate is snap fit to the aft plate.

In an embodiment, a treatment system includes a fluid transfer cartridge including a cartridge shell having a cartridge cavity between a front face and a rear face, a syringe barrel disposed within the cartridge cavity and having a syringe cavity, and a cartridge manifold in the cartridge cavity. The cartridge manifold includes a fluid transfer plate having a front fluid channel in a front plate surface, a rear fluid channel in a rear plate surface, and a fluid port extending through the fluid transfer plate from the front fluid channel to the rear fluid channel. The front fluid channel, the rear fluid channel, and the fluid port are in fluid communication with the syringe cavity, and a generator having a generator housing including a cartridge receptacle configured to receive the fluid transfer cartridge.

In an embodiment, the cartridge manifold includes a piston having an end seal. The piston is movable from an open position in which the end seal unseals the fluid port to allow cooling fluid to pass through the fluid port to a closed position in which the end seal seals the fluid port to stop the cooling fluid from passing through the fluid port.

In an embodiment, the end seal has a circular distal surface.

In an embodiment, the end seal includes an O-ring.

In an embodiment, the cartridge manifold includes an aft plate apposed to the rear plate surface of the fluid transfer plate. The cartridge manifold includes a channel seal extending around the rear fluid channel. The channel seal is sandwiched between the rear plate surface and the aft plate.

In an embodiment, a rear surface of the piston is rearward of a back surface of the aft plate in the closed position and the open position.

In an embodiment, the end seal presses against the rear plate surface of the fluid transfer plate and a side seal to seal against the aft plate.

In an embodiment, the piston is spring-loaded to move the piston from the open position to the closed position.

In an embodiment, the piston includes an annular groove to receive a spring to spring-load the piston.

In an embodiment, the fluid transfer plate is sandwiched between a fore plate and the aft plate. The fore plate is snap fit to the aft plate.

In an embodiment, a cartridge manifold includes a fluid transfer plate having a front fluid channel in a front plate surface, a rear fluid channel in a rear plate surface, and a fluid port extending through the fluid transfer plate from the front fluid channel to the rear fluid channel. The cartridge manifold includes a piston having an end seal. The piston is movable from an open position in which the end seal unseals the fluid port to allow cooling fluid to pass through the fluid port to a closed position in which the end seal seals the fluid port to stop the cooling fluid from passing through the fluid port.

In an embodiment, the end seal has a circular distal surface.

In an embodiment, the end seal includes an O-ring.

In an embodiment, the cartridge manifold includes an aft plate apposed to the rear plate surface of the fluid transfer plate. The cartridge manifold includes a channel seal extending around the rear fluid channel. The channel seal is sandwiched between the rear plate surface and the aft plate.

In an embodiment, a rear surface of the piston is rearward of a back surface of the aft plate in the closed position and the open position.

In an embodiment, the end seal presses against the rear plate surface of the fluid transfer plate and a side seal to seal against the aft plate.

In an embodiment, the piston is spring-loaded to move the piston from the open position to the closed position.

In an embodiment, the piston includes an annular groove to receive a spring to spring-load the piston.

In an embodiment, the fluid transfer plate is sandwiched between a fore plate and the aft plate. The fore plate is snap fit to the aft plate.

In an embodiment, a fluid transfer cartridge for an ultrasound-based treatment system includes a cartridge shell defining a cartridge cavity between a front face and a rear face. The front face includes an opening. The fluid transfer cartridge includes a handle extending from the front face of the cartridge shell over the opening. The fluid transfer cartridge includes a syringe barrel disposed within the cartridge cavity and visibly exposed through the opening on a first side of the handle.

In an embodiment, the fluid transfer cartridge includes a second syringe barrel disposed within the cartridge cavity and visibly exposed through the opening on a second side of the handle.

In an embodiment, the handle extends vertically from an upper end of the opening to a lower end of the opening.

In an embodiment, the syringe barrel has a syringe axis extending vertically within the cartridge cavity.

In an embodiment, a fluid transfer cartridge for an ultrasound-based treatment system includes a cartridge shell defining a cartridge cavity between a front face and a rear face. The front face includes a window. The fluid transfer cartridge includes a handle extending from the front face of the cartridge shell over the window. The fluid transfer cartridge includes a syringe barrel disposed within the cartridge cavity and visibly exposed through the opening on a first side of the handle.

In an embodiment, the fluid transfer cartridge includes a second syringe barrel disposed within the cartridge cavity and visibly exposed through the window on a second side of the handle.

In an embodiment, the handle extends vertically from an upper end of the window to a lower end of the window.

In an embodiment, the syringe barrel has a syringe axis extending vertically within the cartridge cavity.

In an embodiment, a fluid transfer cartridge for an ultrasound-based treatment system includes a cartridge shell defining a cartridge cavity between a front face and a rear face. The fluid transfer cartridge includes a syringe barrel visibly exposed within the cartridge cavity. The fluid transfer cartridge includes a light source within the cartridge cavity. The light source is directed through an end face of the syringe barrel.

In an embodiment, the light source emits a blue light.

In an embodiment, the light source emits a first color of light when the syringe barrel is filled with a first volume of fluid. The light source emits a second color of light when the syringe barrel is filled with a second volume of fluid.

In an embodiment, a fluid transfer cartridge for an ultrasound-based treatment system includes a cartridge shell defining a cartridge cavity between a front face and a rear face. The fluid transfer cartridge includes a syringe barrel visibly exposed within the cartridge cavity. The fluid transfer cartridge includes a light source within the cartridge cavity. The light source is directed through the syringe barrel.

In an embodiment, the light source emits a blue light.

In an embodiment, the light source emits a first color of light when the syringe barrel is filled with a first volume of fluid. The light source emits a second color of light when the syringe barrel is filled with a second volume of fluid.

In an embodiment, a fluid transfer cartridge for an ultrasound-based treatment system includes a cartridge shell defining a cartridge cavity between a front face and a rear face. The fluid transfer cartridge includes a syringe barrel visibly exposed within the cartridge cavity. The fluid transfer cartridge includes a syringe holder mounted within the cartridge cavity. The syringe holder holds the syringe barrel such that rotation of the syringe barrel relative to the cartridge shell is limited.

In an embodiment, a fluid transfer cartridge includes a cartridge shell defining a cartridge cavity between a front face and a rear face. The fluid transfer cartridge includes one or more syringes disposed within the cartridge cavity. The one or more syringes each includes a syringe piston disposed within a syringe barrel. The syringe piston includes a stopper and a shaft extending from the stopper to a shaft end. The shaft end is disposed within the cartridge cavity when the stopper is at a home position in the syringe barrel. The shaft end is disposed outside of the cartridge cavity when the stopper is at an end position in the syringe barrel.

In an embodiment, the shaft includes an external thread. The fluid transfer cartridge includes a gear mounted on the cartridge shell. The gear includes an internal thread engaging the external thread.

In an embodiment, the shaft includes a notch extending longitudinally between the stopper and the shaft end.

In an embodiment, a fluid transfer cartridge includes a cartridge shell defining a cartridge cavity between a front face and a rear face. The fluid transfer cartridge includes one or more syringes disposed within the cartridge cavity. The one or more syringes each includes a syringe piston disposed within a syringe barrel. The syringe piston includes a stopper and a shaft extending from the stopper to a shaft end. The syringe piston includes a magnet disposed on the shaft at the shaft end.

In an embodiment, the magnet moves contacts of a magnetic switch of the treatment system to indicate proximity between the magnet and the magnetic switch.

In an embodiment, the treatment system includes one or more processors configured to determine, based on proximity between the magnet and the magnetic switch, a travel of the one or more syringes.

In an embodiment, the travel of the one or more syringes includes a home position of the syringe piston in which the syringe piston removes bubbles from the one or more syringes.

In an embodiment, the one or more processors are configured to actuate a motor operably coupled to the shaft to move the syringe piston during preparation of the one or more syringes for fluid transfer.

In an embodiment, the one or more processors are configured to: drive the motor to fill the one or more syringes with a cooling fluid; determine the one or more syringes are filled with a predetermined amount of the cooling fluid; drive the motor to empty the cooling fluid from the one or more syringes; and determine the one or more syringes are empty.

In an embodiment, a method includes filling several syringes of a fluid transfer cartridge with cooling fluid. The several syringes each includes a syringe piston disposed within a syringe barrel. The syringe piston includes a stopper and a shaft extending from the stopper to a shaft end. The shaft end is disposed within a cartridge cavity of the fluid transfer cartridge when the stopper is at a home position in the syringe barrel. The shaft end is disposed outside of the cartridge cavity when the stopper is at an end position in the syringe barrel. The method includes determining, by one or more processors, when the several syringes are filled with a predetermined amount of the cooling fluid based on the stopper being in the end position. The method includes filling a fluid path of the cartridge with the cooling fluid. The method includes removing bubbles from the fluid path and the several syringes.

In an embodiment, determining whether the several syringes are filled with the predetermined amount of cooling fluid includes detecting whether the stopper is in the end position.

In an embodiment, removing bubbles from the fluid path and the several syringes includes: filling the several syringes with the cooling fluid; determining the several syringes are filled with the cooling fluid based on the stopper being in the end position; emptying the cooling fluid from the several syringes; determining the several syringes are empty based on the stopper being in the home position; and filling the several syringes with the cooling fluid.

In an embodiment, a fluid transfer cartridge includes a cartridge shell defining a cartridge cavity between a front face and a rear face. The fluid transfer cartridge includes one or more syringes disposed within the cartridge cavity. The one or more syringes each includes a syringe piston disposed within a syringe barrel. The syringe piston includes a stopper and a shaft extending from the stopper to a shaft end. The shaft end is configured to emit or reflect light.

In an embodiment, the shaft end emits or reflects light to a light sensor of the treatment system to indicate proximity between the shaft end and the light sensor.

In an embodiment, the treatment system includes one or more processors configured to determine, based on proximity between the shaft end and the light sensor, a travel of the one or more syringes.

In an embodiment, the travel of the one or more syringes includes a home position of the syringe piston in which the syringe piston removes bubbles from the one or more syringes.

In an embodiment, the one or more processors are configured to actuate a motor operably coupled to the shaft to move the syringe piston during preparation of the one or more syringes for fluid transfer.

In an embodiment, the one or more processors are configured to: drive the motor to fill the one or more syringes with a cooling fluid; determine the one or more syringes are filled with a predetermined amount of the cooling fluid; drive the motor to empty the cooling fluid from the one or more syringes; and determine the one or more syringes are empty.

In an embodiment, a method includes filling several syringes of a fluid transfer cartridge with cooling fluid. The several syringes each includes a syringe piston disposed within a syringe barrel. The syringe piston includes a stopper and a shaft extending from the stopper to a shaft end. The shaft end is disposed within a cartridge cavity of the fluid transfer cartridge when the stopper is at a home position in the syringe barrel. The shaft end is disposed outside of the cartridge cavity when the stopper is at an end position in the syringe barrel. The method includes determining, by one or more processors, when the several syringes are filled with a predetermined amount of the cooling fluid based on the stopper being in the end position. The method includes filling a fluid path of the cartridge with the cooling fluid. The method includes removing bubbles from the fluid path and the several syringes.

In an embodiment, determining whether the several syringes are filled with the predetermined amount of cooling fluid includes detecting whether the stopper is in the end position.

In an embodiment, removing bubbles from the fluid path and the several syringes includes: filling the several syringes with the cooling fluid; determining the several syringes are filled with the cooling fluid based on the stopper being in the end position; emptying the cooling fluid from the several syringes; determining the several syringes are empty based on the stopper being in the home position; and filling the several syringes with the cooling fluid.

In an embodiment, a fluid transfer cartridge includes a cartridge shell defining a cartridge cavity between a front face and a rear face. The rear face includes a boss. The fluid transfer cartridge includes one or more spring-loaded electrical contact pins exposed through the rear face near an upper end of the boss.

In an embodiment, the boss includes four or more recesses distributed around a boss perimeter of the boss.

In an embodiment, the cartridge shell includes a conduit routing plate engaging the front face along an edge. The conduit routing plate and the front face include respective notches at the edge. The respective notches combine to form a conduit routing port through which a fluid conduit is routed.

In an embodiment, a generator for an ultrasound-based treatment system includes a generator housing having a cartridge receptacle configured to receive a fluid transfer cartridge. The generator includes a fastening mechanism including a release button movable between a latched position and an unlatched position. The generator includes several spring-loaded catches operably coupled to the release button such that moving the release button from the latched position to the unlatched position causes the several spring-loaded catches to move out of the cartridge receptacle.

In an embodiment, the cartridge receptacle includes a back recess to receive a boss of the fluid transfer cartridge. The back recess has a recess perimeter. The several spring-loaded catches includes four or more spring-loaded catches distributed around the recess perimeter.

In an embodiment, a generator for an ultrasound-based treatment system includes a generator housing having a cartridge receptacle configured to receive a fluid transfer cartridge. The generator includes a fastening mechanism including a release button movable between a latched position and an unlatched position. The generator includes one or more catches operably coupled to the release button such that moving the release button from the latched position to the unlatched position causes the one or more catches to move out of the cartridge receptacle.

In an embodiment, the generator includes one or more springs operably coupled to the release button to bias the release button toward the latched position.

In an embodiment, the one or more springs includes a single spring. The one or more catches includes several catches. The release button is operably coupled to a linkage that interconnects the several catches to the single spring to bias the several catches into the cartridge receptacle.

In an embodiment, the cartridge receptacle includes a back recess to receive a boss of the fluid transfer cartridge. The back recess has a recess perimeter. The one or more catches includes four or more spring-loaded catches distributed around the recess perimeter.

In an embodiment, a generator for an ultrasound-based treatment system includes a generator housing having a cartridge receptacle configured to receive a fluid transfer cartridge. The generator includes a well below the cartridge receptacle to receive a syringe piston of the fluid transfer cartridge.

In an embodiment, the generator includes one or more magnetic switches mounted within the well to detect a magnet disposed on the syringe piston of the fluid transfer cartridge.

In an embodiment, an ultrasound-based treatment system includes a generator having a cartridge receptacle. The ultrasound-based treatment system includes a fluid transfer cartridge. The ultrasound-based treatment system includes one or more processors configured to determine whether the fluid transfer cartridge is received within the cartridge receptacle, and activate, in response to determining that the fluid transfer cartridge is received within the cartridge receptacle, a light source of the fluid transfer cartridge. The light source is directed toward a syringe of the fluid transfer cartridge.

In an embodiment, the generator includes an electrical connector, and an indicator light. The one or more processors are configured to determine whether the electrical connector is electrically connected to an external connector, and change, in response to determining that the electrical connector is connected to the external connector, a lighting mode of the indicator light.

In an embodiment, the change in the lighting mode is from a first lighting mode in which the indicator light intermittently emits light to a second lighting mode in which the indicator light continuously emits light.

In an embodiment, the change in the lighting mode is from a first lighting mode in which the indicator light emits a first color of light to a second lighting mode in which the indicator light emits a second color of light.

In an embodiment, the indicator light includes an indicator light ring extending around the electrical connector.

In an embodiment, a fluid transfer cartridge for an ultrasound-based treatment system, includes a cartridge shell defining a cartridge cavity between a front face and a rear face. The front face includes an opening. The fluid transfer cartridge includes a handle extending from the front face of the cartridge shell over the opening. The fluid transfer cartridge includes a syringe barrel disposed within the cartridge cavity and visibly exposed through the opening on a first side of the handle.

In an embodiment, the fluid transfer cartridge includes a second syringe barrel disposed within the cartridge cavity and visibly exposed through the opening on a second side of the handle.

In an embodiment, the handle extends vertically from an upper end of the opening to a lower end of the opening.

In an embodiment, the syringe barrel has a syringe axis extending vertically within the cartridge cavity.

In an embodiment, a fluid transfer cartridge for an ultrasound-based treatment system includes a cartridge shell defining a cartridge cavity between a front face and a rear face. The front face includes a window. The fluid transfer cartridge includes a handle extending from the front face of the cartridge shell over the window. The fluid transfer cartridge includes a syringe barrel disposed within the cartridge cavity and visibly exposed through the opening on a first side of the handle.

In an embodiment, the fluid transfer cartridge includes a second syringe barrel disposed within the cartridge cavity and visibly exposed through the window on a second side of the handle.

In an embodiment, the handle extends vertically from an upper end of the window to a lower end of the window.

In an embodiment, the syringe barrel has a syringe axis extending vertically within the cartridge cavity.

In an embodiment, a fluid transfer cartridge for an ultrasound-based treatment system includes a cartridge shell defining a cartridge cavity between a front face and a rear face. The fluid transfer cartridge includes a syringe barrel visibly exposed within the cartridge cavity. The fluid transfer cartridge includes a light source within the cartridge cavity. The light source is directed through an end face of the syringe barrel.

In an embodiment, the light source emits a blue light.

In an embodiment, the light source emits a first color of light when the syringe barrel is filled with a first volume of fluid. The light source emits a second color of light when the syringe barrel is filled with a second volume of fluid.

In an embodiment, a fluid transfer cartridge for an ultrasound-based treatment system includes a cartridge shell defining a cartridge cavity between a front face and a rear face. The fluid transfer cartridge includes a syringe barrel visibly exposed within the cartridge cavity. The fluid transfer cartridge includes a light source within the cartridge cavity. The light source is directed through the syringe barrel.

In an embodiment, the light source emits a blue light.

In an embodiment, the light source emits a first color of light when the syringe barrel is filled with a first volume of fluid. The light source emits a second color of light when the syringe barrel is filled with a second volume of fluid.

In an embodiment, a fluid transfer cartridge for an ultrasound-based treatment system includes a cartridge shell defining a cartridge cavity between a front face and a rear face. The fluid transfer cartridge includes a syringe barrel visibly exposed within the cartridge cavity. The fluid transfer cartridge includes a syringe holder mounted within the cartridge cavity. The syringe holder holds the syringe barrel such that rotation of the syringe barrel relative to the cartridge shell is limited.

In an embodiment, a fluid transfer cartridge includes a cartridge shell defining a cartridge cavity between a front face and a rear face. The fluid transfer cartridge includes one or more syringes disposed within the cartridge cavity. The one or more syringes each includes a syringe piston disposed within a syringe barrel. The syringe piston includes a stopper and a shaft extending from the stopper to a shaft end. The shaft end is disposed within the cartridge cavity when the stopper is at a home position in the syringe barrel. The shaft end is disposed outside of the cartridge cavity when the stopper is at an end position in the syringe barrel.

In an embodiment, the shaft includes an external thread. The fluid transfer cartridge includes a gear mounted on the cartridge shell. The gear includes an internal thread engaging the external thread.

In an embodiment, the shaft includes a notch extending longitudinally between the stopper and the shaft end.

In an embodiment, a fluid transfer cartridge includes a cartridge shell defining a cartridge cavity between a front face and a rear face. The fluid transfer cartridge includes one or more syringes disposed within the cartridge cavity. The one or more syringes each includes a syringe piston disposed within a syringe barrel. The syringe piston includes a stopper and a shaft extending from the stopper to a shaft end. The syringe piston includes a magnet disposed on the shaft at the shaft end.

In an embodiment, the magnet moves contacts of a magnetic switch of the treatment system to indicate proximity between the magnet and the magnetic switch.

In an embodiment, the treatment system includes one or more processors configured to determine, based on proximity between the magnet and the magnetic switch, a travel of the one or more syringes.

In an embodiment, the travel of the one or more syringes includes a home position of the syringe piston in which the syringe piston removes bubbles from the one or more syringes.

In an embodiment, the one or more processors are configured to actuate a motor operably coupled to the shaft to move the syringe piston during preparation of the one or more syringes for fluid transfer.

In an embodiment, the one or more processors are configured to: drive the motor to fill the one or more syringes with a cooling fluid; determine the one or more syringes are filled with a predetermined amount of the cooling fluid; drive the motor to empty the cooling fluid from the one or more syringes; and determine the one or more syringes are empty.

In an embodiment, a method includes filling several syringes of a fluid transfer cartridge with cooling fluid. The several syringes each includes a syringe piston disposed within a syringe barrel. The syringe piston includes a stopper and a shaft extending from the stopper to a shaft end. The shaft end is disposed within a cartridge cavity of the fluid transfer cartridge when the stopper is at a home position in the syringe barrel. The shaft end is disposed outside of the cartridge cavity when the stopper is at an end position in the syringe barrel. The method includes determining, by one or more processors, when the several syringes are filled with a predetermined amount of the cooling fluid based on the stopper being in the end position. The method includes filling a fluid path of the cartridge with the cooling fluid. The method includes removing bubbles from the fluid path and the several syringes.

In an embodiment, determining whether the several syringes are filled with the predetermined amount of cooling fluid includes detecting whether the stopper is in the end position.

In an embodiment, removing bubbles from the fluid path and the several syringes includes: filling the several syringes with the cooling fluid; determining the several syringes are filled with the cooling fluid based on the stopper being in the end position; emptying the cooling fluid from the several syringes; determining the several syringes are empty based on the stopper being in the home position; and filling the several syringes with the cooling fluid.

In an embodiment, a fluid transfer cartridge includes a cartridge shell defining a cartridge cavity between a front face and a rear face; one or more syringes disposed within the cartridge cavity. The one or more syringes each includes a syringe piston disposed within a syringe barrel. The syringe piston includes a stopper and a shaft extending from the stopper to a shaft end. The shaft end is configured to emit or reflect light.

In an embodiment, the shaft end emits or reflects light to a light sensor of the treatment system to indicate proximity between the shaft end and the light sensor.

In an embodiment, the treatment system includes one or more processors configured to determine, based on proximity between the shaft end and the light sensor, a travel of the one or more syringes.

In an embodiment, the travel of the one or more syringes includes a home position of the syringe piston in which the syringe piston removes bubbles from the one or more syringes.

In an embodiment, the one or more processors are configured to actuate a motor operably coupled to the shaft to move the syringe piston during preparation of the one or more syringes for fluid transfer.

In an embodiment, the one or more processors are configured to: drive the motor to fill the one or more syringes with a cooling fluid; determine the one or more syringes are filled with a predetermined amount of the cooling fluid; drive the motor to empty the cooling fluid from the one or more syringes; and determine the one or more syringes are empty.

In an embodiment, a method includes filling several syringes of a fluid transfer cartridge with cooling fluid. The several syringes each includes a syringe piston disposed within a syringe barrel. The syringe piston includes a stopper and a shaft extending from the stopper to a shaft end. The shaft end is disposed within a cartridge cavity of the fluid transfer cartridge when the stopper is at a home position in the syringe barrel. The shaft end is disposed outside of the cartridge cavity when the stopper is at an end position in the syringe barrel. The method includes determining, by one or more processors, when the several syringes are filled with a predetermined amount of the cooling fluid based on the stopper being in the end position. The method includes filling a fluid path of the cartridge with the cooling fluid. The method includes removing bubbles from the fluid path and the several syringes.

In an embodiment, determining whether the several syringes are filled with the predetermined amount of cooling fluid includes detecting whether the stopper is in the end position.

In an embodiment, removing bubbles from the fluid path and the several syringes includes: filling the several syringes with the cooling fluid; determining the several syringes are filled with the cooling fluid based on the stopper being in the end position; emptying the cooling fluid from the several syringes; determining the several syringes are empty based on the stopper being in the home position; and filling the several syringes with the cooling fluid.

In an embodiment, a fluid transfer cartridge includes a cartridge shell defining a cartridge cavity between a front face and a rear face. The rear face includes a boss. The fluid transfer cartridge includes one or more spring-loaded electrical contact pins exposed through the rear face near an upper end of the boss.

In an embodiment, the boss includes four or more recesses distributed around a boss perimeter of the boss.

In an embodiment, the cartridge shell includes a conduit routing plate engaging the front face along an edge. The conduit routing plate and the front face include respective notches at the edge, the respective notches combining to form a conduit routing port through which a fluid conduit is routed.

In an embodiment, a generator for an ultrasound-based treatment system includes a generator housing having a cartridge receptacle configured to receive a fluid transfer cartridge. The generator includes a fastening mechanism including a release button movable between a latched position and an unlatched position, and several spring-loaded catches operably coupled to the release button such that moving the release button from the latched position to the unlatched position causes the several spring-loaded catches to move out of the cartridge receptacle.

In an embodiment, the cartridge receptacle includes a back recess to receive a boss of the fluid transfer cartridge. The back recess has a recess perimeter. The several spring-loaded catches includes four or more spring-loaded catches distributed around the recess perimeter.

In an embodiment, a generator for an ultrasound-based treatment system includes a generator housing having a cartridge receptacle configured to receive a fluid transfer cartridge. The generator includes a fastening mechanism including a release button movable between a latched position and an unlatched position, and one or more catches operably coupled to the release button such that moving the release button from the latched position to the unlatched position causes the one or more catches to move out of the cartridge receptacle.

In an embodiment, the generator includes one or more springs operably coupled to the release button to bias the release button toward the latched position.

In an embodiment, the one or more springs includes a single spring. The one or more catches includes several catches. The release button is operably coupled to a linkage that interconnects the several catches to the single spring to bias the several catches into the cartridge receptacle.

In an embodiment, the cartridge receptacle includes a back recess to receive a boss of the fluid transfer cartridge. The back recess has a recess perimeter. The one or more catches includes four or more spring-loaded catches distributed around the recess perimeter.

In an embodiment, a generator for an ultrasound-based treatment system includes a generator housing having a cartridge receptacle configured to receive a fluid transfer cartridge. The generator includes a well below the cartridge receptacle to receive a syringe piston of the fluid transfer cartridge.

In an embodiment, the generator includes one or more magnetic switches mounted within the well to detect a magnet disposed on the syringe piston of the fluid transfer cartridge.

In an embodiment, an ultrasound-based treatment system includes a generator having a cartridge receptacle. The ultrasound-based treatment system includes a fluid transfer cartridge. The ultrasound-based treatment system includes one or more processors configured to determine whether the fluid transfer cartridge is received within the cartridge receptacle, and activate, in response to determining that the fluid transfer cartridge is received within the cartridge receptacle, a light source of the fluid transfer cartridge. The light source is directed toward a syringe of the fluid transfer cartridge.

In an embodiment, the generator includes an electrical connector, and an indicator light. The one or more processors are configured to determine whether the electrical connector is electrically connected to an external connector, and change, in response to determining that the electrical connector is connected to the external connector, a lighting mode of the indicator light.

In an embodiment, the change in the lighting mode is from a first lighting mode in which the indicator light intermittently emits light to a second lighting mode in which the indicator light continuously emits light.

In an embodiment, the change in the lighting mode is from a first lighting mode in which the indicator light emits a first color of light to a second lighting mode in which the indicator light emits a second color of light.

In an embodiment, the indicator light includes an indicator light ring extending around the electrical connector.

In an embodiment, a fluid transfer cartridge for an ultrasound-based treatment system includes a cartridge shell having a cartridge cavity between a front face and a rear face. The fluid transfer cartridge includes a syringe barrel disposed within the cartridge cavity and having a syringe cavity. The fluid transfer cartridge includes a cartridge manifold in the cartridge cavity. The cartridge manifold includes a fluid transfer plate having a front fluid channel in a front plate surface, a rear fluid channel in a rear plate surface, and a fluid port extending through the fluid transfer plate from the front fluid channel to the rear fluid channel. The front fluid channel, the rear fluid channel, and the fluid port are in fluid communication with the syringe cavity.

In an embodiment, the cartridge manifold includes a piston having an end seal. The piston is movable from an open position in which the end seal unseals the fluid port to allow cooling fluid to pass through the fluid port to a closed position in which the end seal seals the fluid port to stop the cooling fluid from passing through the fluid port.

In an embodiment, the cartridge manifold includes an aft plate apposed to the rear plate surface of the fluid transfer plate. The cartridge manifold includes a channel seal extending around the rear fluid channel. The channel seal is sandwiched between the rear plate surface and the aft plate.

In an embodiment, the end seal presses against the rear plate surface of the fluid transfer plate and a side seal to seal against the aft plate.

In an embodiment, the piston is spring-loaded to move the piston from the open position to the closed position.

In an embodiment, a generator for an ultrasound-based treatment system includes a generator housing having a cartridge receptacle configured to receive a fluid transfer cartridge. The generator includes a pressure fitting mounted on the generator housing. The pressure fitting is configured to connect to a conduit of the fluid transfer cartridge. The generator includes a pressure sensor within the generator housing. The pressure sensor is configured to sense pressure at the pressure fitting.

In an embodiment, the generator includes a chamber having a chamber inlet connected to the pressure fitting and a chamber outlet connected to the pressure sensor.

In an embodiment, an ultrasound-based treatment system includes a generator including a generator housing. The ultrasound-based treatment system includes a pneumatic fitting mounted on the generator housing. The ultrasound-based treatment system includes a pneumatic drive system in the generator housing. The pneumatic drive system is connected to the pneumatic fitting. The pneumatic drive system is configured to apply one or more of positive pressure or negative pressure to the pneumatic fitting.

In an embodiment, the ultrasound-based treatment system includes one or more syringes. Each of the one or more syringes includes a stopper disposed within a syringe barrel between a distal syringe cavity and a proximal syringe cavity. The proximal syringe cavity is in fluid communication with the pneumatic fitting. The distal syringe cavity is in fluid communication with a fluid reservoir.

In an embodiment, a generator for an ultrasound-based treatment system includes a generator housing having a cartridge receptacle configured to receive a fluid transfer cartridge. The generator includes a non-contact position sensor mounted in the generator housing. The non-contact position sensor is configured to detect a position of a syringe piston of the fluid transfer cartridge.

In an embodiment, the non-contact position sensor includes one or more time-of-flight sensors.

In an embodiment, the non-contact position sensor includes one or more proximity sensors.

In an embodiment, an ultrasound-based treatment system includes a fluid reservoir holder having an attachment to hold a fluid reservoir. The ultrasound-based treatment system includes a weight sensor coupled to the attachment to generate weight data based on a weight of the fluid reservoir. The ultrasound-based treatment system includes one or more processors configured to receive the weight data from the weight sensor, and determine, based on the weight data, whether the fluid reservoir is a predetermined fluid reservoir.

In an embodiment, the one or more processors are further configured to detect, based on the weight data, a leak in the fluid reservoir.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A fluid transfer cartridge, comprising:
a cartridge shell having a cartridge cavity between a front face and a rear face;
a syringe barrel disposed within the cartridge cavity and having a syringe cavity; and
a cartridge manifold in the cartridge cavity, wherein the cartridge manifold includes a fluid transfer plate having a front fluid channel formed in and extending along a front plate surface, a rear fluid channel formed in and extending along a rear plate surface, and a fluid port extending through the fluid transfer plate from the front fluid channel to the rear fluid channel, and wherein the front fluid channel, the rear fluid channel, and the fluid port are in fluid communication with the syringe cavity.

2. The fluid transfer cartridge of claim 1, wherein the cartridge manifold includes a piston having an end seal, wherein the piston is movable from an open position in which the end seal unseals the fluid port to allow cooling fluid to pass through the fluid port to a closed position in which the end seal seals the fluid port to stop the cooling fluid from passing through the fluid port.

3. The fluid transfer cartridge of claim 2, wherein the end seal has a circular distal surface.

4. The fluid transfer cartridge of claim 2, wherein the end seal includes an O-ring.

5. The fluid transfer cartridge of claim 2, wherein the cartridge manifold includes an aft plate apposed to the rear plate surface of the fluid transfer plate, wherein the cartridge manifold includes a channel seal extending around the rear fluid channel, and wherein the channel seal is sandwiched between the rear plate surface and the aft plate.

6. The fluid transfer cartridge of claim 5, wherein a rear surface of the piston is rearward of a back surface of the aft plate in the closed position and the open position.

7. The fluid transfer cartridge of claim 5, wherein the end seal presses against the rear plate surface of the fluid transfer plate and a side seal to seal against the aft plate.

8. The fluid transfer cartridge of claim 2, wherein the piston is spring-loaded to move the piston from the open position to the closed position.

9. The fluid transfer cartridge of claim 8, wherein the piston includes an annular groove to receive a spring to spring-load the piston.

10. The fluid transfer cartridge of claim 1, wherein the fluid transfer plate is sandwiched between a fore plate and an aft plate, and wherein the fore plate is snap fit to the aft plate.

11. A treatment system, comprising:
a fluid transfer cartridge including a cartridge shell having a cartridge cavity between a front face and a rear face, a syringe barrel disposed within the cartridge cavity and having a syringe cavity, and a cartridge manifold in the cartridge cavity, wherein the cartridge manifold includes a fluid transfer plate having a front fluid channel formed in and extending along a front plate surface, a rear fluid channel formed in and extending along a rear plate surface, and a fluid port extending through the fluid transfer plate from the front fluid channel to the rear fluid channel, and wherein the front fluid channel, the rear fluid channel, and the fluid port are in fluid communication with the syringe cavity, and
a generator having a generator housing including a cartridge receptacle configured to receive the fluid transfer cartridge.

12. The treatment system of claim 11, wherein the cartridge manifold includes a piston having an end seal, wherein the piston is movable from an open position in which the end seal unseals the fluid port to allow cooling fluid to pass through the fluid port to a closed position in which the end seal seals the fluid port to stop the cooling fluid from passing through the fluid port.

13. The treatment system of claim 12, wherein the end seal has a circular distal surface.

14. The treatment system of claim 12, wherein the end seal includes an O-ring.

15. The treatment system of claim 12, wherein the cartridge manifold includes an aft plate apposed to the rear plate surface of the fluid transfer plate, wherein the cartridge manifold includes a channel seal extending around the rear fluid channel, and wherein the channel seal is sandwiched between the rear plate surface and the aft plate.

16. The treatment system of claim 15, wherein a rear surface of the piston is rearward of a back surface of the aft plate in the closed position and the open position.

17. The treatment system of claim 15, wherein the end seal presses against the rear plate surface of the fluid transfer plate and a side seal to seal against the aft plate.

18. The treatment system of claim 12, wherein the piston is spring-loaded to move the piston from the open position to the closed position.

19. The treatment system of claim 18, wherein the piston includes an annular groove to receive a spring to spring-load the piston.

20. The treatment system of claim 11, wherein the fluid transfer plate is sandwiched between a fore plate and an aft plate, and wherein the fore plate is snap fit to the aft plate.

21. A cartridge manifold, comprising:
a fluid transfer plate having a front fluid channel formed in and extending along a front plate surface, a rear fluid channel formed in and extending along a rear plate surface, and a fluid port extending through the fluid transfer plate from the front fluid channel to the rear fluid channel; and
a piston having an end seal, wherein the piston is movable from an open position in which the end seal unseals the fluid port to allow cooling fluid to pass through the fluid port to a closed position in which the end seal seals the fluid port to stop the cooling fluid from passing through the fluid port.

22. The fluid transfer cartridge of claim 21, wherein the end seal has a circular distal surface.

23. The fluid transfer cartridge of claim 21, wherein the end seal includes an O-ring.

24. The fluid transfer cartridge of claim 21, wherein the cartridge manifold includes an aft plate apposed to the rear plate surface of the fluid transfer plate, wherein the cartridge manifold includes a channel seal extending around the rear fluid channel, and wherein the channel seal is sandwiched between the rear plate surface and the aft plate.

25. The fluid transfer cartridge of claim 24, wherein a rear surface of the piston is rearward of a back surface of the aft plate in the closed position and the open position.

26. The fluid transfer cartridge of claim 24, wherein the end seal presses against the rear plate surface of the fluid transfer plate and a side seal to seal against the aft plate.

27. The fluid transfer cartridge of claim 21, wherein the piston is spring-loaded to move the piston from the open position to the closed position.

28. The fluid transfer cartridge of claim 27, wherein the piston includes an annular groove to receive a spring to spring-load the piston.

29. The fluid transfer cartridge of claim 21, wherein the fluid transfer plate is sandwiched between a fore plate and an aft plate, and wherein the fore plate is snap fit to the aft plate.

* * * * *